(12) United States Patent
Showe et al.

(10) Patent No.: US 12,227,808 B2
(45) Date of Patent: Feb. 18, 2025

(54) COMPOSTIONS AND METHODS FOR DIAGNOSING LUNG CANCERS USING GENE EXPRESSION PROFILES

(71) Applicant: The Wistar Institute of Anatomy and Biology, Philadelphia, PA (US)

(72) Inventors: Michael Showe, Media, PA (US); Louise C. Showe, Media, PA (US); Andrew V. Kossenkov, Huntingdon Valley, PA (US)

(*) Notice: Subject to any disclaimer, the term of this patent is extended or adjusted under 35 U.S.C. 154(b) by 0 days.

(21) Appl. No.: 16/954,370

(22) PCT Filed: Dec. 19, 2018

(86) PCT No.: PCT/US2018/066531
§ 371 (c)(1),
(2) Date: Jun. 16, 2020

(87) PCT Pub. No.: WO2019/126343
PCT Pub. Date: Jun. 27, 2019

(65) Prior Publication Data
US 2021/0079479 A1 Mar. 18, 2021

Related U.S. Application Data

(60) Provisional application No. 62/752,163, filed on Oct. 29, 2018, provisional application No. 62/607,756, filed on Dec. 19, 2017.

(51) Int. Cl.
*C12Q 1/6886* (2018.01)

(52) U.S. Cl.
CPC ...... *C12Q 1/6886* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | |
|---|---|---|
| 6,582,908 B2 | 6/2003 | Fodor et al. |
| 7,081,340 B2 | 7/2006 | Baker et al. |
| 2007/0099209 A1 | 5/2007 | Clarke et al. |
| 2009/0317392 A1 | 12/2009 | Nakamura et al. |
| 2010/0255486 A1 | 10/2010 | Showe et al. |
| 2011/0201517 A1 | 8/2011 | Kolman et al. |
| 2012/0021946 A1 | 1/2012 | Nakamura et al. |
| 2014/0005065 A1 | 1/2014 | Showe et al. |
| 2014/0227372 A1 | 8/2014 | Missiaglia et al. |
| 2015/0315643 A1 | 11/2015 | O'Garra et al. |
| 2016/0348151 A1* | 12/2016 | Wyrich .............. C12N 15/1003 |

FOREIGN PATENT DOCUMENTS

| | | |
|---|---|---|
| WO | WO-2007/141004 A1 | 12/2007 |
| WO | WO-2009/075799 A2 | 6/2009 |
| WO | WO-2010/030697 A1 | 3/2010 |
| WO | WO-2010/064702 A1 | 6/2010 |
| WO | WO-2012/006632 A3 | 1/2012 |
| WO | WO-2012/150275 A1 | 11/2012 |
| WO | WO-2013/153130 A1 | 10/2013 |
| WO | WO-2016/011068 A1 | 1/2016 |
| WO | WO-2017/223216 A1 | 12/2017 |
| WO | WO-2019126343 A1 | 6/2019 |

OTHER PUBLICATIONS

NEB catalog (1998/1999 pp. 121, 284) (Year: 1999).*
Aberle, D. R. et al. Reduced lung-cancer mortality with low-dose computed tomographic screening. *N Engl J Med* Pub. Online Jun. 29, 2011; vol. 365:395-409.
Ahern, H. Biochemical, reagent kits offer scientists good return on investment *The Scientist* Jul. 23, 1995; vol. 9(15): 1-5.
Ayers, M. et al. IFN-β-related mRNA profile predicts clinical response to PD-1 blockade. *The Journal of Clinical Investigation* Jun. 26, 2017; vol. 127: 2930-2940.
Azharuddin, M. et al. Evaluating pulmonary nodules to detect lung cancer: Does Fleischner criteria really work? *Journal of Cancer Research and Practice* Jun. 29, 2017; vol. 5: 13-19.
Brenner, S. et al., Gene expression analysis by massively parallel signature sequencing (MPSS) on microbead arrays. *Nature Biotechnology* Jun. 2000 vol. 18(6): 630-634.
Chung, K. et al. Brock malignancy risk calculator for pulmonary nodules: validation outside a lung cancer screening population. *Thorax* May 18, 2018 vol. 73: 857-863.
Croswell, J. et al. Cumulative incidence of false-positive test results in lung cancer screening: a randomized trial. *Ann Intern Med* Apr. 20, 2010; vol. 152: 505-512.
Debey-Pascher, S. et al. RNA stabilization of peripheral blood and profiling by bead chip analysis. *Methods Mol Biol* 2009; vol. 496: 175-210.
Draghici, S. et al. Reliability and reproducibility issues in DNA microarray measurements. *Trends Genet* Online Dec. 27, 2005; vol. 22(2): 101-109.
Fricano, M. M. et al. Global transcriptomic profiling using small volumes of whole blood: a cost-effective method for translational genomic biomarker identification in small animals. *Int J Mol Sci* Apr. 13, 2011; vol. 12(4): 2502-2517.
Geiss, G.K. et al. Direct multiplexed measurement of gene expression with color-coded probe pairs. *Nat Biotechnol* Feb. 17, 2008; vol. 26(3): 317-25.
Gierada, D.S. et al. Projected Outcomes Using Different Nodule Sizes to Define a Positive CT Lung Cancer Screening Examination. *Journal of the National Cancer Institute* Oct. 18, 2014; vol. 106: dju284.
Gong, J. et al. A pan-cancer analysis of the expression and clinical relevance of small nucleolar RNAs in human cancer. *Cell Reports* Nov. 14, 2017. vol 21: 1968-1981.

(Continued)

*Primary Examiner* — Katherine D Salmon
(74) *Attorney, Agent, or Firm* — Howson & Howson, LLP; Colleen M. Schaller; Richard F. Kane

(57) ABSTRACT

Methods and compositions are provided for diagnosing lung cancer in a mammalian subject by use of 7 or more selected genes, e.g., a gene expression profile, from the blood of the subject which is characteristic of disease. The gene expression profile includes 7 or more genes of Table I, Table II, Table III, Table IV or Table IX herein.

4 Claims, 13 Drawing Sheets

(56) References Cited

OTHER PUBLICATIONS

Gould, M.K. et al. A Clinical Model to Estimate the Pretest Probability of Lung Cancer in Patients With Solitary Pulmonary Nodules. *Chest* Feb. 1, 2007; vol. 131(2): 383-388.

Guyon, I. et al. Gene Selection for Cancer Classification using Support Vector Machines. *Machine Learning* Jan. 2002; vol. 46: 389-422.

Henschke, C.I. et al. CT screening for lung cancer: update 2007. *Oncologist* Jan. 1, 2008; vol. 13(1): 65-78.

Henschke, C.I. et al. The role of CT screening for lung cancer. *Thorac Surg Clin* May 2007; vol. 17(2): 137-142.

Heuvers, M.E. et al. Generalizability of results from the National Lung Screening Trial. *European journal of epidemiology* Online Aug. 8, 2012; vol. 27(9): 669-672.

Hoseok, I.; Cho, J.Y. Lung Cancer Biomarkers. *Adv Clin Chem* Sep. 3, 2015; vol. 72: 107-170.

Kathuria, H. et al. Updates and controversies in the rapidly evolving field of lung cancer screening, early detection, and chemoprevention. *Cancers (Basel)* May 16, 2014; vol. 6(2): 1157-1179.

Kennedy, L. et al. Hematopoietic Lineage Transcriptome Stability and Representation in PAXgene Collected Peripheral Blood Utilising SPIA Single-Stranded cDNA Probes for Microarray. *Biomark Insights* Aug. 25, 2008; vol. 3: 403-417.

Kossenkov, A. V. et al. Resection of non-small cell lung cancers reverses tumor-induced gene expression changes in the peripheral immune system. *Clin Cancer Res* Sep. 15, 2011; vol. 17(18): 5867-5877.

Kossenkov, A.V. et al. Peripheral immune cell gene expression predicts survival of patients with non-small cell lung cancer. *PLoS One* Mar. 29, 2012; vol. 7(3): e34392.

Li, X.J. et al. A blood-based proteomic classifier for the molecular characterization of pulmonary nodules. *Sci Transl Med* Oct. 16, 2013; vol. 5(207): 207ra142.

Li, C.M. et al. Current and future molecular diagnostics in non-small-cell lung cancer. *Expert Rev Mol Diagn* Jul. 7, 2015; vol. 15(8): 1061-1074.

Martin, M.D. et al. Lung-RADS: Pushing the Limits. *RadioGraphics* Oct. 20, 2017; vol. 37, 1975-1993.

Massion, P.P .; Walker, R.C. Indeterminate Pulmonary Nodules: Risk for Having or for Developing Lung Cancer? *Cancer Prev Res (Phila)* Oct. 27, 2014: vol. 7(12): 1173-1178.

McWilliams, A. et al. Probability of Cancer in Pulmonary Nodules Detected on First Screening CT. *New England Journal of Medicine* Sep. 5, 2013; vol. 369, 910-919.

Perez-Rogers, J.F. et al. Shared Gene Expression Alterations in Nasal and Bronchial Epithelium for Lung Cancer Detection. *Journal of the National Cancer Institute* Feb. 27, 2017; vol. 109(7): djw327.

Redberg, R.F.; O'Malley, P.G. Important questions about lung cancer screening programs when incidental findings exceed lung cancer nodules by 40 to 1. *JAMA Internal Medicine* Mar. 2017; vol. 177(3): 311-312.

Redente, E.F. et al. Tumor signaling to the bone marrow changes the phenotype of monocytes and pulmonary macrophages during urethane-induced primary lung tumorigenesis in A/J mice. *Am J Pathol* Feb. 2007; vol. 170(2): 693-708.

Redente, E.F. et al. Differential polarization of alveolar macrophages and bone marrow-derived monocytes following chemically and pathogen-induced chronic lung inflammation. *J Leukoc Biol* Apr. 1, 2010; vol. 88(1): 159-168.

Redente, E.F. et al. Tumor progression stage and anatomical site regulate tumor-associated macrophage and bone marrow-derived monocyte polarization. *Am J Pathol* Apr. 29, 2010; vol. 176(6): 2972-2985.

Rooney, C. et al. AACR 10th Annual Meeting Abstract 2407: Expression Profiling of FGF-receptor pathway genes in squamous NSCLC tissue using Nanostring. *Cancer Research*, Apr. 2013, vol. 73, No. 8.

Ruparel, M. et al. Pulmonary nodules and CT screening: the past, present and future. *Thorax* Feb. 26, 2016; vol. 71(4): 367-375.

Showe, M.K. et al. The peripheral immune response and lung cancer prognosis. *Oncoimmunology* Nov. 1, 2012; vol. 1(8): 1414-1416.

Showe, M.K. et al. Gene expression profiles in peripheral blood mononuclear cells can distinguish patients with non-small cell lung cancer from patients with nonmalignant lung disease. *Cancer Res* Dec. 15, 2009; vol. 69(24): 9202-9210.

Silvestri, G.A. et al. A Bronchial Genomic Classifier for the Diagnostic Evaluation of Lung Cancer, *N Engl J Med* Jul. 16, 2015; vol. 373(3): 243-251.

Silvestri, G.A. et al. Assessment of Plasma Proteomics Biomarker's Ability to Distinguish Benign From Malignant Lung Nodules: Results of the PANOPTIC (Pulmonary Nodule Plasma Proteomic Classifier) Trial. *Chest* Feb. 26, 2018; vol. 154(3): 491-500.

Sun, Z. et al. Can gene expression profiling predict survival for patients with squamous cell carcinoma of the lung? *Molecular Cancer* Dec. 3, 2004; vol. 3:35.

Vachani, A. et al. A Blood-Based Multi-Gene Expression Classifier to Distinguish Benign From Malignant Pulmonary Nodules. *CHEST* Oct. 1, 2017; vol. 152(4): A629-A630.

Vachani, A. et al. Factors That Influence Physician Decision Making for Indeterminate Pulmonary Nodules. *Annals of the American Thoracic Society* Dec. 2014; vol. 11(10): 1586-1591.

Velculescu, V.E. et al. Characterization of the yeast transcriptome. *Cell* Jan. 24, 1997; vol. 88(2): 243-51.

Velculescu, V.E. et al. Serial analysis of gene expression. *Science* Oct. 20, 1995, vol. 270(5235): 484-487.

Wallden, B. et al. Development and verification of the PAM50-based Prosigna breast cancer gene signature assay. *BMC Medical Genomics* Aug. 22, 2015; vol. 8: 54.

Wei, Q.; Dunbrack, R.L. The Role of Balanced Training and Testing Data Sets for Binary Classifiers in Bioinformatics. *PLoS One* Jul. 9, 2013; vol. 8(7): e67863.

Supplementary Partial European Search Report issued in counterpart European Patent Application No. 18890571.5, dated Jul. 14, 2021.

International Search Report and Written Opinion issued on International Patent Application No. PCT/US2017/038571, dated Nov. 30, 2017.

Extended Search Report issued in related European Patent Application No. 17816148.5, dated Jan. 21, 2020.

Search Report and Written Opinion issued in related Singapore Patent Application No. 11201810914V, dated Apr. 18, 2020.

International Search Report and Written Opinion issued on International Patent Application No. PCT/US2018/066531, dated Aug. 5, 2019.

Restriction Requirement, dated Nov. 13, 2020, issued on U.S. Appl. No. 16/312,036 and Response.

Non-Final Office Action, dated Aug. 2, 2021, issued on U.S. Appl. No. 16/312,036 and Response.

Office Action issued in related Canadian Patent Application No. 3,026,809, dated Jun. 4, 2020.

Office Action issued in related European Patent Application No. 17816148.5, dated Mar. 22, 2021.

Examination Report issued in related Indian Patent Application No. 201817048359, dated Jan. 29, 2021.

International Preliminary Examination Report for International Application No. PCT/US2018/066531, dated Dec. 19, 2018.

Manufacturer's instructions accompanying the product GENEAMP RNA PCR kit (Perkin Elmer, Calif., USA, 1996).

XP002254749, "Affymetrix GeneChip Human Genome U133 Array Set HG-U133A", GEO, Mar. 11, 2002.

NCBI (2009) "PREDICTED: *Homo sapiens* similar to CG10103 (LOC728533), misc RNA" (Year: 2009).

GA Accession No. GPL96, Mar. 2002.

Preanalytix (https://www.preanalytix.com) for the PAXgene Blood RNA Tube (IVD), accessed Nov. 15, 2021.

Aug. 5, 2019, WO, PCT/US2018/066531.

Sun, Molecular Cancer, Can gene expression profiling predict survival for patients with squamous cell carcinoma of the lung?, vol. 3(1): 1968-1981, Nov. 14, 2017.

(56) References Cited

OTHER PUBLICATIONS

Gong, Cell Reports, A pan-cancer analysis of the expression and clinical relevance of small nucleolar RNAs in human cancer, vol. 21(7): 1968-1981, Nov. 14, 2017.

* cited by examiner

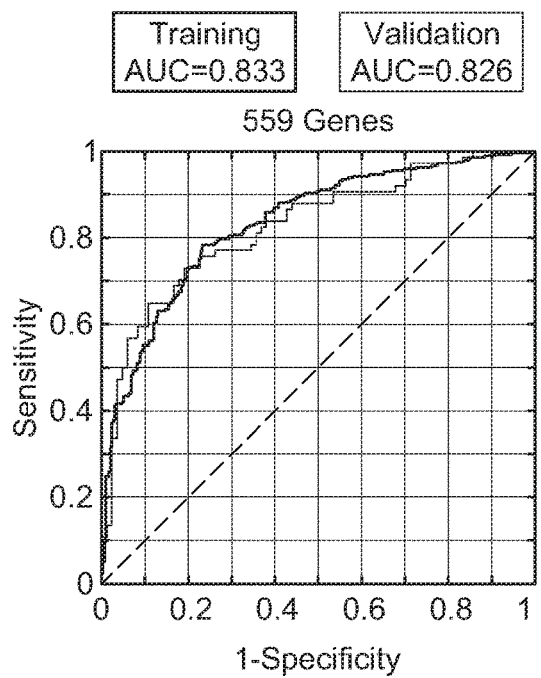
FIG. 4A
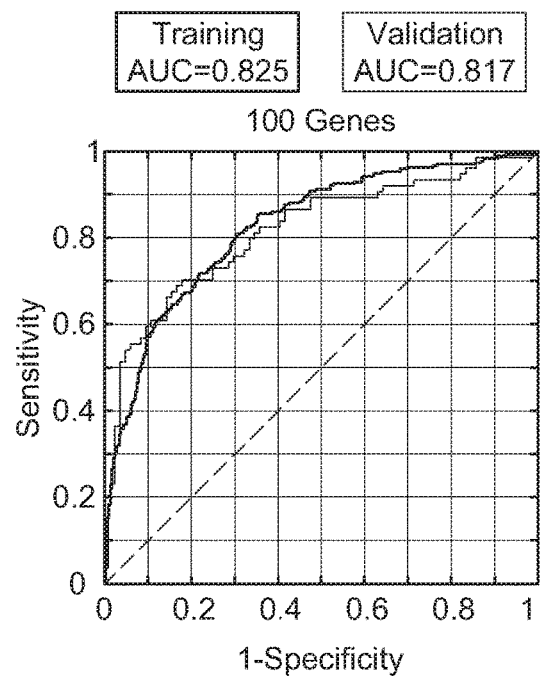
FIG. 4B
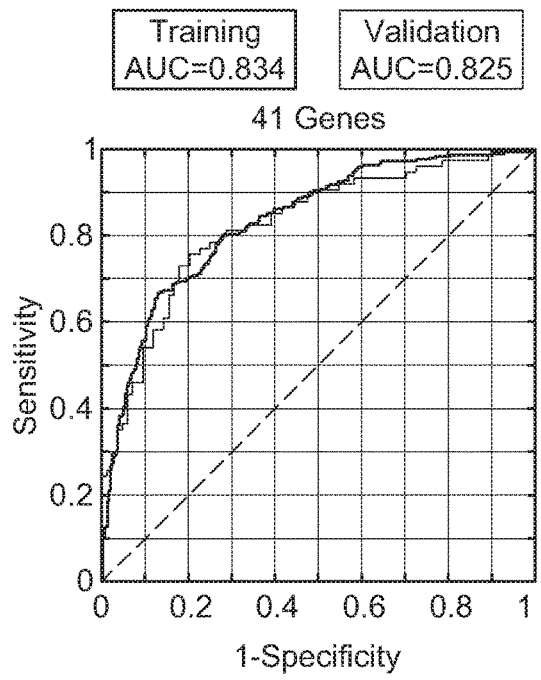
FIG. 4C
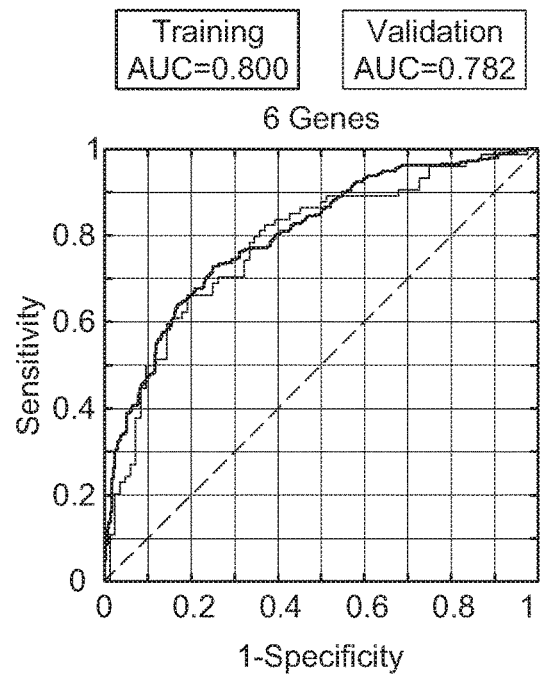
FIG. 4D
| Classification score | -14 | -10 | -6.6 | -4.1 | -2 | -0.1 | 1.7 | 3.8 | 6.3 | 10 | 14 |
|---|---|---|---|---|---|---|---|---|---|---|---|
| Cancer probability | 5% | 10% | 20% | 30% | 40% | 50% | 60% | 70% | 80% | 90% | 95% |
FIG. 4E

|  | ROC-AUC | | | | Specificity at 90% sensitivity | | | |  |
|---|---|---|---|---|---|---|---|---|---|
|  | 0.7  0.75  0.8  0.85  0.9  0.95 | | | | 0.2  0.3  0.4  0.5  0.6  0.7 | | | |  |
| 10mm | 0.77 BN:110 MN:221 | 0.76 BN:88 MN:93 | 0.75 BN:59 MN:50 | 0.70 BN:17 MN:11 | 46% BN:110 MN:221 | 42% BN:88 MN:93 | 42% BN:59 MN:50 | 53% BN:17 MN:11 | Training |
| 8mm | 0.80 BN:145 MN:230 | 0.79 BN:123 MN:102 | 0.79 BN:94 MN:59 | 0.80 BN:52 MN:20 | 50% BN:145 MN:230 | 47% BN:123 MN:102 | 43% BN:94 MN:59 | 54% BN:52 MN:20 |  |
| 6mm | 0.81 BN:194 MN:237 | 0.80 BN:172 MN:109 | 0.80 BN:143 MN:66 | 0.81 BN:101 MN:27 | 48% BN:194 MN:237 | 41% BN:172 MN:109 | 41% BN:143 MN:66 | 39% BN:101 MN:27 |  |
| 4mm | 0.84 BN:283 MN:237 | 0.82 BN:261 MN:109 | 0.82 BN:232 MN:66 | 0.82 BN:190 MN:27 | 52% BN:283 MN:237 | 44% BN:261 MN:109 | 44% BN:232 MN:66 | 42% BN:190 MN:27 |  |
| Min | 0.84 BN:286 MN:237 | 0.82 BN:264 MN:109 | 0.82 BN:235 MN:66 | 0.82 BN:193 MN:27 | 52% BN:286 MN:237 | 44% BN:264 MN:109 | 43% BN:235 MN:66 | 41% BN:193 MN:27 |  |
| 10mm | 0.82 BN:32 MN:54 | 0.80 BN:28 MN:29 | 0.85 BN:17 MN:8 |  | 38% BN:32 MN:54 | 18% BN:28 MN:29 | 12% BN:17 MN:8 |  | Validation |
| 8mm | 0.80 BN:40 MN:58 | 0.78 BN:36 MN:33 | 0.81 BN:25 MN:12 | 0.87 BN:14 MN:6 | 35% BN:40 MN:58 | 22% BN:36 MN:33 | 64% BN:25 MN:12 | 64% BN:14 MN:6 |  |
| 6mm | 0.80 BN:55 MN:59 | 0.78 BN:51 MN:34 | 0.79 BN:40 MN:13 | 0.81 BN:29 MN:7 | 33% BN:55 MN:59 | 25% BN:51 MN:34 | 40% BN:40 MN:13 | 45% BN:29 MN:7 |  |
| 4mm | 0.81 BN:79 MN:61 | 0.79 BN:75 MN:36 | 0.80 BN:64 MN:15 | 0.82 BN:53 MN:9 | 44% BN:79 MN:61 | 29% BN:75 MN:36 | 47% BN:64 MN:15 | 51% BN:53 MN:9 |  |
| Min | 0.81 BN:82 MN:61 | 0.80 BN:78 MN:36 | 0.80 BN:67 MN:15 | 0.82 BN:56 MN:9 | 45% BN:82 MN:61 | 31% BN:78 MN:36 | 48% BN:67 MN:15 | 52% BN:56 MN:9 |  |

Nodule range from

FIG. 6-1

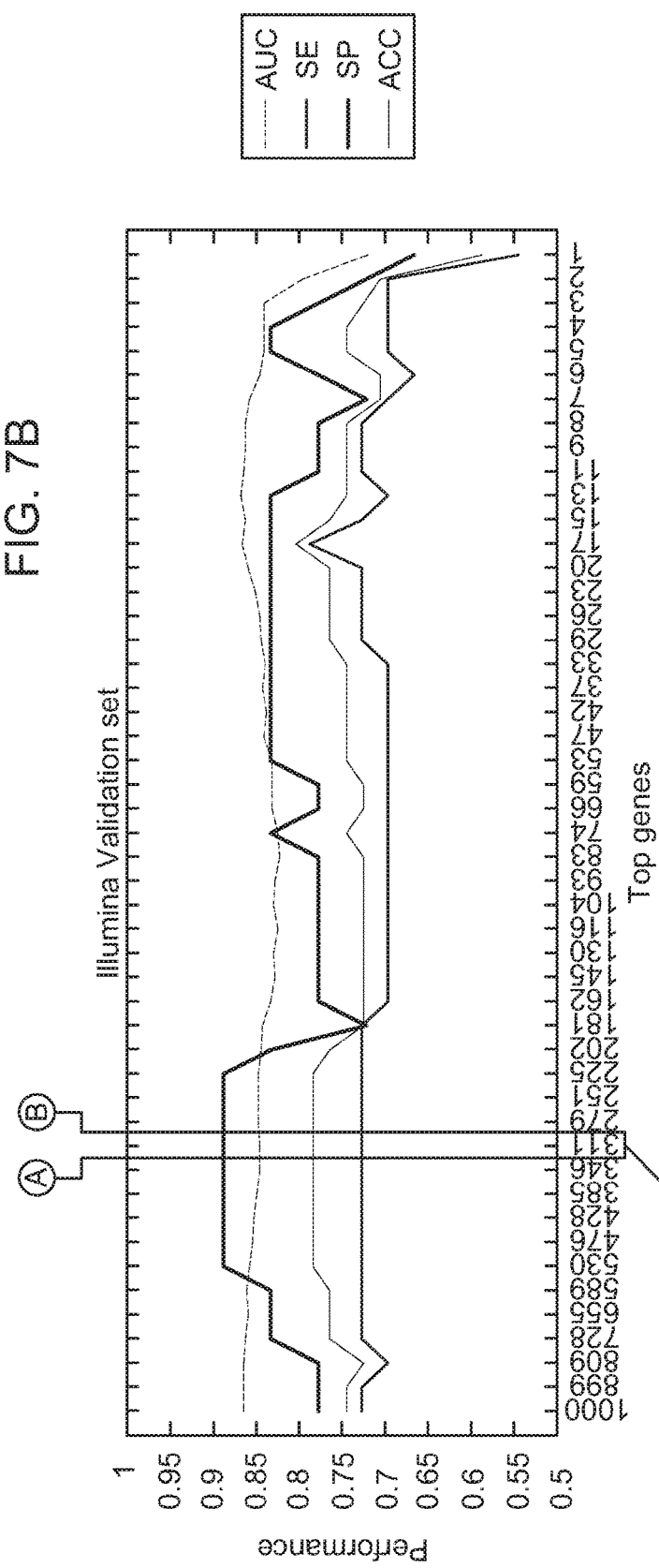
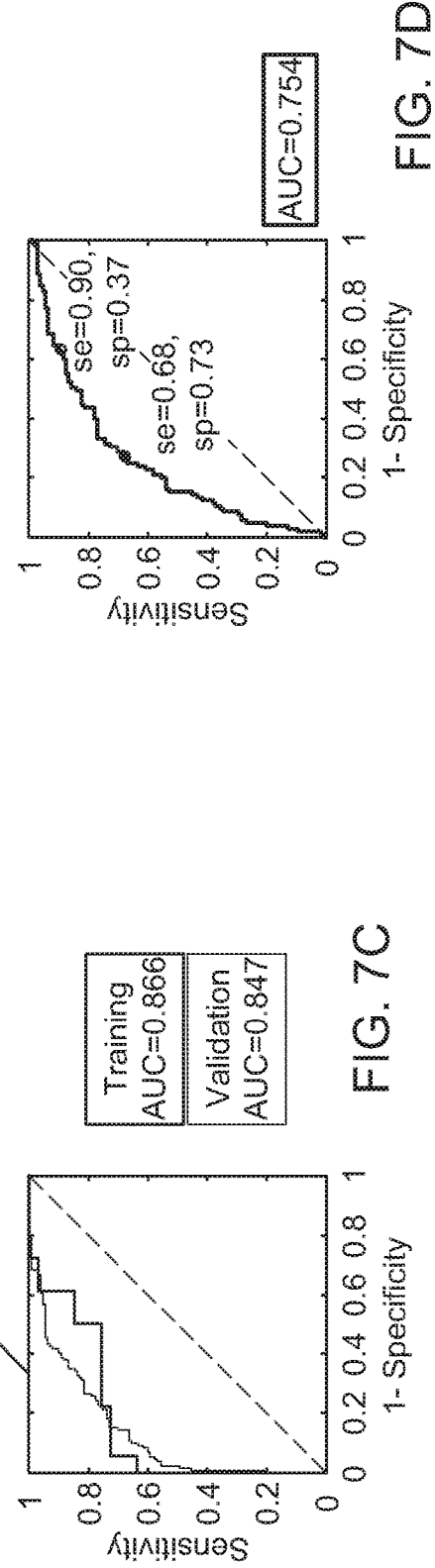
FIG. 7B
FIG. 7C
FIG. 7D

COMPOSTIONS AND METHODS FOR DIAGNOSING LUNG CANCERS USING GENE EXPRESSION PROFILES

This is a US National Stage Entry under 35 USC§ 271 of PCT/US2018/066531, which claims the benefit under 35 USC 119(e) of U.S. Provisional Patent Application No. 62/607,756, filed Dec. 19, 2017 and U.S. Provisional Patent Application No. 62/752,163, filed Oct. 29, 2018. These applications are incorporated by reference herein.

STATEMENT REGARDING FEDERALLY SPONSORED RESEARCH OR DEVELOPMENT

This invention was made with government support under Grant No. CA010815 awarded by the National Institutes of Health and the Grant No. 4100059200 (Diagnostic Markers for the Early-stage Lung Cancer in PAX Gene Blood Samples) awarded by the PA Department of Health, and Grant No. 5 U01 CA200495 awarded by the National Cancer Institute. The government has certain rights in the invention.

BACKGROUND OF THE INVENTION

Lung cancer is the most common worldwide cause of cancer mortality. In the United States, lung cancer is the second most prevalent cancer in both men and women and will account for more than 174,000 new cases per year and more than 162,000 cancer deaths. In fact, lung cancer accounts for more deaths each year than from breast, prostate and colorectal cancers combined.

The high mortality (80-85% in five years), which has shown little or no improvement in the past 30 years, emphasizes the fact that new and effective tools to facilitate early diagnosis prior to metastasis to regional nodes or beyond the lung are needed.

High risk populations include smokers, former smokers, and individuals with markers associated with genetic predispositions. Because surgical removal of early stage tumors remains the most effective treatment for lung cancer, there has been great interest in screening high-risk patients with low dose spiral CT (LDCT). This strategy identifies non-calcified pulmonary nodules in approximately 30-70% of high risk individuals but only a small proportion of detected nodules are ultimately diagnosed as lung cancers (0.4 to 2.7%). These large numbers of nodules being detected is likely to result in overtreatment and a burden on healthcare systems. Currently, the only way to differentiate subjects with lung nodules of benign etiology from subjects with malignant nodules is an invasive biopsy, surgery, or prolonged observation with repeated scanning. Even using the best clinical algorithms, 20-55% of patients selected to undergo surgical lung biopsy for indeterminate lung nodules, are found to have benign disease and those that do not undergo immediate biopsy or resection require sequential imaging studies. The use of serial CT in this group of patients runs the risk of delaying potential curable therapy, along with the costs of repeat scans, the not-insignificant radiation doses, and the anxiety of the patient.

Ideally, a diagnostic test would be easily accessible, inexpensive, demonstrate high sensitivity and specificity, and result in improved patient outcomes (medically and financially). Others have shown that classifiers which utilize epithelial cells have high accuracy. However, harvesting these cells requires an invasive bronchoscopy. See, Silvestri et al, N Engl J Med. 2015 July 16; 373(3): 243-251, which is incorporated herein by reference.

Efforts are in progress to develop non-invasive diagnostics using sputum, blood or serum and analyzing for products of tumor cells, methylated tumor DNA, single nucleotide polymorphism (SNPs) expressed messenger RNA or proteins. This broad array of molecular tests with potential utility for early diagnosis of lung cancer has been discussed in the literature. Although each of these approaches has its own merits, none has yet passed the exploratory stage in the effort to detect patients with early stage lung cancer, even in high-risk groups, or patients which have a preliminary diagnosis based on radiological and other clinical factors. A simple blood test, a routine event associated with regular clinical office visits, would be an ideal diagnostic test.

SUMMARY OF THE INVENTION

In one aspect, a composition or kit for diagnosing or evaluating a lung cancer in a mammalian subject includes at least seven (7) or more polynucleotides or oligonucleotides, wherein each polynucleotide or oligonucleotide hybridizes to a different gene, gene fragment, gene transcript or expression product in a patient sample. Each gene, gene fragment, gene transcript or expression product is selected from the genes of Table I, Table II, Table III, Table IV or Table IX. In one embodiment, at least one polynucleotide or oligonucleotide is attached to a detectable label. In one embodiment, the composition or kit includes polynucleotides or oligonucleotides which detect the gene, gene fragment, gene transcript or expression product of each of the genes in Table I, Table II, Table III, Table IV or Table IX. In one aspect, a composition or kit for diagnosing or evaluating a lung cancer in a mammalian subject includes at least 8 or more polynucleotides or oligonucleotides, wherein each polynucleotide or oligonucleotide hybridizes to a different gene, gene fragment, gene transcript or expression product in a patient sample. In one embodiment, the genes are selected from Table I, Table II, Table III, Table IV or Table IX. In one aspect, a composition or kit for diagnosing or evaluating a lung cancer in a mammalian subject includes at least 15 or more polynucleotides or oligonucleotides, wherein each polynucleotide or oligonucleotide hybridizes to a different gene, gene fragment, gene transcript or expression product in a patient sample. In one embodiment, the genes are selected from Table II, Table III, Table IV or Table IX. In one aspect, a composition or kit for diagnosing or evaluating a lung cancer in a mammalian subject includes at least 41 or more polynucleotides or oligonucleotides, wherein each polynucleotide or oligonucleotide hybridizes to a different gene, gene fragment, gene transcript or expression product in a patient sample. In one embodiment, the genes are selected from Table II, Table III, Table IV or Table IX. In one aspect, a composition or kit for diagnosing or evaluating a lung cancer in a mammalian subject includes at least 50 or more polynucleotides or oligonucleotides, wherein each polynucleotide or oligonucleotide hybridizes to a different gene, gene fragment, gene transcript or expression product in a patient sample. In one embodiment, the genes are selected from Table II, Table III, Table IV or Table IX.

In another aspect, a composition or kit for diagnosing or evaluating a lung cancer in a mammalian subject includes 7 or more ligands, wherein each ligand hybridizes to a different gene expression product in a patient sample. Each gene expression product is selected from the genes of Table I, Table II, Table III, Table IV or Table IX. In one embodiment, at least one ligand is attached to a detectable label. In one embodiment, the composition or kit includes ligands which detect the expression products of each of the genes in Table I, Table II, Table III, Table IV or Table IX. In another embodiment, the composition or kit includes ligands which detect the expression products of at least 8 genes. In another embodiment, the composition or kit includes ligands which detect the expression products of at least 15 genes. In another embodiment, the composition or kit includes ligands which detect the expression products of at least 41 genes. In another embodiment, the composition or kit includes ligands which detect the expression products of at least 50 genes. In one embodiment, the genes are selected from Table II, Table III, Table IV or Table IX.

The compositions described herein enable detection of changes in expression in the genes in the subject's gene expression profile from that of a reference gene expression profile. The various reference gene expression profiles are described below. In one embodiment, the composition provides the ability to distinguish a cancerous tumor from a non-cancerous nodule.

In another aspect, a method for diagnosing or evaluating a lung cancer in a mammalian subject involves identifying changes in the expression of three or more genes in the sample of a subject, said genes selected from the genes of Table I, Table II, Table III, Table IV or Table IX, and comparing that subject's gene expression levels with the levels of the same genes in a reference or control, wherein changes in expression of said gene expression correlates with a diagnosis or evaluation of a lung cancer. In one embodiment, the changes in expression of said gene expression provides the ability to distinguish a cancerous tumor from a non-cancerous nodule.

In another aspect, a method for diagnosing or evaluating a lung cancer in a mammalian subject involves identifying a gene expression profile in the blood of a subject, the gene expression profile comprising 7 or more gene expression products of 8 or more informative genes as described herein. The 7 or more informative genes are selected from the genes of Table I, Table II, Table III, Table IV or Table IX. In one embodiment, 8 or more informative genes are selected from the genes of Table I, Table II, Table III, Table IV or Table IX. In one embodiment, the gene expression profile contains 15 genes selected from Table II, Table III, Table IV or Table IX. In one embodiment, the gene expression profile contains 41 genes selected from Table II, Table III, Table IV or Table IX. The subject's gene expression profile is compared with a reference gene expression profile from a variety of sources described below. Changes in expression of the informative genes correlate with a diagnosis or evaluation of a lung cancer. In one embodiment, the changes in expression of said gene expression provides the ability to distinguish a cancerous tumor from a non-cancerous nodule.

In another aspect, a method of detecting lung cancer in a patient is provided. The method includes obtaining a sample from the patient; and detecting a change in expression in at least 7 genes selected from Table I, Table II, Table III, Table IV or Table IX in the patient sample as compared to a control by contacting the sample with a composition comprising oligonucleotides, polynucleotides or ligands specific for each different gene transcript or expression product of the at least 8 genes of Table I, Table II, Table III, Table IV or Table IX and detecting binding between the oligonucleotide, polynucleotide or ligand and the gene product or expression product.

In yet another aspect, a method of diagnosing lung cancer in a subject is provided. The method includes obtaining a blood sample from a subject; detecting a change in expression in at least 8 genes selected from Table I, Table II, Table III, Table IV or Table IX in the patient sample as compared to a control by contacting the sample with a composition comprising oligonucleotides, polynucleotides or ligands specific for each different gene transcript or expression product of the at least 7 genes of Table I, Table II, Table III, Table IV or Table IX and detecting binding between the oligonucleotide, polynucleotide or ligand and the gene product or expression product; and diagnosing the subject with cancer when changes in expression of the subject's genes from those of the reference are detected.

In another aspect, a method of diagnosing and treating lung cancer in a subject having a neoplastic growth is provided. The method includes obtaining a blood sample from a subject; extracting the blood RNA and detecting a change in expression in at least 7 genes selected from Table I, Table II, Table III, Table IV or Table IX in the patient RNA sample as compared to a control by contacting the sample with a composition comprising oligonucleotides, polynucleotides or ligands specific for each different gene transcript or expression product of the at least 7 gene of Table I, Table II, Table III, Table IV or Table IX and detecting binding between the oligonucleotide, polynucleotide or ligand and the gene product or expression product; diagnosing the subject with cancer when changes in expression of the subject's genes from those of the reference are detected; and removing the neoplastic growth. Other appropriate treatments may also be provided.

Other aspects and advantages of these compositions and methods are described further in the following detailed description of the preferred embodiments thereof.

BRIEF DESCRIPTION OF THE DRAWINGS

FIG. 1A—Training set performance. FIG. 1B—Testing set performance.

FIG. 2A—Training set and 8-20 mm lesion validation set ROC curve using all genes for SVM classification. FIG. 2B—Training and validation set performance using the top 100 genes selected by RFE. FIG. 2C—Performance of training and validation sets using top 50 genes. FIG. 2D—Performance of training and validation sets using top 15 genes.

FIG. 4A-FIG. 4E show classification performance of NanoString lung nodule classifier. FIG. 4A-FIG. 4D—Comparison of ROC-AUC in training and validation sets with progressive reduction of the numbers of probes. FIG. 4E—The calculated probability of malignancy for an individual nodule for different classification scores using the 41-probe nPNC.

FIG. 5A—Compared to The Brock University, Mayo Clinic, and Veteran's Affairs (VA) lung cancer risk clinical models. FIG. 5B—Compared to classification by nodule maximum diameter

FIG. 7A-FIG. 7D demonstrate performance of the Pulmonary Nodule Classifier. A. Illumina microarrays training set performance across different iterations of the SVM-RFE process. Box highlights selected optimal number of genes. B. Testing set performance. C. Comparison of ROC-AUC performance of Illumina gene expression classifier based on expression of 311 gene probes between training and validation sets. D. 10-fold cross-validation performance of gene expression from NanoString PanCancer Immune panel on the training set. AUC=area under ROC curve, ACC=accuracy, SE=sensitivity, SP=specificity.

FIG. 8A—Plot shows individual sample classification scores from SVM model based on 10-fold cross-validation resampled 10 times using genes selected by SVM from the Illumina platform. FIG. 8B—ROC curves resulting from classifying 199 samples run on both NanoString and Illumina using gene selected from Illumina by SVM-RFE.

FIG. 9A. Training Set: Recursive Feature Elimination performed on each of 10 folds in the training set. Folds were resampled 10 times. The performance of the average of the scores from 10 re-samplings is shown. On the x-axis the number for genes remaining per fold is shown. FIG. 9B—Validation Set. The top genes were selected from all 100 gene lists at each iteration, and their performance was evaluated on the training set. FIG. 9C—Combined Set. All 741 samples used by SVM-RFE to rank probes.

DETAILED DESCRIPTION OF THE INVENTION

Figure 1A:
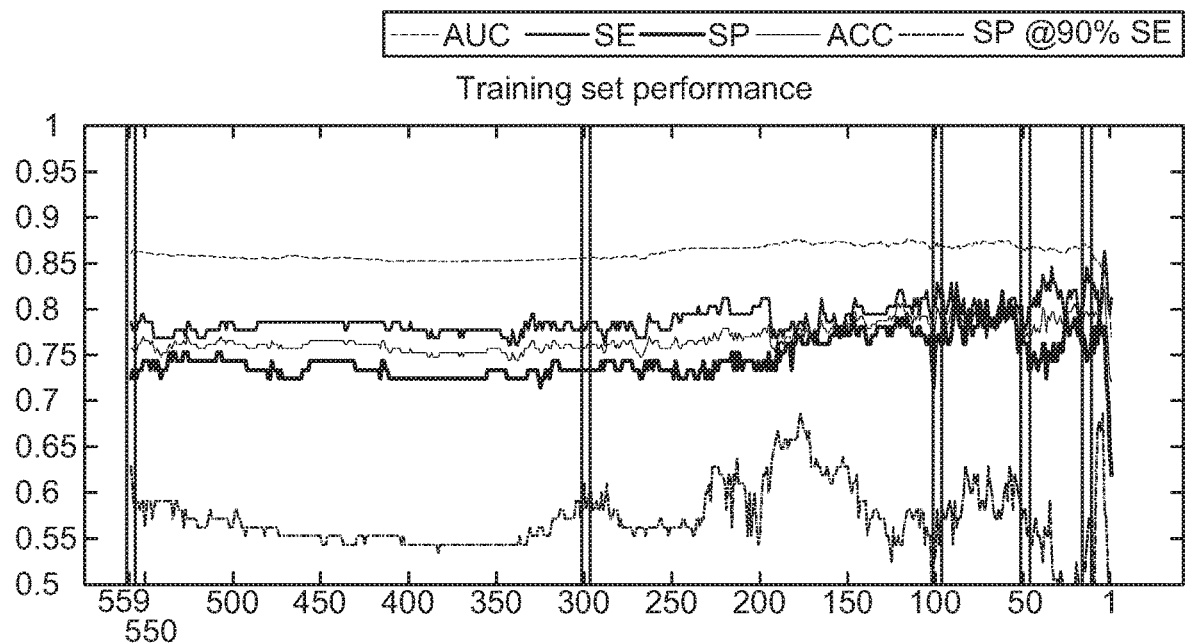
FIG. 1A and FIG. 1B are representative graphs showing performance of Illumina gene expression across different iterations of SVM-RFE process.

The methods and compositions described herein apply gene expression technology to blood screening for the detection and diagnosis of lung cancer. The compositions and methods described herein provide the ability to distinguish a cancerous tumor from a non-cancerous nodule, by determining a characteristic RNA expression profile of the genes of the blood of a mammalian, preferably human, subject. The characteristic gene expression profile is compared with the profile of one or more subjects of the same class (e.g., patients having lung cancer or a non-cancerous nodule) or a control, to see which class the gene expression profile is most similar to, to provide a useful diagnosis.

These methods of lung cancer screening employ compositions suitable for conducting a simple and cost-effective and non-invasive blood test using gene expression profiling that could alert the patient and physician to obtain further studies, such as an additional chest radiograph PET or CT scan, bronchoscopy or biopsy, in much the same way that the prostate specific antigen is used to help diagnose and follow the progress of prostate cancer. The application of these profiles provides overlapping and confirmatory diagnoses of the type of lung disease, beginning with the initial test for malignant vs. non-malignant disease.

"Patient" or "subject" as used herein means a mammalian animal, including a human, a veterinary or farm animal, a domestic animal or pet, and animals normally used for clinical research. In one embodiment, the subject of these methods and compositions is a human.

"Control" or "Control subject" as used herein refers to the source of the reference gene expression profiles as well as the particular panel of control subjects described herein. In one embodiment, the control or reference level is from a single subject. In another embodiment, the control or reference level is from a population of individuals sharing a specific characteristic. In yet another embodiment, the control or reference level is an assigned value which correlates with the level of a specific control individual or population, although not necessarily measured at the time of assaying the test subject's sample. In one embodiment, the control subject or reference is from a patient (or population) having a non-cancerous nodule. In another embodiment, the control subject or reference is from a patient (or population) having a cancerous tumor. In other embodiments, the control subject can be a subject or population with lung cancer, such as a subject who is a current or former smoker with malignant disease, a subject with a solid lung tumor prior to surgery for removal of same; a subject with a solid lung tumor following surgical removal of said tumor; a subject with a solid lung tumor prior to therapy for same; and a subject with a solid lung tumor during or following therapy for same. In other embodiments, the controls for purposes of the compositions and methods described herein include any of the following classes of reference human subject with no lung cancer. Such non-healthy controls (NHC) include the classes of smoker with non-malignant disease, a former smoker with non-malignant disease (including patients with lung nodules), a non-smoker who has chronic obstructive pulmonary disease (COPD), and a former smoker with COPD. In still other embodiments, the control subject is a healthy non-smoker with no disease or a healthy smoker with no disease.

"Sample" as used herein means any biological fluid or tissue that contains immune cells and/or cancer cells. The most suitable sample for use in this invention includes whole blood. Other useful biological samples include, without limitation, peripheral blood mononuclear cells, plasma, saliva, urine, synovial fluid, bone marrow, cerebrospinal fluid, vaginal mucus, cervical mucus, nasal secretions, sputum, semen, amniotic fluid, bronchoscopy sample, bronchoalveolar lavage fluid, nasal brushings and other cellular exudates from a patient having cancer. Such samples may further be diluted with saline, buffer or a physiologically acceptable diluent. Alternatively, such samples are concentrated by conventional means.

As used herein, the term "cancer" refers to or describes the physiological condition in mammals that is typically characterized by unregulated cell growth. More specifically, as used herein, the term "cancer" means any lung cancer. In one embodiment, the lung cancer is non-small cell lung cancer (NSCLC). In a more specific embodiment, the lung cancer is lung adenocarcinoma (AC or LAC). In another more specific embodiment, the lung cancer is lung squamous cell carcinoma (SCC or LSCC). In another embodiment, the lung cancer is a stage I or stage II NSCLC. In still another embodiment, the lung cancer is a mixture of early and late stages and types of NSCLC.

The term "tumor," as used herein, refers to all neoplastic cell growth and proliferation, whether malignant or benign, and all pre-cancerous and cancerous cells and tissues. The term "nodule" refers to an abnormal buildup of tissue which can be malignant or benign. The term "cancerous tumor" refers to a malignant tumor.

By "diagnosis" or "evaluation" it is meant a diagnosis of a lung cancer, a diagnosis of a stage of lung cancer, a diagnosis of a type or classification of a lung cancer, a diagnosis or detection of a recurrence of a lung cancer, a diagnosis or detection of a regression of a lung cancer, a prognosis of a lung cancer, or an evaluation of the response of a lung cancer to a surgical or non-surgical therapy. In one embodiment, "diagnosis" or "evaluation" refers to distinguishing between a cancerous tumor and a benign pulmonary nodule.

As used herein, "sensitivity" (also called the true positive rate), measures the proportion of positives that are correctly identified as such (e.g., the percentage of sick people who are correctly identified as having the condition).

As used herein, "specificity" (also called the true negative rate) measures the proportion of negatives that are correctly identified as such (e.g., the percentage of healthy people who are correctly identified as not having the condition).

By "change in expression" is meant an upregulation of one or more selected genes in comparison to the reference or control; a downregulation of one or more selected genes in comparison to the reference or control; or a combination of certain upregulated genes and down regulated genes.

By "therapeutic reagent" or "regimen" is meant any type of treatment employed in the treatment of cancers with or without solid tumors, including, without limitation, chemotherapeutic pharmaceuticals, biological response modifiers, radiation, diet, vitamin therapy, hormone therapies, gene therapy, surgical resection, etc.

By "informative genes" as used herein is meant those genes the expression of which changes (either in an up-regulated or down-regulated manner) characteristically in the presence of lung cancer. A statistically significant number of such informative genes thus form suitable gene expression profiles for use in the methods and compositions. Such genes are shown in Table I, Table II, Table III, Table IV and Table IX below. Such genes make up the "expression profile".

The term "statistically significant number of genes" in the context of this invention differs depending on the degree of change in gene expression observed. The degree of change in gene expression varies with the type of cancer and with the size or spread of the cancer or solid tumor. The degree of change also varies with the immune response of the individual and is subject to variation with each individual. For example, in one embodiment of this invention, a large change, e.g., 2-3 fold increase or decrease in a small number of genes, e.g., in about 5-8 genes, is statistically significant. In another embodiment, a smaller relative change in about 15 or more genes is statistically significant.

Thus, the methods and compositions described herein contemplate examination of the expression profile of a "statistically significant number of genes" ranging from 5 to about 50 genes in a single profile. In one embodiment, the genes are selected from Table I. In another embodiment, the genes are selected from Table II. In another embodiment, the genes are selected from Table III. In one embodiment, the gene profile is formed by a statistically significant number of 5 or more genes. In one embodiment, the gene profile is formed by a statistically significant number of 7 or more genes. In one embodiment, the gene profile is formed by a statistically significant number of 8 or more genes. In one embodiment, the gene profile is formed by a statistically significant number of 10 or more genes. In another embodiment, the gene profile is formed by a statistically significant number of 15 or more genes. In another embodiment, the gene profile is formed by a statistically significant number of 20 or more genes. In another embodiment, the gene profile is formed by a statistically significant number of 25 or more genes. In another embodiment, the gene profile is formed by a statistically significant number of 30 or more genes. In another embodiment, the gene profile is formed by a statistically significant number of 35 or more genes. In another embodiment, the gene profile is formed by a statistically significant number of 40 or more genes. In another embodiment, the gene profile is formed by a statistically significant number of 41 or more genes. In another embodiment, the gene profile is formed by a statistically significant number of 45 or more genes. In another embodiment, the gene profile is formed by a statistically significant number of 50 or more genes. In another embodiment, the gene profile is formed by 1, 2, 3, 4, 5, 6, 7, or 8 genes of Table I. In another embodiment, the gene profile is formed by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 genes of Table II. In another embodiment, the gene profile is formed by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 genes of Table III. In another embodiment, the gene profile is formed by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 of Table IV. In another embodiment, the gene profile is formed by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 genes of Table IX.

Table I, Table II, Table III, Table IV and Table IX below refer to a collection of known genes useful in discriminating between a subject having a lung cancer, e.g., NSCLC, and subjects having benign (non-malignant) lung nodules. The sequences of the genes identified in Table I, Table II, Table III, Table IV and Table IX are publicly available. One skilled in the art may readily reproduce the compositions and methods described herein by use of the sequences of the genes, all of which are publicly available from conventional sources, such as GenBank. The GenBank accession number for each gene is provided.

The term "microarray" refers to an ordered arrangement of hybridizable array elements, preferably polynucleotide or oligonucleotide probes, on a substrate.

The term "polynucleotide," when used in singular or plural form, generally refers to any polyribonucleotide or polydeoxribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The terms "differentially expressed gene", "differential gene expression" and their synonyms, which are used interchangeably, refer to a gene whose expression is activated to a higher or lower level in a subject suffering from a disease, specifically cancer, such as lung cancer, relative to its expression in a control subject, such as a subject having a benign nodule. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes or their gene products, or a comparison of the ratios of the expression between two or more genes or their gene products, or even a comparison of two differently processed products of the same gene, which differ between normal subjects, non-health controls and subjects suffering from a disease, specifically cancer, or between various stages of the same disease. Differential expression includes both quantitative, as well as qualitative, differences in the temporal or cellular expression pattern in a gene or its expression products among, for example, normal and diseased cells, or among cells which have undergone different disease events or disease stages. For the purpose of this invention, "differential gene expression" is considered to be present when there is a statistically significant ($p<0.05$) difference in gene expression between the subject and control samples.

The term "over-expression" with regard to an RNA transcript is used to refer to the level of the transcript determined by normalization to the level of reference mRNAs, which might be all measured transcripts in the specimen or a particular reference set of mRNAs.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

In the context of the compositions and methods described herein, reference to "7 or more", "at least 7" etc. of the genes listed in Table I, Table II, Table III, Table IV or Table IX means any one or any and all combinations of the genes listed. For example, suitable gene expression profiles include profiles containing any number between at least 7 through 50 genes from Table II. In another example, suitable gene expression profiles include profiles containing any number between at least 8 through 50 genes from Table III. For example, suitable gene expression profiles include profiles containing any number between at least 7 through 100 genes from Table IV. For example, suitable gene expression profiles include profiles containing any number between at least 7 through 41 genes from Table IX. In one embodiment, gene profiles formed by genes selected from a table are used in rank order, e.g., genes ranked in the top of the list demonstrated more significant discriminatory results in the tests, and thus may be more significant in a profile than lower ranked genes. However, in other embodiments the genes forming a useful gene profile do not have to be in rank order and may be any gene from the table. When referring to "Table I, Table II, Table III, Table IV or Table IX" it is also contemplated that combinations thereof can be made to provide a classifier useful herein.

As used herein, "labels" or "reporter molecules" are chemical or biochemical moieties useful for labeling a nucleic acid (including a single nucleotide), polynucleotide, oligonucleotide, or protein ligand, e.g., amino acid or antibody. "Labels" and "reporter molecules" include fluorescent agents, chemiluminescent agents, chromogenic agents, quenching agents, radionucleotides, enzymes, substrates, cofactors, inhibitors, magnetic particles, and other moieties known in the art. "Labels" or "reporter molecules" are capable of generating a measurable signal and may be covalently or noncovalently joined or bound to an oligonucleotide or nucleotide (e.g., a non-natural nucleotide) or ligand.

Unless defined otherwise in this specification, technical and scientific terms used herein have the same meaning as commonly understood by one of ordinary skill in the art to which this invention belongs and by reference to published texts, which provide one skilled in the art with a general guide to many of the terms used in the present application.

I. GENE EXPRESSION PROFILES

The inventors have shown that the gene expression profiles of the whole blood of lung cancer patients differ significantly from those seen in patients having non-cancerous lung nodules. For example, changes in the gene expression products of the genes of Table I, Table II, Table III, Table IV and/or Table IX can be observed and detected by the methods of this invention in the normal circulating blood of patients with early stage solid lung tumors.

The gene expression profiles described herein provide new diagnostic markers for the early detection of lung cancer and could prevent patients from undergoing unnecessary procedures relating to surgery or biopsy for a benign nodule. Since the risks are very low, the benefit to risk ratio is very high. In one embodiment, the methods and compositions described herein may be used in conjunction with clinical risk factors to help physicians make more accurate decisions about how to manage patients with lung nodules. Another advantage of this invention is that diagnosis may occur early since diagnosis is not dependent upon detecting circulating tumor cells which are present in only vanishing small numbers in early stage lung cancers.

In one aspect, a composition is provided for classifying a nodule as cancerous or benign in a mammalian subject. In one embodiment, the composition includes at least 7 polynucleotides or oligonucleotides or ligands, wherein each polynucleotide or oligonucleotide or ligand hybridizes to a different gene, gene fragment, gene transcript or expression product in a sample selected from the genes of Table I, Table II, Table III, Table IV or Table IX. In one embodiment, the genes are the first 7 genes listed in Table IV. In one embodiment, the composition includes at least 8 polynucleotides or oligonucleotides or ligands, wherein each polynucleotide or oligonucleotide or ligand hybridizes to a different gene, gene fragment, gene transcript or expression product in a sample selected from the genes of Table I, Table II, Table III, Table IV or Table IX. In one embodiment, the genes are those in Table I. In another embodiment, the composition includes at least 15 polynucleotides or oligonucleotides or ligands, wherein each polynucleotide or oligonucleotide or ligand hybridizes to a different gene, gene fragment, gene transcript or expression product in a sample selected from the genes of Table II, Table III, Table IV or Table IX. In one embodiment, the genes are the first 15 genes of Table II. In one embodiment, the genes are the first 15 genes of Table III. In one embodiment, the genes are the first 15 genes of Table IV. In one embodiment, the genes are the first 15 genes of Table IX. In another embodiment, the composition includes at least 41 polynucleotides or oligonucleotides or ligands, wherein each polynucleotide or oligonucleotide or ligand hybridizes to a different gene, gene fragment, gene transcript or expression product in a sample selected from the genes of Table II, Table III, Table IV or Table IX. In one embodiment, the genes are the genes of Table IX. In another embodiment, the composition includes at least 50 polynucleotides or oligonucleotides or ligands, wherein each polynucleotide or oligonucleotide or ligand hybridizes to a different gene, gene fragment, gene transcript or expression product in a sample selected from the genes of Table II, Table III, Table IV or Table IX. In one embodiment, the genes are the genes of Table II. In another embodiment, the genes are the genes of Table III. In another embodiment, the genes are the genes of Table IV. In one embodiment, the polynucleotide or oligonucleotide or ligand hybridizes to an mRNA.

TABLE I

| Gene Name | Accession # | T1 Rank | S1 Rank |
|---|---|---|---|
| MERTK | NM_006343.2 | 11 | 3 |
| SLC25A20 | NM_000387.5 | 1 | 6 |
| KYNU | NM_001032998.1 | 15 | 8 |
| P2RY5 | NM_005767.5 | 4 | 14 |
| SNORA56 | NR_002984.1 | 44 | 16 |
| IL1B | NM_000576.2 | 36 | 18 |
| LY96 | NM_015364.4 | 32 | 22 |
| REPIN1 | NM_014374.3 | 38 | 38 |

TABLE II

| Gene Name | Accession # | T1 Rank |
|---|---|---|
| SLC25A20 | NM_000387.5 | 1 |
| CD160 | NM_007053.3 | 2 |
| CCL3 | NM_002983.2 | 3 |
| P2RY5 | NM_005767.5 | 4 |
| CCL3L3 | NM_001001437.3 | 5 |
| PSMA6 | NM_002791.2 | 6 |
| LILRA5 b | NM_181879.2 | 7 |
| CCND3 | NM_001760.2 | 8 |
| LDHA | NM_001165416.1 | 9 |
| NME1-NME2 | NM_001018136.2 | 10 |
| MERTK | NM_006343.2 | 11 |
| CXCR5 b | NM_001716.3 | 12 |
| TAPBP | NM_003190.4 | 13 |
| CAMP | NM_004345.4 | 14 |
| KYNU | NM_001032998.1 | 15 |
| ACAA2 | NM_006111.2 | 16 |
| ANXA1 b | NM_000700.1 | 17 |
| CABC1 | NM_020247.4 | 18 |
| SOCS1 | NM_003745.1 | 19 |
| C4orf27 | NM_017867.2 | 20 |
| SPA17 | NM_017425.3 | 21 |
| MEN1 | NM_130799.2 | 22 |
| MAGEA3 | NM_005362.3 | 23 |
| UBA1 | NM_003334.3 | 24 |
| CLN8 | NM_018941.3 | 25 |
| ETFDH | NM_004453.3 | 26 |
| RHOB | NM_004040.3 | 27 |
| CD160 b | NM_007053.2 | 28 |
| KIR_Activating_Subgroup_2 | NM_014512.1 | 29 |
| PDGFD | NM_033135.3 | 30 |
| HLA-DMB | NM_002118.3 | 31 |
| LY96 | NM_015364.4 | 32 |
| IL16 | NM_004513.4 | 33 |
| DPF2 | NM_006268.4 | 34 |
| RBX1 | NM_014248.3 | 35 |
| IL1B | NM_000576.2 | 36 |
| LOC148137 | NM_144692.1 | 37 |
| REPIN1 | NM_014374.3 | 38 |
| PELP1 | NM_014389.2 | 39 |
| PRG2 | NM_002728.4 | 40 |
| RHOU | NM_021205.5 | 41 |
| C19orf59 | NM_174918.2 | 42 |
| C1orf103 | NM_018372.3 | 43 |
| SNORA56 | NR_002984.1 | 44 |
| IL1R2 | NM_173343.1 | 45 |
| NFATC4 | NM_001136022.2 | 46 |
| ANP32B | NM_006401.2 | 47 |
| C4B | NM_001002029.3 | 48 |
| STOM | NM_004099.5 | 49 |
| LPIN2 | NM_014646.2 | 50 |

TABLE III

| Gene Name | Accession # | S1 Rank |
|---|---|---|
| TBCE | NM_001079515.2 | 1 |
| ITGAL | NM_002209.2 | 2 |
| MERTK | NM_006343.2 | 3 |
| BCOR | NM_017745.5 | 4 |
| GLT25D1 | NM_024656.2 | 5 |
| SLC25A20 | NM_000387.5 | 6 |
| LOC100130229 | XM_001717158.1 | 7 |
| KYNU | NM_001032998.1 | 8 |
| BANP | NM_079837.2 | 9 |
| IGFBP7 | NM_001553.2 | 10 |
| SFRS15 | NM_020706.2 | 11 |
| SH2D3C | NM_170600.2 | 12 |
| DNAJB1 | NM_006145.2 | 13 |
| P2RY5 | NM_005767.5 | 14 |
| PSMB7 | NM_002799.2 | 15 |
| SNORA56 | NR_002984.1 | 16 |
| ATP5L | NM_006476.4 | 17 |
| IL1B | NM_000576.2 | 18 |
| CDC42EP2 | NM_006779.3 | 19 |
| USP34 | NM_014709.3 | 20 |
| AMD1 | NM_001634.4 | 21 |
| LY96 | NM_015364.4 | 22 |
| ARG1 | NM_000045.3 | 23 |
| DGUOK | NM_080916.2 | 24 |
| TNFSF8 | NM_001244.3 | 25 |
| ATG5 | NM_004849.2 | 26 |
| SLC6A6 | NM_003043.5 | 27 |
| FAIM3 | NM_005449.4 | 28 |
| RHOG | NM_001665.3 | 29 |
| CASP1 | NM_033294.3 | 30 |
| PHRF1 | NM_020901.3 | 31 |
| TMBIM6 | NM_003217.2 | 32 |
| FLJ10357 | NM_018071.4 | 33 |
| HSP90AB1 | NM_007355.3 | 34 |
| CDH5 | NM_001795.3 | 35 |
| SNX11 | NM_152244.1 | 36 |
| RERE | NM_001042682.1 | 37 |
| REPIN1 | NM_014374.3 | 38 |
| REPS1 | NM_001128617.2 | 39 |
| RELA | NM_021975.2 | 40 |
| HERC1 | NM_003922.3 | 41 |
| AKAP4 | NM_139289.1 | 42 |
| P2RY10 | NM_198333.1 | 43 |
| HSCB | NM_172002.3 | 44 |
| TRRAP | NM_003496.3 | 45 |
| SETD1B | XM_037523.11 | 46 |
| ARHGAP26 | NM_015071.4 | 47 |
| DYNC2LI1 | NM_016008.3 | 48 |
| TCP1 | NM_030752.2 | 49 |
| DGUOK b | NM_080916.2 | 50 |

TABLE IV

| Rank | Gene Name | Description | Accession # |
|---|---|---|---|
| 1 | SLC25A20 | solute carrier family 25 (carnitine/acylcarnitine translocase), member 20 | NM_000387.5 |
| 2 | CCL3L3 | chemokine (C-C motif) ligand 3-like 3 | NM_001001437.3 |
| 3 | LDHA | lactate dehydrogenase A | NM_001165416.1 |
| 4 | C4orf27 | chromosome 4 open reading frame 27 | NM_017867.2 |
| 5 | RHOU | ras homolog family member U | NM_021205.5 |
| 6 | COMMD6 | COMM domain containing 6 | NM_203497.3 |
| 7 | ZNF143 | zinc finger protein 143 | NM_003442.5 |
| 8 | CASP3 | caspase 3, apoptosis-related cysteine peptidase | NM_032991.2 |
| 9 | P2RY5 | lysophosphatidic acid receptor 6 | NM_005767.5 |
| 10 | ZNF341 | zinc finger protein 341 | NM_032819.4 |
| 11 | CD160 | CD160 molecule | NM_007053.3 |
| 12 | EIF4ENIF1 | eukaryotic translation initiation factor 4E nuclear import factor 1 | NM_019843.2 |
| 13 | LILRA5 b | leukocyte immunoglobulin like receptor A5 | NM_181879.2 |
| 14 | RNF114 | ring finger protein 114 | NM_018683.3 |
| 15 | IL16 | interleukin 16 | NM_004513.4 |
| 16 | REPS1 | RALBP1 associated Eps domain containing 1 | NM_001128617.2 |
| 17 | TMEM70 | transmembrane protein 70 | NM_017866.5 |
| 18 | PRG2 | proteoglycan 2, bone marrow (natural killer cell activator, eosinophil granule major basic protein) | NM_002728.4 |
| 19 | CCR1 | chemokine (C-C motif) receptor 1 | NM_001295.2 |
| 20 | LOC148137 | NA | NM_144692.1 |
| 21 | HOOK3 | hook microtubule-tethering protein 3 | NM_032410.3 |
| 22 | C1orf222 | NA | NM_001003808.1 |
| 23 | KYNU | kynureninase | NM_001032998.1 |
| 24 | CLN8 | ceroid-lipofuscinosis, neuronal 8 (epilepsy, progressive with mental retardation) | NM_018941.3 |
| 25 | PDGFD | platelet derived growth factor D | NM_033135.3 |
| 26 | LOC645914 | NA | XM_928884.1 |
| 27 | SPA17 | sperm autoantigenic protein 17 | NM_017425.3 |
| 28 | MTCH1 | mitochondrial carrier 1 | NM_014341.2 |
| 29 | STOM | stomatin | NM_004099.5 |
| 30 | CCND3 | cyclin D3 | NM_001760.2 |
| 31 | EHD4 | EH-domain containing 4 | NM_139265.3 |
| 32 | IDO1 | indoleamine 2,3-dioxygenase 1 | NM_002164.3 |
| 33 | PPP6C | protein phosphatase 6, catalytic subunit | NM_002721.4 |
| 34 | IL1B | interleukin 1, beta | NM_000576.2 |

TABLE IV-continued

| Rank | Gene Name | Description | Accession # |
|---|---|---|---|
| 35 | SETD2 | SET domain containing 2 | NM_014159.6 |
| 36 | IL1R2 | interleukin 1 receptor, type II | NM_173343.1 |
| 37 | ATP5I | ATP synthase, H+ transporting, mitochondrial Fo complex, subunit E | NM_007100.2 |
| 38 | CTSW | cathepsin W | NM_001335.3 |
| 39 | HNRNPK | heterogeneous nuclear ribonucleoprotein K | NM_031263.2 |
| 40 | NFATC4 | nuclear factor of activated T-cells, cytoplasmic, calcineurin-dependent 4 | NM_001136022.2 |
| 41 | KIAA0101 | KIAA0101 | NM_014736.4 |
| 42 | NME1-NME2 | NME1-NME2 readthrough | NM_001018136.2 |
| 43 | REPIN1 | replication initiator 1 | NM_014374.3 |
| 44 | PELP1 | proline, glutamate and leucine rich protein 1 | NM_014389.2 |
| 45 | FOXK2 | forkhead box K2 | NM_004514.3 |
| 46 | MAGEA1 | melanoma antigen family A, 1 (directs expression of antigen MZ2-E) | NM_004988.4 |
| 47 | HLA-DMB | major histocompatibility complex, class II, DM beta | NM_002118.3 |
| 48 | C17orf51 | chromosome 17 open reading frame 51 | XM_944416.1 |
| 49 | CAMP | cathelicidin antimicrobial peptide | NM_004345.4 |
| 50 | SMARCC1 | SWI/SNF related, matrix associated, actin dependent regulator of chromatin, subfamily c, member 1 | NM_003074.3 |
| 51 | MAGEA3 | melanoma antigen family A, 3 | NM_005362.3 |
| 52 | TTC9 | tetratricopeptide repeat domain 9 | NM_015351.1 |
| 53 | MARCKS | myristoylated alanine-rich protein kinase C substrate | NM_002356.6 |
| 54 | C19orf59 | NA | NM_174918.2 |
| 55 | MEN1 | multiple endocrine neoplasia I | NM_130799.2 |
| 56 | PUM1 | pumilio RNA-binding family member 1 | NM_001020658.1 |
| 57 | USP9Y | ubiquitin specific peptidase 9, Y-linked | NM_004654.3 |
| 58 | PACS1 | phosphofurin acidic cluster sorting protein 1 | NM_018026.3 |
| 59 | S100A8 | S100 calcium binding protein A8 | NM_002964.4 |
| 60 | MBD1 | methyl-CpG binding domain protein 1 | NM_015844.2 |
| 61 | CS | citrate synthase | NM_004077.2 |
| 62 | UBE2G1 | ubiquitin-conjugating enzyme E2G 1 | NM_003342.4 |
| 63 | KIAA1267 | KAT8 regulatory NSL complex subunit 1 | NM_015443.3 |
| 64 | MERTK | MER proto-oncogene, tyrosine kinase | NM_006343.2 |
| 65 | CTAG1B | cancer/testis antigen 1B | NM_001327.2 |
| 66 | CRKL | v-crk avian sarcoma virus CT10 oncogene homolog-like | NM_005207.3 |
| 67 | SYNJ1 | synaptojanin 1 | NM_003895.3 |
| 68 | C4B | complement component 4B (Chido blood group) | NM_001002029.3 |
| 69 | SOCS1 | suppressor of cytokine signaling 1 | NM_003745.1 |
| 70 | NUP153 | nucleoporin 153 kDa | NM_005124.3 |
| 71 | COLEC12 | collectin sub-family member 12 | NM_130386.2 |
| 72 | TAPBP | TAP binding protein (tapasin) | NM_003190.4 |
| 73 | IFI27L2 | interferon, alpha-inducible protein 27-like 2 | NM_032036.2 |
| 74 | RBX1 | ring-box 1, E3 ubiquitin protein ligase | NM_014248.3 |
| 75 | CR2 b | complement C3d receptor 2 | NM_001006658.1 |
| 76 | C1orf103 | NA | NM_018372.3 |
| 77 | TBCE | tubulin folding cofactor E | NM_001079515.2 |
| 78 | CCL3 | chemokine (C-C motif) ligand 3 | NM_002983.2 |
| 79 | LOC100129022 | NA | XM_001716591.1 |
| 80 | NCAPG | non-SMC condensin I complex, subunit G | NM_022346.4 |
| 81 | FLNB | filamin B, beta | NM_001457.3 |
| 82 | C3 | complement component 3 | NM_000064.2 |
| 83 | SAP130 b | Sin3A associated protein 130 | NM_024545.3 |
| 84 | CD160 b | CD160 molecule | NM_007053.2 |
| 85 | STAG3 | stromal antigen 3 | NM_012447.3 |
| 86 | SFPQ | splicing factor proline/glutamine-rich | NM_005066.2 |
| 87 | ITCH | itchy E3 ubiquitin protein ligase | NM_001257138.1 |
| 88 | HSCB | HscB mitochondrial iron-sulfur cluster co-chaperone | NM_172002.3 |
| 89 | TFCP2 | transcription factor CP2 | NM_005653.4 |
| 90 | LIF | leukemia inhibitory factor | NM_002309.3 |
| 91 | BATF | basic leucine zipper transcription factor, ATF-like | NM_006399.3 |
| 92 | SNORA56 | small nucleolar RNA, H/ACA box 56 | NR_002984.1 |
| 93 | ETFDH | electron-transferring-flavoprotein dehydrogenase | NM_004453.3 |
| 94 | BCL10 | B-cell CLL/lymphoma 10 | NM_003921.2 |

TABLE IV-continued

| Rank | Gene Name | Description | Accession # |
|---|---|---|---|
| 95 | TIAM1 | T-cell lymphoma invasion and metastasis 1 | NM_003253.2 |
| 96 | MPDU1 | mannose-P-dolichol utilization defect 1 | NM_004870.3 |
| 97 | TRIM39 | tripartite motif containing 39 | NM_021253.3 |
| 98 | RNF34 | ring finger protein 34, E3 ubiquitin protein ligase | NM_025126.3 |
| 99 | AMD1 | adenosylmethionine decarboxylase 1 | NM_001634.4 |
| 100 | PSMA6 | proteasome (prosome, macropain) subunit, alpha type, 6 | NM_002791.2 |

TABLE IX

41 Gene Classifier

| | |
|---|---|
| 1 | SLC25A20 |
| 2 | P2RY5 |
| 3 | DNAJB1 |
| 4 | CCND3 |
| 5 | CD160 |
| 6 | MERTK |
| 7 | BCOR |
| 8 | ABCA5 |
| 9 | RNASE2 |
| 10 | IGFBP7 |
| 11 | ITGAL |
| 12 | DYNC2LI1 |
| 13 | EEF1B2 |
| 14 | RAG1 |
| 15 | DDIT4 |
| 16 | ARG1 |
| 17 | TBC1D12 |
| 18 | AZI2 |
| 19 | LOC100130229 |
| 20 | STOM |
| 21 | MED16 |
| 22 | EMR4 |
| 23 | REPIN1 |
| 24 | DNAJB6 |
| 25 | IDO1 |
| 26 | PSMB7 |
| 27 | HSP90AB1 |
| 28 | CABC1 |
| 29 | PRPF3 |
| 30 | PSMB8 |
| 31 | TRIM39 |
| 32 | CD48 |
| 33 | CDH5 |
| 34 | KLRC1 |
| 35 | TUG1 |
| 36 | PIM2 |
| 37 | CLPTM1 |
| 38 | REPS1 |
| 39 | USP9Y |
| 40 | AFTPH |
| 41 | SLC6A12 |

In one embodiment, a novel gene expression profile or signature can identify and distinguish patients having cancerous tumors from patients having benign nodules. See for example the genes identified in Table I, Table II, Table III, Table IV and Table IX which may form a suitable gene expression profile. In another embodiment, a portion of the genes of Table I form a suitable profile. In yet another embodiment, a portion of the genes of Table II form a suitable profile. In yet another embodiment, a portion of the genes of Table III form a suitable profile. In yet another embodiment, a portion of the genes of Table IV form a suitable profile. In yet another embodiment, a portion of the genes of Table IX form a suitable profile. As discussed herein, these profiles are used to distinguish between cancerous and non-cancerous tumors by generating a discriminant score based on differences in gene expression profiles as exemplified below. The validity of these signatures was established on samples collected at different locations by different groups in a cohort of patients with undiagnosed lung nodules. See the Examples and FIGS. 1 and 2. The lung cancer signatures or gene expression profiles identified herein (i.e., Table I, Table II, Table III, Table IV or Table IX) may be further optimized to reduce the numbers of gene expression products necessary and increase accuracy of diagnosis.

In one embodiment, the composition includes about 7 or polynucleotides or oligonucleotides or ligands, wherein each polynucleotide or oligonucleotide or ligand hybridizes to a different gene, gene fragment, gene transcript or expression product in a sample selected from the genes of Table I, Table II Table III, Table IV or Table IX. In another embodiment, the composition includes about 5 to about 50 polynucleotides or oligonucleotides or ligands, wherein each polynucleotide or oligonucleotide or ligand hybridizes to a different gene, gene fragment, gene transcript or expression product in a sample selected from the genes of Table II. In another embodiment, the composition includes about 5 to about 50 polynucleotides or oligonucleotides or ligands, wherein each polynucleotide or oligonucleotide or ligand hybridizes to a different gene, gene fragment, gene transcript or expression product in a sample selected from the genes of Table III. In another embodiment, the composition includes about 5 to about 50 polynucleotides or oligonucleotides or ligands, wherein each polynucleotide or oligonucleotide or ligand hybridizes to a different gene, gene fragment, gene transcript or expression product in a sample selected from the genes of Table IV. In another embodiment, the composition includes 1, 2, 3, 4, 5, 6, 7, or 8 polynucleotides or oligonucleotides or ligands, wherein each polynucleotide or oligonucleotide or ligand hybridizes to a different gene, gene fragment, gene transcript or expression product in a sample selected from the genes of Table I. In another embodiment, the composition includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 polynucleotides or oligonucleotides or ligands, wherein each polynucleotide or oligonucleotide or ligand hybridizes to a different gene, gene fragment, gene transcript or expression product in a sample selected from the genes of Table II. In another embodiment, the composition includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 polynucleotides or oligonucleotides or ligands, wherein each polynucleotide or oligonucleotide or ligand hybridizes to a different gene, gene fragment, gene transcript or expression product in a sample selected from the genes of Table III. In another embodiment, the composition includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 polynucleotides or oligonucleotides or ligands, wherein each polynucleotide or oligonucleotide or ligand hybridizes to a different gene, gene fragment, gene transcript or expression product in a sample selected from the genes of Table IV. In another embodiment, the composition includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides or oligonucleotides or ligands, wherein each polynucleotide or oligonucleotide or ligand hybridizes to a different gene, gene fragment, gene transcript or expression product in a sample selected from the genes of Table IX. In one embodiment, the composition includes at least 3 polynucleotides or oligonucleotides or ligands, wherein each polynucleotide or oligonucleotide or ligand hybridizes to a different gene, gene fragment, gene transcript or expression product in a sample selected from the genes of Table 1, Table II, Table III, Table IV or Table IX. In one embodiment, the composition includes at least 5 polynucleotides or oligonucleotides or ligands, wherein each polynucleotide or oligonucleotide or ligand hybridizes to a different gene, gene fragment, gene transcript or expression product in a sample selected from the genes of Table I, Table II, Table III, Table IV or Table IX. In one embodiment, the composition includes at least 7 polynucleotides or oligonucleotides or ligands, wherein each polynucleotide or oligonucleotide or ligand hybridizes to a different gene, gene fragment, gene transcript or expression product in a sample selected from the genes of Table I, Table II, Table III, Table IV or Table IX. In one embodiment, the composition includes at least 8 polynucleotides or oligonucleotides or ligands, wherein each polynucleotide or oligonucleotide or ligand hybridizes to a different gene, gene fragment, gene transcript or expression product in a sample selected from the genes of Table I, Table II, Table III, Table IV or Table IX. In one embodiment, the composition includes at least 10 polynucleotides or oligonucleotides or ligands, wherein each polynucleotide or oligonucleotide or ligand hybridizes to a different gene, gene fragment, gene transcript or expression product in a sample selected from the genes of Table II, Table III, Table IV or Table IX. In one embodiment, the composition includes at least 15 polynucleotides or oligonucleotides or ligands, wherein each polynucleotide or oligonucleotide or ligand hybridizes to a different gene, gene fragment, gene transcript or expression product in a sample selected from the genes of Table II, Table III, Table IV or Table IX. In one embodiment, the composition includes at least 20 polynucleotides or oligonucleotides or ligands, wherein each polynucleotide or oligonucleotide or ligand hybridizes to a different gene, gene fragment, gene transcript or expression product in a sample selected from the genes of Table II, Table III, Table IV or Table IX. In one embodiment, the composition includes at least 25 polynucleotides or oligonucleotides or ligands, wherein each polynucleotide or oligonucleotide or ligand hybridizes to a different gene, gene fragment, gene transcript or expression product in a sample selected from the genes of Table II, Table III, Table IV or Table IX. In one embodiment, the composition includes at least 30 polynucleotides or oligonucleotides or ligands, wherein each polynucleotide or oligonucleotide or ligand hybridizes to a different gene, gene fragment, gene transcript or expression product in a sample selected from the genes of Table II, Table III, Table IV or Table IX. In one embodiment, the composition includes at least 35 polynucleotides or oligonucleotides or ligands, wherein each polynucleotide or oligonucleotide or ligand hybridizes to a different gene, gene fragment, gene transcript or expression product in a sample selected from the genes of Table II, Table III, Table IV or Table IX. In one embodiment, the composition includes at least 40 polynucleotides or oligonucleotides or ligands, wherein each polynucleotide or oligonucleotide or ligand hybridizes to a different gene, gene fragment, gene transcript or expression product in a sample selected from the genes of Table II, Table III, Table IV or Table IX. In one embodiment, the composition includes at least 45 polynucleotides or oligonucleotides or ligands, wherein each polynucleotide or oligonucleotide or ligand hybridizes to a different gene, gene fragment, gene transcript or expression product in a sample selected from the genes of Table II, Table III, Table IV or Table IX. In one embodiment, the composition includes at least 50 polynucleotides or oligonucleotides or ligands, wherein each polynucleotide or oligonucleotide or ligand hybridizes to a different gene, gene fragment, gene transcript or expression product in a sample selected from the genes of Table II, Table III, Table IV or Table IX. In one embodiment, the composition includes at least 55 polynucleotides or oligonucleotides or ligands, wherein each polynucleotide or oligonucleotide or ligand hybridizes to a different gene, gene fragment, gene transcript or expression product in a sample selected from the genes of Table IV. In one embodiment, the composition includes at least 60 polynucleotides or oligonucleotides or ligands, wherein each polynucleotide or oligonucleotide or ligand hybridizes to a different gene, gene fragment, gene transcript or expression product in a sample selected from the genes of Table IV. In one embodiment, the composition includes at least 65 polynucleotides or oligonucleotides or ligands, wherein each polynucleotide or oligonucleotide or ligand hybridizes to a different gene, gene fragment, gene transcript or expression product in a sample selected from the genes of Table IV. In one embodiment, the composition includes at least 70 polynucleotides or oligonucleotides or ligands, wherein each polynucleotide or oligonucleotide or ligand hybridizes to a different gene, gene fragment, gene transcript or expression product in a sample selected from the genes of Table IV. In one embodiment, the composition includes at least 75 polynucleotides or oligonucleotides or ligands, wherein each polynucleotide or oligonucleotide or ligand hybridizes to a different gene, gene fragment, gene transcript or expression product in a sample selected from the genes of Table IV. In one embodiment, the composition includes at least 80 polynucleotides or oligonucleotides or ligands, wherein each polynucleotide or oligonucleotide or ligand hybridizes to a different gene, gene fragment, gene transcript or expression product in a sample selected from the genes of Table IV. In one embodiment, the composition includes at least 85 polynucleotides or oligonucleotides or ligands, wherein each polynucleotide or oligonucleotide or ligand hybridizes to a different gene, gene fragment, gene transcript or expression product in a sample selected from the genes of Table IV. In one embodiment, the composition includes at least 90 polynucleotides or oligonucleotides or ligands, wherein each polynucleotide or oligonucleotide or ligand hybridizes to a different gene, gene fragment, gene transcript or expression product in a sample selected from the genes of Table IV. In one embodiment, the composition includes at least 95 polynucleotides or oligonucleotides or ligands, wherein each polynucleotide or oligonucleotide or ligand hybridizes to a different gene, gene fragment, gene transcript or expression product in a sample selected from the genes of Table IV. In one embodiment, the composition includes at least 100 polynucleotides or oligonucleotides or ligands, wherein each polynucleotide or oligonucleotide or ligand hybridizes to a different gene, gene fragment, gene transcript or expression product in a sample selected from the genes of Table IV.

In yet another embodiment, the expression profile is formed by the first 3 genes in rank order of Table I, Table II, Table III, Table IV or Table IX. In yet another embodiment, the expression profile is formed by the first 5 genes in rank order of Table I, Table II, Table III, Table IV or Table IX. In yet another embodiment, the expression profile is formed by the first 8 genes in rank order of Table I, Table II, Table III, Table IV or Table IX. In yet another embodiment, the expression profile is formed by the first 15 genes in rank order of Table II, Table III, Table IV or Table IX. In yet another embodiment, the expression profile is formed by the first 20 genes in rank order of Table II, Table III, Table IV or Table IX. In another embodiment, the expression profile is formed by the first 25 genes in rank order of Table II, Table III, Table IV or Table IX. In yet another embodiment, the expression profile is formed by the first 30 genes in rank order of Table II, Table III, Table IV or Table IX. In another embodiment, the expression profile is formed by the first 35 genes in rank order of Table II, Table III, Table IV or Table IX. In another embodiment, the expression profile is formed by the first 40 genes in rank order of Table II, Table III, Table IV or Table IX. In another embodiment, the expression profile is formed by the first 41 genes in rank order of Table II, Table III, Table IV or Table IX. In another embodiment, the expression profile is formed by the first 45 genes in rank order of Table II, Table III, or Table IV. In yet another embodiment, the expression profile is formed by the first 50 genes in rank order of Table II, Table III, or Table IV. In yet another embodiment, the expression profile is formed by the first 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 genes in rank order of Table IV.

As discussed below, the compositions described herein can be used with the gene expression profiling methods which are known in the art. Thus, the compositions can be adapted accordingly to suit the method for which they are intended to be used. In one embodiment, at least one polynucleotide or oligonucleotide or ligand is attached to a detectable label. In certain embodiments, each polynucleotide or oligonucleotide is attached to a different detectable label, each capable of being detected independently. Such reagents are useful in assays such as the nCounter, as described below, and with the diagnostic methods described herein.

In another embodiment, the composition comprises a capture oligonucleotide or ligand, which hybridizes to at least one polynucleotide or oligonucleotide or ligand. In one embodiment, such capture oligonucleotide or ligand may include a nucleic acid sequence which is specific for a portion of the oligonucleotide or polynucleotide or ligand which is specific for the gene of interest. The capture ligand may be a peptide or polypeptide which is specific for the ligand to the gene of interest. In one embodiment, the capture ligand is an antibody, as in a sandwich ELISA.

The capture oligonucleotide also includes a moiety which allows for binding with a substrate. Such substrate includes, without limitation, a plate, bead, slide, well, chip or chamber. In one embodiment, the composition includes a capture oligonucleotide for each different polynucleotide or oligonucleotide which is specific to a gene of interest. Each capture oligonucleotide may contain the same moiety which allows for binding with the same substrate. In one embodiment, the binding moiety is biotin.

Thus, a composition for such diagnosis or evaluation in a mammalian subject as described herein can be a kit or a reagent. For example, one embodiment of a composition includes a substrate upon which the ligands used to detect and quantitate mRNA are immobilized. The reagent, in one embodiment, is an amplification nucleic acid primer (such as an RNA primer) or primer pair that amplifies and detects a nucleic acid sequence of the mRNA. In another embodiment, the reagent is a polynucleotide probe that hybridizes to the target sequence. In another embodiment, the target sequences are illustrated in Table III. In another embodiment, the reagent is an antibody or fragment of an antibody. The reagent can include multiple said primers, probes or antibodies, each specific for at least one gene, gene fragment or expression product of Table I, Table II, Table III, Table IV or Table IX. Optionally, the reagent can be associated with a conventional detectable label.

In another embodiment, the composition is a kit containing the relevant multiple polynucleotides or oligonucleotide probes or ligands, optional detectable labels for same, immobilization substrates, optional substrates for enzymatic labels, as well as other laboratory items. In still another embodiment, at least one polynucleotide or oligonucleotide or ligand is associated with a detectable label. In certain embodiments, the reagent is immobilized on a substrate. Exemplary substrates include a microarray, chip, microfluidics card, or chamber.

In one embodiment, the composition is a kit designed for use with the nCounter Nanostring system, as further discussed below.

II. GENE EXPRESSION PROFILING METHODS

Methods of gene expression profiling that were used in generating the profiles useful in the compositions and methods described herein or in performing the diagnostic steps using the compositions described herein are known and well summarized in U.S. Pat. No. 7,081,340. Such methods of gene expression profiling include methods based on hybridization analysis of polynucleotides, methods based on sequencing of polynucleotides, and proteomics-based methods. The most commonly used methods known in the art for the quantification of mRNA expression in a sample include northern blotting and in situ hybridization; RNAse protection assays; nCounter® Analysis; and PCR-based methods, such as RT-PCR. Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

In certain embodiments, the compositions described herein are adapted for use in the methods of gene expression profiling and/or diagnosis described herein, and those known in the art.

A. Patient Sample

The "sample" or "biological sample" as used herein means any biological fluid or tissue that contains immune cells and/or cancer cells. In one embodiment, a suitable sample is whole blood. In another embodiment, the sample may be venous blood. In another embodiment, the sample may be arterial blood. In another embodiment, a suitable sample for use in the methods described herein includes peripheral blood, more specifically peripheral blood mononuclear cells. Other useful biological samples include, without limitation, plasma or serum. In still other embodiment, the sample is saliva, urine, synovial fluid, bone marrow, cerebrospinal fluid, vaginal mucus, cervical mucus, nasal secretions, nasal brushings, sputum, semen, amniotic fluid, bronchoalveolar lavage fluid, and other cellular exudates from a subject suspected of having a lung disease. Such samples may further be diluted with saline, buffer or a physiologically acceptable diluent. Alternatively, such samples are concentrated by conventional means. It should be understood that the use or reference throughout this specification to any one biological sample is exemplary only. For example, where in the specification the sample is referred to as whole blood, it is understood that other samples, e.g., serum, plasma, etc., may also be employed in another embodiment.

In one embodiment, the biological sample is whole blood, and the method employs the PaxGene Blood RNA Workflow system (Qiagen). That system involves blood collection (e.g., single blood draws) and RNA stabilization, followed by transport and storage, followed by purification of Total RNA and Molecular RNA testing. This system provides immediate RNA stabilization and consistent blood draw volumes. The blood can be drawn at a physician's office or clinic, and the specimen transported and stored in the same tube. Short term RNA stability is 3 days at between 18-25° C. or 5 days at between 2-8° C. Long term RNA stability is 4 years at −20 to −70° C. This sample collection system enables the user to reliably obtain data on gene expression in whole blood. In one embodiment, the biological sample is whole blood. While the PAXgene system has more noise than the use of PBMC as a biological sample source, the benefits of PAXgene sample collection outweighs the problems. Noise can be subtracted bioinformatically by the person of skill in the art.

In one embodiment, the biological samples may be collected using the proprietary PaxGene Blood RNA System (PreAnalytiX, a Qiagen, BD company). The PAXgene Blood RNA System comprises two integrated components: PAXgene Blood RNA Tube and the PAXgene Blood RNA Kit. Blood samples are drawn directly into PAXgene Blood RNA Tubes via standard phlebotomy technique. These tubes contain a proprietary reagent that immediately stabilizes intracellular RNA, minimizing the ex-vivo degradation or up-regulation of RNA transcripts. The ability to eliminate freezing, batch samples, and to minimize the urgency to process samples following collection, greatly enhances lab efficiency and reduces costs. Thereafter, the miRNA is detected and/or measured using a variety of assays.

B. Nanostring Analysis

A sensitive and flexible quantitative method that is suitable for use with the compositions and methods described herein is the nCounter® Analysis system (NanoString Technologies, Inc., Seattle WA). The nCounter Analysis System utilizes a digital color-coded barcode technology that is based on direct multiplexed measurement of gene expression and offers high levels of precision and sensitivity (<1 copy per cell). The technology uses molecular "barcodes" and single molecule imaging to detect and count hundreds of unique transcripts in a single reaction. Each color-coded barcode is attached to a single target-specific probe (i.e., polynucleotide, oligonucleotide or ligand) corresponding to a gene of interest, i.e., a gene of Table I, Table II, Table III, Table IV or Table IX. Mixed together with controls, they form a multiplexed CodeSet. In one embodiment, the CodeSet includes all 8 genes of Table I. In one embodiment, the CodeSet includes the first 7 genes of Table II, Table III, Table IV or Table IX. In another embodiment, the CodeSet includes all 50 genes of Table II. In another embodiment, the CodeSet includes all 50 genes of Table III. In another embodiment, the CodeSet includes at least 3 genes of Table I, Table II, Table III, Table IV or Table IX. In another embodiment, the CodeSet includes at least 5 genes of Table I, Table II, Table III, Table IV or Table IX. In another embodiment, the CodeSet includes at least 8 genes of Table I, Table II, Table III, Table IV or Table IX. In another embodiment, the CodeSet includes at least 10 genes of Table II, Table III, Table IV or Table IX. In another embodiment, the CodeSet includes at least 15 genes of Table II, Table III, Table IV or Table IX. In another embodiment, the CodeSet includes at least 20 genes of Table II, Table III, Table IV or Table IX. In another embodiment, the CodeSet includes at least 25 genes of Table II, Table III, Table IV or Table IX. In another embodiment, the CodeSet includes at least 30 genes of Table II, Table III, Table IV or Table IX. In yet another embodiment, the CodeSet includes at least 40 genes of Table II, Table III, Table IV or Table IX. In yet another embodiment, the CodeSet includes at least 41 genes of Table II, Table III, Table IV or Table IX. In yet another embodiment, the CodeSet includes at least 50 genes of Table II, Table III, Table IV or Table IX. In another embodiment, the CodeSet includes at least 60 genes of Table III, Table IV or Table IX. In another embodiment, the CodeSet includes at least 70 genes of Table III, Table IV or Table IX. In yet another embodiment, the CodeSet includes at least 80 genes of Table III, Table IV or Table IX. In yet another embodiment, the CodeSet includes at least 90 genes of Table III, Table IV or Table IX. In another embodiment, the CodeSet includes all 100 genes of Table III, Table IV or Table IX. In yet another embodiment, the CodeSet includes any subset of genes of Table I, Table II, Table III, Table IV or Table IX, including combinations thereof, as described herein.

The NanoString platform employs two ~50 base probes per mRNA that hybridizes in solution. The Reporter Probe carries the signal; the Capture Probe allows the complex to be immobilized for data collection. The probes are mixed with the patient sample. After hybridization, the excess probes are removed, and the probe/target complexes aligned and immobilized to a substrate, e.g., in the nCounter Cartridge.

The target sequences utilized in the Examples below for each of the genes of Table I, Table II, Table III, Table IV and Table IX are shown in Table V below, and are reproduced in the sequence listing. These sequences are portions of the published sequences of these genes. Suitable alternatives may be readily designed by one of skill in the art.

Sample Cartridges are placed in the Digital Analyzer for data collection. Color codes on the surface of the cartridge are counted and tabulated for each target molecule.

A benefit of the use of the NanoString nCounter system is that no amplification of mRNA is necessary in order to perform the detection and quantification. However, in alternate embodiments, other suitable quantitative methods are used. See, e.g., Geiss et al, Direct multiplexed measurement of gene expression with color-coded probe pairs, Nat Biotechnol. 2008 March; 26(3):317-25. doi: 10.1038/nbt1385. Epub 2008 Feb. 17, which is incorporated herein by reference in its entirety.

C. Polymerase Chain Reaction (PCR) Techniques

Another suitable quantitative method is RT-PCR, which can be used to compare mRNA levels in different sample populations, in normal and tumor tissues, to characterize patterns of gene expression, to discriminate between closely related mRNAs, and to analyze RNA structure. The first step is the isolation of mRNA from a target sample (e.g., typically total RNA isolated from human PBMC). mRNA can be extracted, for example, from frozen or archived paraffin-embedded and fixed (e.g. formalin-fixed) tissue samples.

General methods for mRNA extraction are well known in the art, such standard textbooks of molecular biology. In particular, RNA isolation can be performed using a purification kit, buffer set and protease from commercial manufacturers, according to the manufacturer's instructions. Exemplary commercial products include TRI-REAGENT, Qiagen RNeasy mini-columns, MASTERPURE Complete DNA and RNA Purification Kit (EPICENTRE®, Madison, Wis.), Paraffin Block RNA Isolation Kit (Ambion, Inc.) and RNA Stat-60 (Tel-Test). Conventional techniques such as cesium chloride density gradient centrifugation may also be employed.

The first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. See, e.g., manufacturer's instructions accompanying the product GENEAMP RNA PCR kit (Perkin Elmer, Calif., USA). The derived cDNA can then be used as a template in the subsequent RT-PCR reaction.

The PCR step generally uses a thermostable DNA-dependent DNA polymerase, such as the Taq DNA polymerase, which has a 5'-3' nuclease activity but lacks a 3'-5' proofreading endonuclease activity. Thus, TAQMAN® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. In one embodiment, the target sequence is shown in Table V. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment. In a preferred embodiment, the 5' nuclease procedure is run on a real-time quantitative PCR device such as the ABI PRISM 7900@ Sequence Detection System®. The system amplifies samples in a 96-well format on a thermocycler. During amplification, laser-induced fluorescent signal is collected in real-time through fiber optic cables for all 96 wells, and detected at the CCD. The system includes software for running the instrument and for analyzing the data. 5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle ($C_t$).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

Real time PCR is comparable both with quantitative competitive PCR, where internal competitor for each target sequence is used for normalization, and with quantitative comparative PCR using a normalization gene contained within the sample, or a housekeeping gene for RT-PCR.

In another PCR method, i.e., the MassARRAY-based gene expression profiling method (Sequenom, Inc., San Diego, CA), following the isolation of RNA and reverse transcription, the obtained cDNA is spiked with a synthetic DNA molecule (competitor), which matches the targeted cDNA region in all positions, except a single base, and serves as an internal standard. The cDNA/competitor mixture is PCR amplified and is subjected to a post-PCR shrimp alkaline phosphatase (SAP) enzyme treatment, which results in the dephosphorylation of the remaining nucleotides. After inactivation of the alkaline phosphatase, the PCR products from the competitor and cDNA are subjected to primer extension, which generates distinct mass signals for the competitor- and cDNA-derived PCR products. After purification, these products are dispensed on a chip array, which is pre-loaded with components needed for analysis with matrix-assisted laser desorption ionization time-of-flight mass spectrometry (MALDI-TOF MS) analysis. The cDNA present in the reaction is then quantified by analyzing the ratios of the peak areas in the mass spectrum generated.

Still other embodiments of PCR-based techniques which are known to the art and may be used for gene expression profiling include, e.g., differential display, amplified fragment length polymorphism (iAFLP), and BeadArray™ technology (Illumina, San Diego, CA) using the commercially available Luminex100 LabMAP system and multiple color-coded microspheres (Luminex Corp., Austin, Tex.) in a rapid assay for gene expression; and high coverage expression profiling (HiCEP) analysis.

D. Microarrays

Differential gene expression can also be identified, or confirmed using the microarray technique. Thus, the expression profile of lung cancer-associated genes can be measured in either fresh or paraffin-embedded tissue, using microarray technology. In this method, polynucleotide sequences of interest (including cDNAs and oligonucleotides) are plated, or arrayed, on a microchip substrate. The arrayed sequences are then hybridized with specific DNA probes from cells or tissues of interest. Just as in the other methods and compositions herein, the source of mRNA is total RNA isolated from whole blood of controls and patient subjects.

In one embodiment of the microarray technique, PCR amplified inserts of cDNA clones are applied to a substrate in a dense array. In one embodiment, all 559 nucleotide sequences from Table III are applied to the substrate. The microarrayed genes, immobilized on the microchip, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels. Microarray analysis can be performed by commercially available equipment, following manufacturer's protocols.

Other useful methods summarized by U.S. Pat. No. 7,081,340, and incorporated by reference herein include Serial Analysis of Gene Expression (SAGE) and Massively Parallel Signature Sequencing (MPSS). Briefly, serial analysis of gene expression (SAGE) is a method that allows the simultaneous and quantitative analysis of a large number of gene transcripts, without the need of providing an individual hybridization probe for each transcript. First, a short sequence tag (about 10 to 14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., Science 270:484 487 (1995); and Velculescu et al., Cell 88:243 51 (1997), both of which are incorporated herein by reference.

Gene Expression Analysis by Massively Parallel Signature Sequencing (MPSS), described by Brenner et al., Nature Biotechnology 18:630 634 (2000) (which is incorporated herein by reference), is a sequencing approach that combines non-gel-based signature sequencing with in vitro cloning of millions of templates on separate 5 µm diameter microbeads. First, a microbead library of DNA templates is constructed by in vitro cloning. This is followed by the assembly of a planar array of the template-containing microbeads in a flow cell at a high density (typically greater than $3 \times 10^6$ microbeads/cm$^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

E. Immunohistochemistry

Immunohistochemistry methods are also suitable for detecting the expression levels of the gene expression products of the informative genes described for use in the methods and compositions herein. Antibodies or antisera, preferably polyclonal antisera, and most preferably monoclonal antibodies, or other protein-binding ligands specific for each marker are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Protocols and kits for immunohistochemical analyses are well known in the art and are commercially available.

III. COMPOSITIONS OF THE INVENTION

The methods for diagnosing lung cancer described herein which utilize defined gene expression profiles permit the development of simplified diagnostic tools for diagnosing lung cancer, e.g., NSCLC vs. non-cancerous nodule. Thus, a composition for diagnosing lung cancer in a mammalian subject as described herein can be a kit or a reagent. For example, one embodiment of a composition includes a substrate upon which said polynucleotides or oligonucleotides or ligands or ligands are immobilized. In another embodiment, the composition is a kit containing the relevant 5 or more polynucleotides or oligonucleotides or ligands, optional detectable labels for same, immobilization substrates, optional substrates for enzymatic labels, as well as other laboratory items. In still another embodiment, at least one polynucleotide or oligonucleotide or ligand is associated with a detectable label.

In one embodiment, a composition for diagnosing lung cancer in a mammalian subject includes 7 or more PCR primer-probe sets. Each primer-probe set amplifies a different polynucleotide sequence from a gene expression product of 7 or more informative genes found in the blood of the subject. These informative genes are selected to form a gene expression profile or signature which is distinguishable between a subject having lung cancer and a subject having a non-cancerous nodule. Changes in expression in the genes in the gene expression profile from that of a reference gene expression profile are correlated with a lung cancer, such as non-small cell lung cancer (NSCLC).

In one embodiment of this composition, the informative genes are selected from among the genes identified in Table I. In another embodiment of this composition, the informative genes are selected from among the genes identified in Table II. In another embodiment of this composition, the informative genes are selected from among the genes identified in Table III. In another embodiment of this composition, the informative genes are selected from among the genes identified in Table IV. In another embodiment of this composition, the informative genes are selected from among the genes identified in Table IX. This collection of genes is those for which the gene product expression is altered (i.e., increased or decreased) versus the same gene product expression in the blood of a reference control (i.e., a patient having a non-cancerous nodule). In one embodiment, polynucleotide or oligonucleotide or ligands, i.e., probes, are generated to 7 or more informative genes from Table I, Table II, Table III, Table IV and/or Table IX for use in the composition (the CodeSet). An example of such a composition contains probes to a targeted portion of the genes of Table I. In another embodiment, probes are generated to all 8 genes from Table I for use in the composition. In another embodiment, probes are generated to the first 15 genes from Table II for use in the composition. In another embodiment, probes are generated to the first 15 genes from Table III for use in the composition. In another embodiment, probes are generated to the first 41 genes from Table IX for use in the composition. In another embodiment, probes are generated to the 50 genes from Table II for use in the composition. In another embodiment, probes are generated to the 50 genes from Table III for use in the composition. In another embodiment, probes are generated the first 7 genes from Table IV for use in the composition. In another embodiment, probes are generated the first 15 genes from Table I for use in the composition. In another embodiment, probes are generated the first 50 genes from Table IV for use in the composition. In another embodiment, probes are generated to the first 3 genes from Table I, Table II, Table III, Table IV or Table IX for use in the composition. In another embodiment, probes are generated to the first 5 genes from Table I, Table II, Table III, Table IV or Table IX for use in the composition. In another embodiment, probes are generated to the first 10 genes from Table II, Table III, Table IV or Table IX for use in the composition. In another embodiment, probes are generated to the first 15 genes from Table II, Table III, Table IV or Table IX for use in the composition. In another embodiment, probes are generated to the first 20 genes from Table II, Table III, Table IV or Table IX for use in the composition. In another embodiment, probes are generated to the first 25 genes from Table II, Table III, Table IV or Table IX for use in the composition. In yet another embodiment, probes are generated to the first 30 genes from Table II, Table III, Table IV or Table IX for use in the composition. In yet another embodiment, probes are generated to the first 35 genes from Table II, Table III, Table IV or Table IX for use in the composition. In yet another embodiment, probes are generated to the first 40 genes from Table II, Table III, Table IV or Table IX for use in the composition. In yet another embodiment, probes are generated to the first 45 genes from Table II, Table III, Table IV or Table IX for use in the composition. In yet another embodiment, probes are generated to the first 50 genes from Table II, Table III, Table IV or Table IX for use in the composition. In yet another embodiment, probes are generated to the first 55, 60, 65, 70, 75, 80, 85, 90, 95 or 100 genes from Table IV for use in the composition. The selected genes from the Tables need not be in rank order; rather any combination that clearly shows a difference in expression between the reference control to the diseased patient is useful in such a composition.

In one embodiment of the compositions described above, the reference control is a non-healthy control (NHC) as described above. In other embodiments, the reference control may be any class of controls as described above in "Definitions".

The compositions based on the genes selected from Table I, Table II, Table III, Table IV or Table IX described herein, optionally associated with detectable labels, can be presented in the format of a microfluidics card, a chip or chamber, or a kit adapted for use with the Nanostring, PCR, RT-PCR or Q PCR techniques described above. In one aspect, such a format is a diagnostic assay using TAQMAN® Quantitative PCR low density arrays. In another aspect, such a format is a diagnostic assay using the Nanostring nCounter platform.

For use in the above-noted compositions the PCR primers and probes are preferably designed based upon intron sequences present in the gene(s) to be amplified selected from the gene expression profile. Exemplary target sequences are shown in Table IV. The design of the primer and probe sequences is within the skill of the art once the particular gene target is selected. The particular methods selected for the primer and probe design and the particular primer and probe sequences are not limiting features of these compositions. A ready explanation of primer and probe design techniques available to those of skill in the art is summarized in U.S. Pat. No. 7,081,340, with reference to publically available tools such as DNA BLAST software, the Repeat Masker program (Baylor College of Medicine), Primer Express (Applied Biosystems); MGB assay-by-design (Applied Biosystems); Primer3 (Steve Rozen and Helen J. Skaletsky (2000) Primer3 on the WWW for general users and for biologist programmers.

In general, optimal PCR primers and probes used in the compositions described herein are generally 17-30 bases in length, and contain about 20-80%, such as, for example, about 50-60% G+C bases. Melting temperatures of between 5° and 80° C., e.g. about 50 to 70° C. are typically preferred.

In another aspect, a composition for diagnosing lung cancer in a mammalian subject contains a plurality of polynucleotides immobilized on a substrate, wherein the plurality of genomic probes hybridize to 8 or more gene expression products of 8 or more informative genes selected from a gene expression profile in the blood of the subject, the gene expression profile comprising genes selected from Table I, Table II, Table III, Table IV or Table IX. In another aspect, a composition for diagnosing lung cancer in a mammalian subject contains a plurality of polynucleotides immobilized on a substrate, wherein the plurality of genomic probes hybridize to 8 or more gene expression products of 8 or more informative genes selected from a gene expression profile in the blood of the subject, the gene expression profile comprising genes selected from Table I, Table II, Table III, Table IV or Table IX. In another embodiment, a composition for diagnosing lung cancer in a mammalian subject contains a plurality of polynucleotides immobilized on a substrate, wherein the plurality of genomic probes hybridize to 15 or more gene expression products of 15 or more informative genes selected from a gene expression profile in the blood of the subject, the gene expression profile comprising genes selected from Table II, Table III, Table IV or Table IX. This type of composition relies on recognition of the same gene profiles as described above for the Nanostring compositions but employs the techniques of a cDNA array. Hybridization of the immobilized polynucleotides in the composition to the gene expression products present in the blood of the patient subject is employed to quantitate the expression of the informative genes selected from among the genes identified in Table I, Table II, Table III, Table IV and Table IX to generate a gene expression profile for the patient, which is then compared to that of a reference sample. As described above, depending upon the identification of the profile (i.e., that of genes of Table I or subsets thereof, that of genes of Table II or subsets thereof, that of genes of Table III or subsets thereof, that of genes of Table IV or subsets thereof), this composition enables the diagnosis and prognosis of NSCLC lung cancers. Again, the selection of the polynucleotide sequences, their length and labels used in the composition are routine determinations made by one of skill in the art in view of the teachings of which genes can form the gene expression profiles suitable for the diagnosis and prognosis of lung cancers.

In yet another aspect, a composition or kit useful in the methods described herein contain a plurality of ligands that bind to 7 or more gene expression products of 7 or more informative genes selected from a gene expression profile in the blood of the subject. In another embodiment, a composition or kit useful in the methods described herein contain a plurality of ligands that bind to 8 or more gene expression products of 8 or more informative genes selected from a gene expression profile in the blood of the subject. The gene expression profile contains the genes of Table I, Table II, Table III, Table IV or Table IX, as described above for the other compositions. In another embodiment, a composition or kit useful in the methods described herein contain a plurality of ligands that bind to 15 or more gene expression products of 15 or more informative genes selected from a gene expression profile in the blood of the subject. The gene expression profile contains the genes of Table I, Table II, Table III, Table IV or Table IX, as described above for the other compositions. In another embodiment, a composition or kit useful in the methods described herein contain a plurality of ligands that bind to 50 or more gene expression products of 50 or more informative genes selected from a gene expression profile in the blood of the subject. The gene expression profile contains the genes of Table I, Table II, Table III, Table IV or Table IX, as described above for the other compositions. This composition enables detection of the proteins expressed by the genes in the indicated Tables. While preferably the ligands are antibodies to the proteins encoded by the genes in the profile, it would be evident to one of skill in the art that various forms of antibody, e.g., polyclonal, monoclonal, recombinant, chimeric, as well as fragments and components (e.g., CDRs, single chain variable regions, etc.) may be used in place of antibodies. Such ligands may be immobilized on suitable substrates for contact with the subject's blood and analyzed in a conventional fashion. In certain embodiments, the ligands are associated with detectable labels. These compositions also enable detection of changes in proteins encoded by the genes in the gene expression profile from those of a reference gene expression profile. Such changes correlate with lung cancer in a manner similar to that for the PCR and polynucleotide-containing compositions described above.

For all of the above forms of diagnostic/prognostic compositions, the gene expression profile can, in one embodiment, include at least the first 7 or 8 of the informative genes of Table II, Table III, Table IV or Table IX. In another embodiment for all of the above forms of diagnostic/prognostic compositions, the gene expression profile can, in one embodiment, include at least the first 15 of the informative genes of Table II, Table III, Table IV or Table IX. In another embodiment for all of the above forms of diagnostic/prognostic compositions, the gene expression profile can include 50 or more of the informative genes of Table II, Table III, Table IV or Table IX. In another embodiment for all of the above forms of diagnostic/prognostic compositions, the gene expression profile can include 20 or more of the informative genes of Table II, Table III, Table IV or Table IX. In another embodiment for all of the above forms of diagnostic/prognostic compositions, the gene expression profile can include 30 or more of the informative genes of Table II, Table III, Table IV or Table IX. In another embodiment for all of the above forms of diagnostic/prognostic compositions, the gene expression profile can include 40 or more of the informative genes of Table II, Table III, Table IV or Table IX. In another embodiment for all of the above forms of diagnostic/prognostic compositions, the gene expression profile can include 50 or more of the informative genes of Table II, Table III, Table IV or Table IX. In another embodiment for all of the above forms of diagnostic/prognostic compositions, the gene expression profile can include 60 or more of the informative genes of Table IV. In another embodiment for all of the above forms of diagnostic/prognostic compositions, the gene expression profile can include 70 or more of the informative genes of Table IV. In another embodiment for all of the above forms of diagnostic/prognostic compositions, the gene expression profile can include 80 or more of the informative genes of Table IV. In another embodiment for all of the above forms of diagnostic/prognostic compositions, the gene expression profile can include 90 or more of the informative genes of Table IV. In another embodiment for all of the above forms of diagnostic/prognostic compositions, the gene expression profile can include all 100 of the informative genes of Tables IV.

These compositions may be used to diagnose lung cancers, such as stage I or stage II NSCLC. Further these compositions are useful to provide a supplemental or original diagnosis in a subject having lung nodules of unknown etiology.

IV. DIAGNOSTIC METHODS OF THE INVENTION

All of the above-described compositions provide a variety of diagnostic tools which permit a blood-based, non-invasive assessment of disease status in a subject. Use of these compositions in diagnostic tests, which may be coupled with other screening tests, such as a chest X-ray or CT scan, increase diagnostic accuracy and/or direct additional testing.

Thus, in one aspect, a method is provided for diagnosing lung cancer in a mammalian subject. This method involves identifying a gene expression profile in the blood of a mammalian, preferably human, subject. In one embodiment, the gene expression profile includes 7, 8, 15, 41, 50 or more gene expression products of 7, 8, 15, 41, 50 or more informative genes having increased or decreased expression in lung cancer. The gene expression profiles are formed by selection of 7, 8, 15, 41, 50 or more informative genes from the genes of Table I, Table II, Table III, Table IV or Table IX. In another embodiment, the gene expression profile includes 7 or more gene expression products of 7 or more informative genes having increased or decreased expression in lung cancer. The gene expression profiles are formed by selection of 7 or more informative genes from the genes of Table I, Table II, Table III, Table IV or Table IX. In one embodiment, the genes are the first 7 genes of Table IV. In another embodiment, the genes are the first 15 genes of Table IV. In another embodiment, the genes are the first 50 genes of Table IV. In another embodiment, the gene expression profiles are formed by selection of 15 or more informative genes from the genes of Table II, Table III, Table IV or Table IX. Comparison of a subject's gene expression profile with a reference gene expression profile permits identification of changes in expression of the informative genes that correlate with a lung cancer (e.g., NSCLC). This method may be performed using any of the compositions described above. In one embodiment, the method enables the diagnosis of a cancerous tumor from a benign nodule.

In another aspect, use of any of the compositions described herein is provided for diagnosing lung cancer in a subject.

The diagnostic compositions and methods described herein provide a variety of advantages over current diagnostic methods. Among such advantages are the following. As exemplified herein, subjects with cancerous tumors are distinguished from those with benign nodules. These methods and compositions provide a solution to the practical diagnostic problem of whether a patient who presents at a lung clinic with a small nodule has malignant disease. Patients with an intermediate-risk nodule would clearly benefit from a non-invasive test that would move the patient into either a very low-likelihood or a very high-likelihood category of disease risk. An accurate estimate of malignancy based on a genomic profile (i.e. estimating a given patient has a 90% probability of having cancer versus estimating the patient has only a 5% chance of having cancer) would result in fewer surgeries for benign disease, more early stage tumors removed at a curable stage, fewer follow-up CT scans, and reduction of the significant psychological costs of worrying about a nodule. The economic impact would also likely be significant, such as reducing the current estimated cost of additional health care associated with CT screening for lung cancer, i.e., $116,000 per quality adjusted life-year gained. A non-invasive blood genomics test that has a sufficient sensitivity and specificity would significantly alter the post-test probability of malignancy and thus, the subsequent clinical care.

A desirable advantage of these methods over existing methods is that they are able to characterize the disease state from a minimally-invasive procedure, i.e., by taking a blood sample. In contrast, current practice for classification of cancer tumors from gene expression profiles depends on a tissue sample, usually a sample from a tumor. In the case of very small tumors a biopsy is problematic and clearly if no tumor is known or visible, a sample from it is impossible. No purification of tumor is required, as is the case when tumor samples are analyzed. A recently published method depends on brushing epithelial cells from the lung during bronchoscopy, a method which is also considerably more invasive than taking a blood sample. Blood samples have an additional advantage, which is that the material is easily prepared and stabilized for later analysis, which is important when messenger RNA is to be analyzed.

The 7, 8, 15, 41, 50 and 100 gene classifiers described herein performed similarly to a 559 marker classifier previously reported by the inventors. See examples and Table VII below. For example, a classifier consisting of the first 50 genes of Table IV performed similarly to a classifier consisting of 559 genes. These compositions and methods allow for more accurate diagnosis and treatment of lung cancer. Thus, in one embodiment, the methods described include treatment of the lung cancer. Treatment may removal of the neoplastic growth, chemotherapy and/or any other treatment known in the art or described herein.

In one embodiment, a method for diagnosing the existence or evaluating a lung cancer in a mammalian subject is provided, which includes identifying changes in the expression of 7, 8, 15, 41, 50 or more genes in the sample of said subject, said genes selected from the genes of Table I, Table Ii, Table III, Table IV or Table IX. The subject's gene expression levels are compared with the levels of the same genes in a reference or control, wherein changes in expression of the subject's genes from those of the reference correlates with a diagnosis or evaluation of a lung cancer.

In one embodiment, the diagnosis or evaluation comprise one or more of a diagnosis of a lung cancer, a diagnosis of a benign nodule, a diagnosis of a stage of lung cancer, a diagnosis of a type or classification of a lung cancer, a diagnosis or detection of a potential recurrence of a lung cancer, a diagnosis or detection of a regression of a lung cancer, a prognosis of a lung cancer, or an evaluation of the response of a lung cancer to a surgical or non-surgical therapy. In another embodiment, the changes comprise an upregulation of one or more selected genes in comparison to said reference or control or a downregulation of one or more selected genes in comparison to said reference or control.

In another embodiment, the reference or control comprises three or more genes of Table I sample of at least one reference subject. The reference subject may be selected from the group consisting of: (a) a smoker with malignant disease, (b) a smoker with non-malignant disease, (c) a former smoker with non-malignant disease, (d) a healthy non-smoker with no disease, (e) a non-smoker who has chronic obstructive pulmonary disease (COPD), (f) a former smoker with COPD, (g) a subject with a solid lung tumor prior to surgery for removal of same; (h) a subject with a solid lung tumor following surgical removal of said tumor; (i) a subject with a solid lung tumor prior to therapy for same; and (j) a subject with a solid lung tumor during or following therapy for same. In one embodiment, the reference or control subject (a)-(j) is the same test subject at a temporally earlier timepoint.

The sample is selected from those described herein. In one embodiment, the sample is peripheral blood. The nucleic acids in the sample are, in some embodiments, stabilized prior to identifying changes in the gene expression levels. Such stabilization may be accomplished, e.g., using the Pax Gene system, described herein.

In one embodiment, the method of detecting lung cancer in a patient includes
 a. obtaining a sample from the patient; and
 b. detecting a change in expression in at least 7 genes selected from Table I, Table II, Table III, Table IV or Table IX in the patient sample as compared to a control by contacting the sample with a composition comprising oligonucleotides, polynucleotides or ligands specific for each different gene transcript or expression product of the at least 7 gene of Table I, Table II, Table III, Table IV or Table IX and detecting binding between the oligonucleotide, polynucleotide or ligand and the gene product or expression product.

In another embodiment, the method of diagnosing lung cancer in a subject includes
 a. obtaining a blood sample from a subject;
 b. detecting a change in expression in at least 7 genes selected from Table I, Table II, Table III, Table IV or Table IX in the patient sample as compared to a control by contacting the sample with a composition comprising oligonucleotides, polynucleotides or ligands specific for each different gene transcript or expression product of the at least 7 gene of Table I, Table II, Table III, Table IV or Table IX and detecting binding between the oligonucleotide, polynucleotide or ligand and the gene product or expression product; and
 c. diagnosing the subject with cancer when changes in expression of the subject's genes from those of the reference are detected.

In yet another embodiment, the method includes
 a. obtaining a blood sample from a subject;
 b. detecting a change in expression in at least 7 genes selected from Table I, Table II, Table III, Table IV or Table IX in the patient sample as compared to a control by contacting the sample with a composition comprising oligonucleotides, polynucleotides or ligands specific for each different gene transcript or expression product of the at least 7 genes of Table I, Table II, Table III, Table IV or Table IX and detecting binding between the oligonucleotide, polynucleotide or ligand and the gene product or expression product;
 c. diagnosing the subject with cancer when changes in expression of the subject's genes from those of the reference are detected; and
 d. removing the neoplastic growth.

V. EXAMPLES

The invention is now described with reference to the following examples. These examples are provided for the purpose of illustration only and the invention should in no way be construed as being limited to these examples but rather should be construed to encompass any and all variations that become evident as a result of the teaching provided herein.

Example 1: Patient Population—Analysis A

For development of the gene classifier described herein, blood samples and clinical information were collected from various subjects, some having a diagnosis of lung cancer and some having a diagnosis of benign nodule, as identified in the table below. Patient characteristics are shown in Table VI below.

Patients diagnosed with either benign or malignant lung recruited from 5 hospitals: Christiana Care Health System, New York University Langone Medical Center, The Hospital of the University of Pennsylvania, Roswell Park and Temple University Hospital. Subjects were being assessed for the presence of lung cancer by LDCT or Chest X-Ray or were incidentally diagnosed with lung nodules. The study population of high-risk individuals were >50 years of age and with >20 pack-years of smoking.

The "control" cohort was derived from patients with benign lung nodules (e.g. ground glass opacities, single nodules, granulomas or hamartomas). These patients were evaluated at pulmonary clinics, or underwent thoracic surgery for a lung nodule. All samples were collected prior to surgery, biopsy, bronchoscopy or nodules were classified as non-cancer after at least 2 years of imaging follow-up with no detectable change in size.

As noted below, T1: samples run on microarray to select genes for NanoString Platform; V1: NYU sample validation set used in NanoString paper; and S1: Full set of "clean" samples not used in microarray to select genes (includes V1).

TABLE VI

|  | Ti | | V1 | | Si | |
| --- | --- | --- | --- | --- | --- | --- |
|  | MN | BN | MN | BN | MN | BN |
| Total | 117 | 105 | 40 | 134 | 182 | 232 |
| Sex |  |  |  |  |  |  |
| Female | 65 | 52 | 19 | 65 | 93 | 120 |
| Male | 52 | 53 | 14 | 68 | 81 | 111 |
| Unknown | 0 | 0 | 7 | 1 | 8 | 1 |
| Age | 67 ± 7 | 65 ± 7 | 68 ± 7 | 62 ± 7 | 68 ± 7 | 62 ± 7 |
| Race |  |  |  |  |  |  |
| Black | 18 | 11 | 4 | 7 | 20 | 13 |
| White | 95 | 90 | 22 | 116 | 121 | 191 |
| Other | 4 | 4 | 14 | 11 | 41 | 28 |
| Smoking Status |  |  |  |  |  |  |
| Current | 31 | 35 | 6 | 52 | 41 | 84 |
| Former | 79 | 65 | 21 | 73 | 122 | 137 |
| Never | 7 | 5 | 6 | 8 | 11 | 10 |
| Unknown | 0 | 0 | 7 | 1 | 8 | 1 |
| Pack Years | 40 ± 22 | 39 ± 15 | 27 ± 27 | 40 ± 15 | 39 ± 21 | 41 ± 15 |
| Site |  |  |  |  |  |  |
| HFGCC | 59 | 17 | 0 | 0 | 57 | 10 |
| FCCC | 0 | 0 | 0 | 0 | 2 | 1 |
| NYU | 21 | 57 | 40 | 134 | 58 | 195 |
| Oncocyte | 0 | 0 | 0 | 0 | 22 | 1 |
| Roswell | 0 | 0 | 0 | 0 | 18 | 19 |
| Temple | 2 | 9 | 0 | 0 | 0 | 1 |
| Upenn | 35 | 22 | 0 | 0 | 25 | 5 |
| Size (mm) | 22 ± 8 | 9 ± 4 | 15 ± 3 | 6 ± 2 | 20 ± 9 | 6 ± 2 |
| Stage |  |  |  |  |  |  |
| 1 | 86 (75%) |  | 22 (55%) |  | 92 (50%) |  |
| 2 | 22 (19%) |  | 7 (18%) |  | 16 (8%) |  |

TABLE VI-continued

|  | Ti | | V1 | | Si | |
| --- | --- | --- | --- | --- | --- | --- |
|  | MN | BN | MN | BN | MN | BN |
| Total | 117 | 105 | 40 | 134 | 182 | 232 |
| 3 | 7 (6%) |  | 11 (28%) |  | 49 (26%) |  |
| 4 | 0 |  | 0 |  | 1 (0%) |  |
| Unknown | 2 |  | 0 |  | 24 (12%) |  |

Example 2: Sample Collection Protocols and Processing

Blood samples were collected in the clinic by the tissue acquisition technician. Blood samples were drawn directly into PAXgene Blood RNA Tubes via standard phlebotomy technique. These tubes contain a proprietary reagent that immediately stabilizes intracellular RNA, minimizing the ex-vivo degradation or up-regulation of RNA transcripts. The ability to eliminate freezing, batch samples, and to minimize the urgency to process samples following collection, greatly enhances lab efficiency and reduces costs.

Example 3—RNA Purification and Quality Assessment

PAXgene RNA is prepared using a standard commercially available kit from Qiagen™ that allows purification of mRNA and miRNA. The resulting total RNA is used for mRNA profiling. The RNA quality is determined using a Bioanalyzer. Only samples with RNA Integrity numbers >3 were used on the nCounter.

Briefly, RNA is isolated as follows. Turn shaker-incubator on and set to 55° C. before beginning. Unless otherwise noted, all steps in this protocol including centrifugation steps, should be carried out at room temp (15-25° C.). This protocol assumes samples are stores at −80° C. Unfrozen samples that have been left a RT per the Qiagen protocol of a minimum of 2 hours should be processed in the same way.

Thaw Paxgene tubes upright in a plastic rack. Invert tubes at least 10 times to mix before starting isolation. Prepare all necessary tubes. For each sample, the following are needed: 2 numbered 1.5 ml Eppendorf tubes; 1 Eppendorf tube with the sample information (this is the final tube); 1 Lilac Paxgene spin column; 1 Red Paxgene Spin column; and 5 Processing tubes.

Centrifuge the PAXgene Blood RNA Tube for 10 minutes at 5000×g using a swing-out rotor in Qiagen centrifuge. (Sigma 4-15° C. Centrifuge., Rotor: Sigma Nr. 11140, 7/01, 5500/min, Holder: Sigma 13115.286 g 14/D, Inside tube holder: 18010, 125 g). Note: After thawed, ensure that the blood sample has been incubated in the PAXgene Blood RNA Tube for a minimum of 2 hours at room temperature (15-25° C.), in order to achieve complete lysis of blood cells.

Under the hood—remove the supernatant by decanting into bleach. When the supernatant is decanted, take care not to disturb the pellet, and dry the rim of the tube with a clean paper towel. Discard the decanted supernatant by placing the clotted blood into a bag and then into the infectious waste and discard the fluid portion down the sink and wash down with a lot of water. Add 4 ml RNase-free water to the pellet, and close the tube using a fresh secondary Hemogard closure.

Vortex until the pellet is visibly dissolved. Weigh the tubes in the centrifuge holder again to ensure they are balanced, and centrifuge for 10 minutes at 5000×g using a swing-out rotor Qiagen centrifuge. Small debris remaining in the supernatant after vortexing but before centrifugation will not affect the procedure.

Remove and discard the entire supernatant. Leave tube upside-down for 1 min to drain off all supernatant. Incomplete removal of the supernatant will inhibit lysis and dilute the lysate, and therefore affect the conditions for binding RNA to the PAXgene membrane.

Add 350 µl Buffer BMI and pipet up and down lyse the pellet.

Pipet the re-suspended sample into a labeled 1.5 ml microcentrifuge tube. Add 300 µl Buffer BM2. Then add 40 µl proteinase K. Mix by vortexing for 5 seconds, and incubate for 10 minutes at 55° C. using a shaker-incubator at the highest possible speed, 800 rpm on Eppendorf thermomixer. (If using a shaking water bath instead of a thermomixer, quickly vortex the samples every 2-3 minutes during the incubation. Keep the vortexer next to the incubator).

Pipet the lysate directly into a PAXgene Shredder spin column (lilac tube) placed in a 2 ml processing tube, and centrifuge for 3 minutes at 24 C at 18,500×g in the TOMY Microtwin centrifuge. Carefully pipet the lysate into the spin column and visually check that the lysate is completely transferred to the spin column. To prevent damage to columns and tubes, do not exceed 20,000×g.

Carefully transfer the entire supernatant of the flow-through fraction to a fresh 1.5 ml microcentrifuge tube without disturbing the pellet in the processing tube. Discard the pellet in the processing tube.

Add 700 µl isopropanol (100%) to the supernatant. Mix by vortexing.

Pipet 690 µl sample into the PAXgene RNA spin column (red) placed in a 2 ml processing tube, and centrifuge for 1 minute at 10,000×g. Place the spin column in a new 2 ml processing tube, and discard the old processing tube containing flow-through.

Pipet the remaining sample into the PAXgene RNA spin column (red), and centrifuge for 1 minute at 18,500×g. Place the spin column in a new 2 ml processing tube, and discard the old processing tube containing flow-through. Carefully pipet the sample into the spin column and visually check that the sample is completely transferred to the spin column.

Pipet 350 µl Buffer BM3 into the PAXgene RNA spin column. Centrifuge for 15 sec at 10,000×g. Place the spin column in a new 2 ml processing tube, and discard the old processing tube containing flow-through.

Prepare DNase I incubation mix for step 13. Add 10 µl DNase I stock solution to 70 µl Buffer RDD in a 1.5 ml microcentrifuge tube. Mix by gently flicking the tube, and centrifuge briefly to collect residual liquid from the sides of the tube.

Pipet the DNase I incubation mix (80 µl) directly onto the PAXgene RNA spin column membrane, and place on the benchtop (20-30° C.) for 15 minutes. Ensure that the DNase I incubation mix is placed directly onto the membrane. DNase digestion will be incomplete if part of the mix is applied to and remains on the walls or the O-ring of the spin column.

Pipet 350 µl Buffer BM3 into the PAXgene RNA spin column, and centrifuge for 15 sec at 18,500×g. Place the spin column in a new 2 ml processing tube, and discard the old processing tube containing flow-through.

Pipet 500 µl Buffer BM4 to the PAXgene RNA spin column, and centrifuge for 15 sec at 10,000×g. Place the spin column in a new 2 ml processing tube, and discard the old processing tube containing flow-through.

Add another 500 µl Buffer BM4 to the PAXgene RNA spin column. Centrifuge for 2 minutes at 18,500×g.

Discard the tube containing the flow-through, and place the PAXgene RNA spin column in a new 2 ml processing tube. Centrifuge for 1 minute at 18,500×g.

Discard the tube containing the flow-through. Place the PAXgene RNA spin column in a labeled 1.5 ml microcentrifuge tube (final tube), and pipet 40 µl Buffer BR5 directly onto the PAXgene RNA spin column membrane. Centrifuge for 1 minute at 10,000×g to elute the RNA. It is important to wet the entire membrane with Buffer BR5 in order to achieve maximum elution efficiency.

Repeat the elution step as described, using 40 µl Buffer BR5 and the same microcentrifuge tube. Centrifuge for 1 minute at 20,000×g to elute the RNA.

Incubate the eluate for 5 minutes at 65° C. in the shaker-incubator without shaking. After incubation, chill immediately on ice. This incubation at 65° C. denatures the RNA for downstream applications. Do not exceed the incubation time or temperature.

If the RNA samples will not be used immediately, store at −20° C. or −70° C. Since the RNA remains denatured after repeated freezing and thawing, it is not necessary to repeat the incubation at 65° C.

Example 4: Measurement of RNA Levels

To provide a biomarker signature that can be used in clinical practice to diagnose lung cancer, a gene expression profile with the smallest number of genes that maintain satisfactory accuracy is provided by the use of 8 more of the genes identified in Table I as well as by the use of 15 or more of the genes identified in Table II, Table III, Table IV or Table IX, or 7 or more genes identified in Table IV. These gene profiles or signatures permit simpler and more practical tests that are easy to use in a standard clinical laboratory. Because the number of discriminating genes is small enough, NanoString nCounter® platforms are developed using these gene expression profiles.

A. Nanostring nCounter® Platform Gene Expression Assay Protocol

Total RNA was isolated from whole blood using the Paxgene Blood miRNA Kit, as described above, and samples were checked for RNA quality. Samples were analyzed with the Agilent 2100 Bioanalyzer on a RNA Nano chip, using the RIN score and electropherogram picture as indicators for good sample integrity. Samples were also quantitated on the Nanodrop (ND-1000 Spectrophotometer) where 260/280 and 260/230 readings were recorded and evaluated for Nanostring-compatibility. From the concentrations taken by Nanodrop, total RNA samples were normalized to contain 100 ng in 5 µL, using Nuclease-free water as diluent, into Nanostring-provided tube strips. An 8 µL aliquot of a mixture of the Nanostring nCounter Reporter CodeSet and Hybridization Buffer (70 µL Hybridization Buffer, 42 µL Reporter CodeSet per 12 assays) and 2 µL of Capture ProbeSet was added to each 5 µL RNA sample. Samples were hybridized for 19 hours at 65° C. in the Thermocycler (Eppendorf). During hybridization, Reporter Probes, which have fluorescent barcodes specific to each mRNA of interest to the user, and biotinylated Capture Probes bound to their associated target mRNA to create target-probe complexes. After hybridization was complete, samples were then transferred to the nCounter Prep Station for processing using the Standard Protocol setting (Run Time: 2 hr 35 min). The Prep Station robot, during the Standard Protocol, washed samples to remove excess Reporter and Capture Probes. Samples were moved to a streptavidin-coated cartridge where purified target-probe complexes were immobilized in preparation for imaging by the nCounter Digital Analyzer. Upon completion, the cartridge was sealed and placed in the Digital Analyzer using a Field of View (FOV) setting at 555. A fluorescent microscope tabulated the raw counts for each unique barcode associated with a target mRNA. Data collected was stored in .csv files and then transferred to the Bioinformatics Facility for analysis according to the manufacturer's instructions.

Example 5: Biomarker Selection

Support Vector Machine (SVM) can be applied to gene expression datasets for gene function discovery and classification. SVM has been found to be most efficient at distinguishing the more closely related cases and controls that reside in the margins. Primarily SVM-RFE (48, 54) was used to develop gene expression classifiers which distinguish clinically defined classes of patients from clinically defined classes of controls (smokers, non-smokers, COPD, granuloma, etc). SVM-RFE is a SVM based model utilized in the art that removes genes, recursively based on their contribution to the discrimination, between the two classes being analyzed. The lowest scoring genes by coefficient weights were removed and the remaining genes were scored again and the procedure was repeated until only a few genes remained. This method has been used in several studies to perform classification and gene selection tasks. However, choosing appropriate values of the algorithm parameters (penalty parameter, kernel-function, etc.) can often influence performance.

SVM-RCE is a related SVM based model, in that it, like SVM-RFE assesses the relative contributions of the genes to the classifier. SVM-RCE assesses the contributions of groups of correlated genes instead of individual genes. Additionally, although both methods remove the least important genes at each step, SVM-RCE scores and removes clusters of genes, while SVM-RFE scores and removes a single or small numbers of genes at each round of the algorithm.

The SVM-RCE method is briefly described here. Low expressing genes (average expression less than 2× background) were removed, quantile normalization performed, and then "outlier" arrays whose median expression values differ by more than 3 sigma from the median of the dataset were removed. The remaining samples were subject to SVM-RCE using ten repetitions of 10-fold cross-validation of the algorithm. The genes were reduced by t-test (applied on the training set) to an experimentally determined optimal value which produces highest accuracy in the final result. These starting genes were clustered by K-means into clusters of correlated genes whose average size is 3-5 genes. SVM classification scoring was carried out on each cluster using 3-fold resampling repeated 5 times, and the worst scoring clusters eliminated. Accuracy is determined on the surviving pool of genes using the left-out 10% of samples (testing set) and the top-scoring 100 genes were recorded. The procedure was repeated from the clustering step to an end point of 2 clusters. The optimal gene panel was taken to be the minimal number of genes which gives the maximal accuracy starting with the most frequently selected gene. The identity of the individual genes in this panel is not fixed, since the order reflects the number of times a given gene was selected in the top 100 informative genes and this order is subject to some variation.

A. Biomarker Selection.

Genes which score highest (by SVM) in discriminating cancerous tumors from benign nodules were examined for their utility for clinical tests. Factors considered include, higher differences in expression levels between classes, and low variability within classes. When selecting biomarkers for validation an effort was made to select genes with distinct expression profiles to avoid selection of correlated genes and to identify genes with differential expression levels that were robust by alternative techniques including PCR and/or immuno-histochemistry.

B. Validation.

Three methods of validation were considered.

Cross-Validation: To minimize over-fitting within a dataset, K-fold cross-validation (K usually equal to 10) was used, when the dataset is split on K parts randomly and K-1 parts were used for training and 1 for testing. Thus, for K=10 the algorithm was trained on a random selection of 90% of the patients and 90% of the controls and then tested on the remaining 10%. This was repeated until all of the samples have been employed as test subjects and the cumulated classifier makes use of all of the samples, but no sample is tested using a training set of which it is a part. To reduce the randomization impact, K-fold separation was performed M times producing different combinations of patients and controls in each of K folds each time. Therefore, for individual dataset M*K rounds of permuted selection of training and testing sets were used for each set of genes.

Independent Validation: To estimate the reproducibility of the data and the generality of the classifier, one needs to examine the classifier that was built using one dataset and tested using another dataset to estimate the performance of the classifier. To estimate the performance, validation on the second set was performed using the classifier developed with the original dataset.

Further Validation: In order to test the generality of a classifier developed in this manner, it was used to classify independent sets of samples that were not used in developing the classifier. The cross-validation accuracies of the permuted and original classifier were compared on independent test sets to confirm its validity in classifying new samples.

C. Classifier Performance

Performance of each classifier was estimated by different methods and several performance measurements were used for comparing classifiers between each other. These measurements include accuracy, area under ROC curve, sensitivity, specificity, true positive rate and true negative rate. Based on the required properties of the classification of interest, different performance measurements can be used to pick the optimal classifier, e.g. classifier to use in screening of the whole population would require better specificity to compensate for small (~1%) prevalence of the disease and therefore avoid large number of false positive hits, while a diagnostic classifier of patients in hospital should be more sensitive.

For diagnosing cancerous tumors from benign nodules, higher sensitivity is more desirable than specificity, as the patients are already at high risk.

Example 6: Testing of the Classifiers

Peripheral blood samples were all collected in PAXgene RNA stabilizations tubes and RNA was extracted according to the manufacturer. Samples were tested on a Nanostring nCounter™ (as described above) against a custom panel of 559 probes (Table V).

For the 559 Classifier, 432 were selected based on previous microarray data, 107 probes were selected from Nanostring studies and 20 were housekeeping genes. For QC, a Universal RNA standard (Agilent) was included in each batch of 36 samples tested. Probe expression values were normalized using the 20 housekeeping genes as well as spike-in positive and negative controls supplied by Nanostring (included in classifier). Zscores were calculated for probe count values and served as the input to a Support Vector Machine (SVM) classifier using a polynomial kernel. Classification performance was evaluated by 10-fold cross-validation of the samples.

A. Classifiers

Figure 1B:
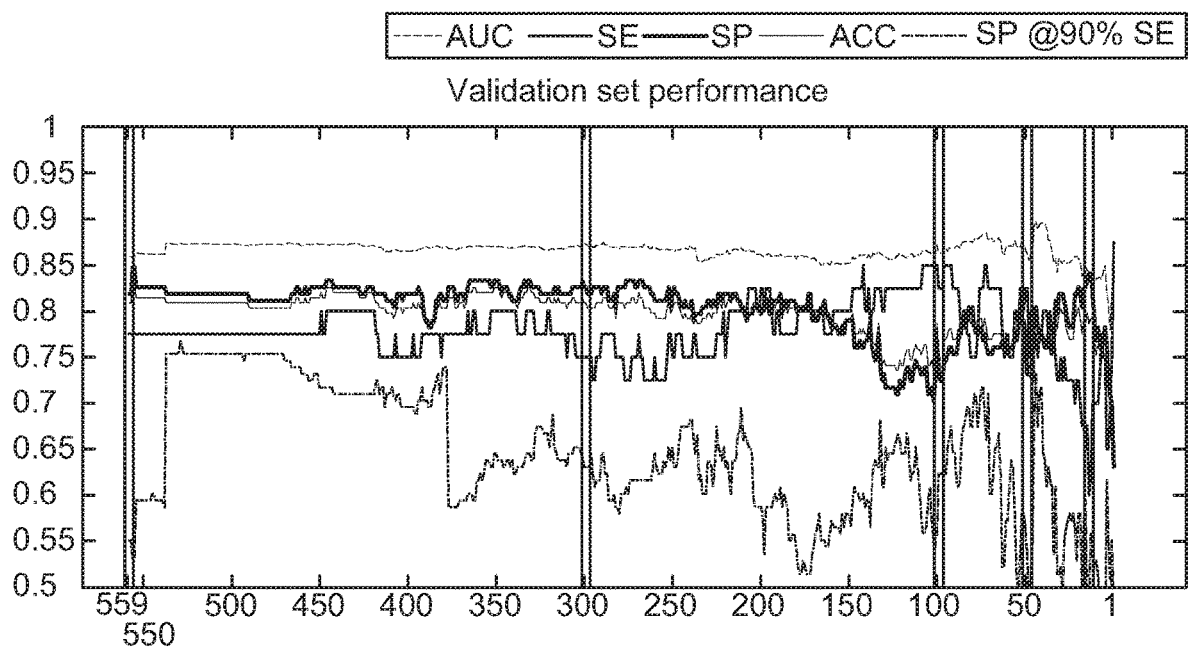
Figure 2A:
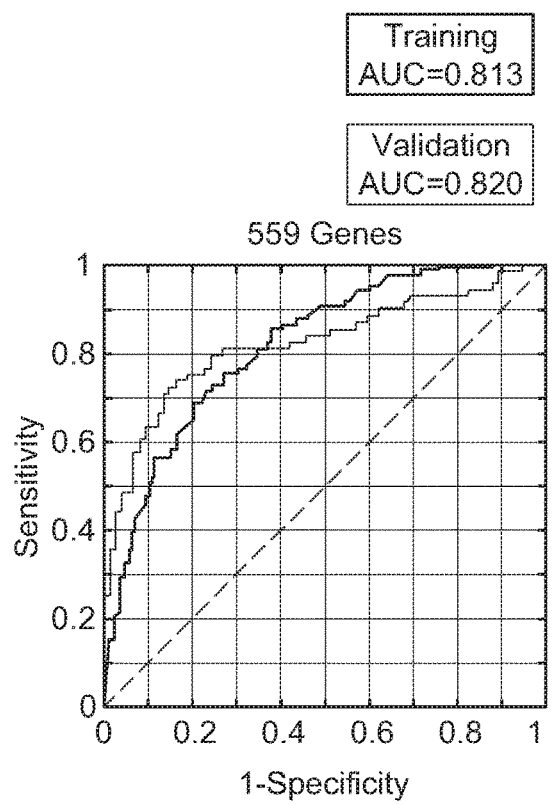
FIG. 2A-FIG. 2D demonstrate classification accuracy of nLNC.
Figure 2B:
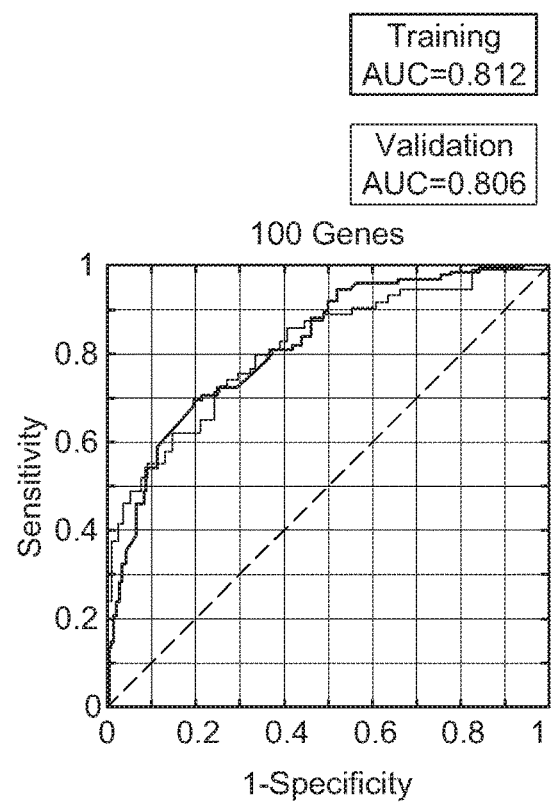
Figure 2C:
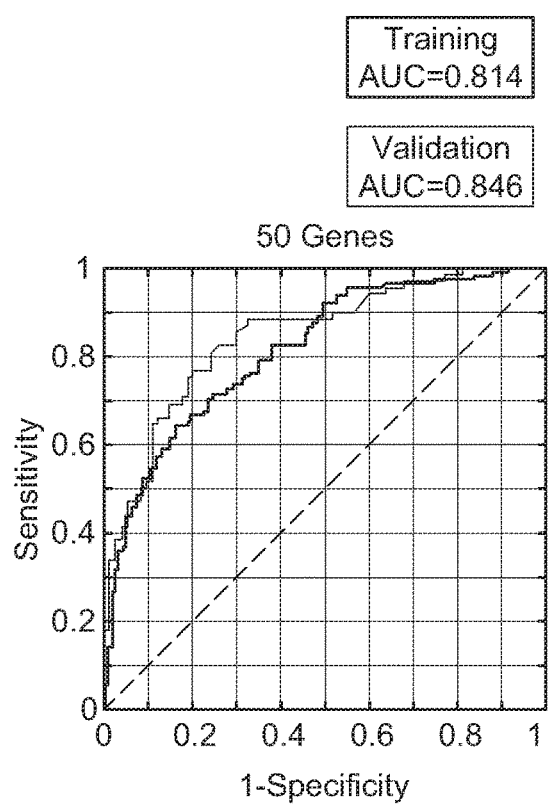
Figure 2D:
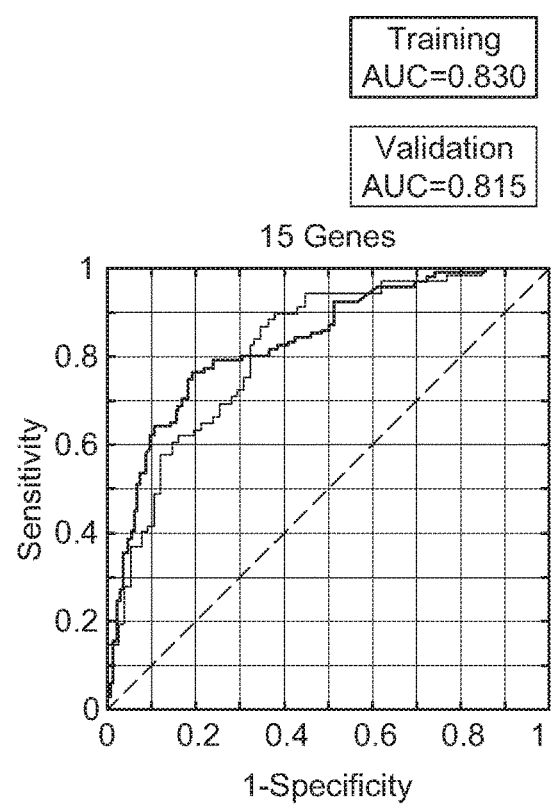

As shown in the Table VII below and FIGS. 1A to 1B, the 559 classifier developed on all the samples showed a ROC-AUC of 0.86 on the training set (FIG. 1A) and 0.85 on the testing set (FIG. 1B). With the Sensitivity set at 90%, the specificity is 62.9% and 55.1% respectively.

Figures 2, 6:
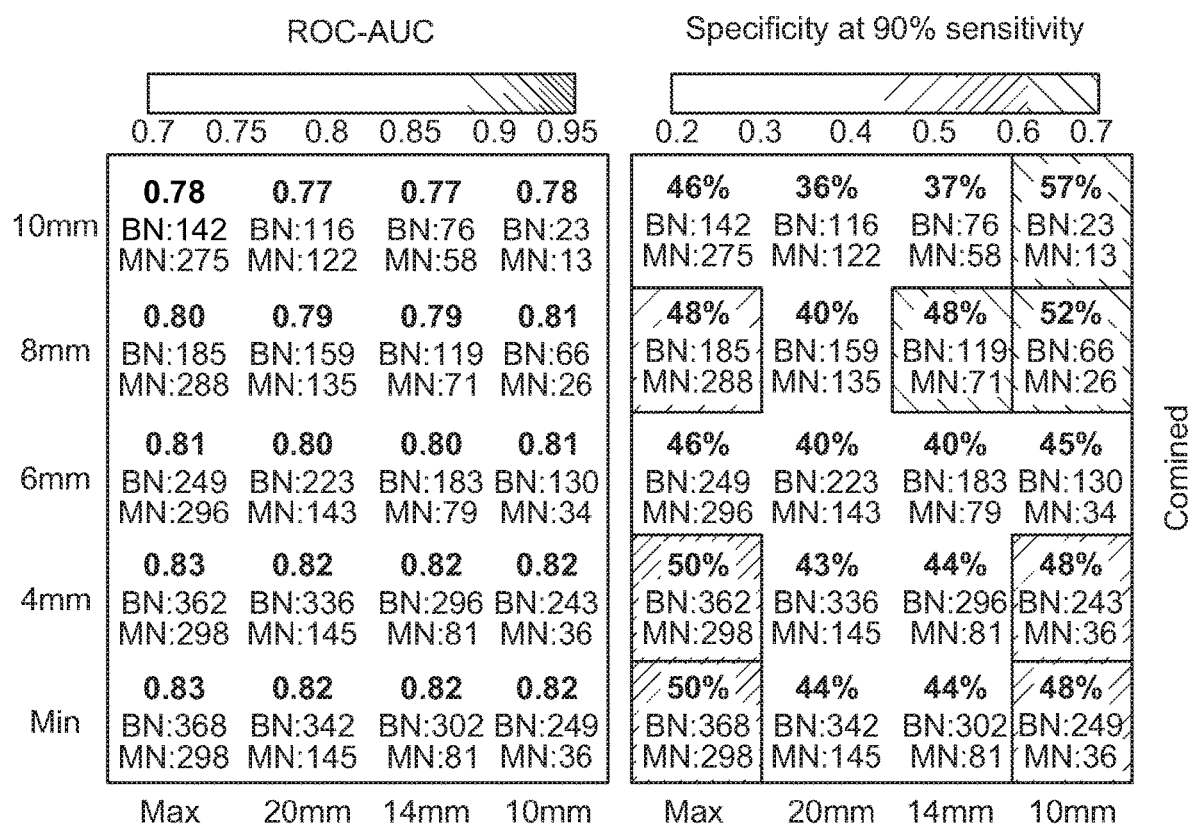
FIG. 6 shows classification performance across different nodule size ranges. Performance values (ROC-AUC on left and specificity at 90% sensitivity on right) are given for the Training (top panels), Validation (middle) and Combined data sets (bottom). Each row is labeled on the left side of the figure with the lower nodule size range from Min (any size) to 10 mm. The column labels across the bottom correspond to the upper nodule size range from 10 mm to Max (any size). Each square of a panel is then shows classification performance in distinguishing benign from malignant nodules that fall in range from lower to upper size in mm along with numbers of nodules being compared for both BN and MN classes. The color intensity is used for visual accent and is proportional to the reported performance values with the color scales shown at the top of the panels. For example, nPNC demonstrated the best ROC-AUC performance of 0.87 and a specificity of 0.64 @90% sensitivity in distinguishing 8-10 mm nodules (set contained 6 MN and 14 BN).

The data from the training and testing set samples was analyzed by W559 on the Nanostring platform in order to identify the minimal number of probes required to maintain performance attained with the whole panel. We used SVM-RFE for probe selection as previously described. Samples were randomly selected for training and testing sets as shown in Table VII below. The accuracy obtained on the testing set is shown in FIG. 1B. The ROC curves for the classifiers are shown in FIG. 2.

For the first 100 genes of Table IV, at a sensitivity of 90%, specificity of about 63% was shown for the training set, and about 58% for the validation set. For the first 50 genes of Table IV, at a sensitivity of 90%, specificity of about 58% was shown for the training set, and about 56% for the validation set. For the first 15 genes of Table IV, at a sensitivity of 90%, specificity of about 51% was shown for the training set, and about 46% for the validation set. For the first 7 genes of Table IV, at a sensitivity of 90%, specificity of about 67% was shown for the training set, and about 46% for the validation set.

former smokers (>50 yr, >30 pack years) (1, 2) has led to a significant increase in LDCT lung screening. While LDCT is capable of identifying significantly smaller nodules than conventional x-rays this capability comes with the subsequent challenge of distinguishing that small percentage of those nodules that are malignant from the major percentage of nodules that are benign (3). The NLST detected lung nodules 4 mm or greater in diameter in 40% of patients 56, screened with 96.4% of the positive scans being false positives (4). This is particularly problematic for that class of indeterminate pulmonary nodules (IPNs) ranging in size from 4 to 20 mm (4). Although IPNS detected by the growing numbers of LDCT scans represent a clinical dilemma, they also provide the opportunity to potentially detect lung cancers at the earliest stages of development. In our earlier studies we demonstrated that rapidly purified (within 2 hours) PBMC contained gene expression data that could accurately distinguish benign from malignant lung nodules with high accuracy (ROC-AUC 0.86) (5). We now report that PAXgene blood RNA stabilization tubes provide the possibility to collect samples in many different clinical settings with RNA profiles being captured at the time of sample collection. The PAXgene RNA is stable at room temperature for 5-7 days providing the potential to be transferred to a central testing facility like many other routine blood tests (6-8). The stability of the RNA for >7 years at −20 C to −80 C is an added benefit for large studies. This ease of collection and stabilization comes with the caveat that the whole blood RNA would contain information from a wider variety of blood cells including granulocytes and neutrophils not included in the PBMC samples and that as a result identifying an accurate gene expression signature might be more complex. The main objectives of this study were: (i) to demonstrate whether PAXgene-stabilized RNA from whole blood can be successfully mined gene expression information that can accurately distinguish malignant from benign lung nodules detected by LDCT, and (ii) to determine whether a diagnostic signature developed on

TABLE VII

| | Performance | N genes | | | | | |
|---|---|---|---|---|---|---|---|
| | set Metric | 559 | 300 | 100 | 50 | 15 | 7 |
| Training | Sensitivity (SE) | 78.6% | 77.8% | 79.5% | 77.8% | 82.9% | 79.5% |
| | Specificity (SP) | 72.4% | 73.3% | 77.1% | 76.2% | 76.2% | 79.0% |
| | Accuracy (ACC) | 75.7% | 75.7% | 78.4% | 77.0% | 79.7% | 79.3% |
| | ROC-AUC (AUC) | 0.860 | 0.856 | 0.873 | 0.866 | 0.871 | 0.851 |
| | SP @ 90% SE | 62.9% | 61.0% | 62.9% | 58.1% | 51.4% | 67.6% |
| Validation | Sensitivity (SE) | 77.5% | 75.0% | 80.0% | 82.5% | 67.5% | 77.5% |
| | Specificity (SP) | 81.9% | 82.6% | 79.0% | 77.5% | 83.3% | 76.1% |
| | Accuracy (ACC) | 80.9% | 80.9% | 79.2% | 78.7% | 79.8% | 76.4% |
| | ROC-AUC (AUC) | 0.859 | 0.874 | 0.852 | 0.868 | 0.844 | 0.834 |
| | SP @ 90% SE | 55.1% | 63.0% | 58.0% | 56.5% | 46.4% | 46.4% |

B. Further Analysis

Further analysis was performed and the gene classifiers of Tables I, II and III developed.

Example 7: 15 Marker Panel

Lung cancer remains the primary cause of cancer-related deaths world-wide, in part due to the lack of adequate early detection protocols and in part because common early symptoms are easily ignored. The demonstration that lung cancer screening by low-dose computed tomography (LDCT) can reduce mortality among high-risk current and whole transcriptome Illumina microarrays can be transitioned to the more robust, clinically established NanoString nCounter platform which has been FDA approved for the Prosigna™ Breast Cancer prognosis assay (9). We now report the successful development of a lung nodule classifier (LNC) based on Illumina whole genome microarrays with a ROC-AUC of 0.847 on independent validation. We further describe the successful transitioning of that microarray classifier to the NanoString nCounter™ platform with a demonstrated ROC-AUC of 0.846 on independent validation. This nLNC has the potential to address the present IPN dilemma and the potential for lung cancer overtreatment.

Whole Blood Gene Expression Distinguishes Malignant from Benign Lung Nodules Detected by LDCT Blood samples were prospectively collected in RNA stabilizing PAXgene tubes at 5 clinical sites. The samples were from patients at high risk for lung cancer (>50 years >20 pack years) all with lung nodules detected by LDCT or x-Ray. Nodules were confirmed as malignant (MN) or benign (BN) by bronchoscopy, biopsy and/or lung resection or by at least 2 years of LDCT follow-up. Purified PAXgene sample RNA (See Methods) was assayed on Illumina H12 v4 microarrays to assess feasibility of using PAXgene RNA to develop a Lung nodule classifier with accuracies similar to that we achieved using RNA from PBMC (5). The demographics for the patients used in the microarray study are shown in Table VIII. Study patients are primarily smokers and ex-smokers >50 years of age with >20 pack years of smoking history. The cancers used to develop the models are early stage with Stage I+II cancers making us 84% of the test population and with 100% of the cancers in the validation set being Stage I. The data was analyzed using SVM-RFE as previously described (5, 10).

TABLE VIII

Demographics for samples in the microarray study.

| Category | Illumina Training set | | | Illumina Validation | | |
|---|---|---|---|---|---|---|
| | MN | BN | p-value | MN | BN | p-value |
| Total N | 131 | 133 | | 33 | 18 | |
| Gender | | | | | | |
| Female | 73 | 68 | 0.454 | 24 | 11 | 0.5294 |
| Male | 58 | 65 | | 9 | 7 | |
| Age | 67 ± 7 | 65 ± 7 | 0.0291 | 72 ± 7 | 64 ± 7 | 0.0057 |
| Race | | | | | | |
| Black | 19 | 17 | | 3 | 2 | |
| White | 107 | 108 | 0.1205 | 30 | 15 | 0.3753 |
| Other | 5 | 8 | | 0 | 1 | |
| Smoking Status | | | | | | |
| Current | 33 | 47 | | 8 | 6 | |
| Former | 90 | 81 | 0.1652 | 23 | 10 | 0.4663 |
| Never | 8 | 5 | | 2 | 1 | |
| Unknown | 0 | 0 | | 0 | 1 | |
| Pack Years | 40 ± 21 | 38 ± 14 | 0.7249 | 36 ± 19 | 41 ± 21 | 0.9621 |
| Site | | | | | | |
| HFGCC | 68 | 22 | | 14 | 1 | |
| NYU | 22 | 73 | | 15 | 8 | |
| Temple | 2 | 11 | $8 \times 10^{-13}$ | 0 | 1 | 0.0062 |
| UPenn | 39 | 27 | | 4 | 8 | |
| Lesion Size, mm. | 22 ± 8 | 8 ± 4 | $1 \times 10^{-13}$ | 17 ± 4 | 15 ± 4 | 0.3277 |
| Cancer stage | | | | | | |
| I | 87 (66%) | | | 33 (100%) | | |
| II | 23 (18%) | | | 0 | | |
| III | 7 (5%) | | | 0 | | |
| IV | 9 (7%) | | | 0 | | |
| Unknown | 5 (4%) | | | 0 | | |

We analyzed a training set of 264 samples (Table VIII) to identify the gene probe classifiers that most accurately distinguished malignant and benign lung nodules and to assess the changes in classification performance with decreasing numbers of gene probes using a 10-fold 10-resample cross-validation SVM-RFE method (5, 10). While the accuracy of classification was stable across a wide range of probe numbers, the area under the ROC curve (AUC) decreased slightly as probes were eliminated. Using 1000 probes achieved an AUC of 0.88 while 150 produced an AUC of 0.85. Even as few as 15 genes were enough to classify the training set with an AUC>0.8. We selected the smallest number of gene probes that maintained an AUC within 1% of that achieved by the 1000 genes and identified a classifier of 311 gene probes that produced an AUC of 0.866 (Data not shown). This performance was maintained when the classifier was applied to an independent patient validation set (Table VIII columns right) achieving and AUC of 0.847 (Data not shown) confirming that a robust signal associated with the presence of a lung cancer could be detected in PAXgene RNA with an overall performance similar to our previously published PBMC results.

Having verified that RNA from PAXgene samples can distinguish malignant from benign lung nodules detected by imaging with high accuracy, we developed a strategy to transition our microarray based LNC to the more clinically appropriate NanoString nCounter platform (9).

Transitioning to the NanoString Platform

In order to select the probes for a NanoString diagnostic gene expression panel, several considerations were taken into account. Without knowing how well the NanoString gene expression measurements would replicate the performance of the Illumina microarray platform, we designed our custom panel to contain enough redundancy to be able to overcome the platform differences and included gene probes selected by different criteria. SVM-RFE was the primary method used for selection. While SVM is a powerful tool for developing a classification model, we took into account the possibility that some probes that performed well on the microarrays would not demonstrate an equivalent performance on the NanoString platform. To increase our pool of relevant genes, we also selected 59 probes with the minimal p-values across the comparisons (p<10-4) and 76 probes with a maximum fold change at a p<0.01 in the classification. We also identified candidate housekeeping genes that were expressed at >5 fold above the microarray background, with coefficients of variation less than 20% for absolute values and 2.5% for log 2-scaled expression values. The top 12 least variable candidates and 8 additional known NanoString housekeeping genes were selected for a final list of 20 housekeeping genes.

One of the major differences between the microarray and NanoString platforms is that no enzymatic processing is required to assess gene expression on the NanoString. This means Reverse transcription and no PCR amplification of gene targets associated with the analysis. This minimized sample handling eliminates potential for amplification biases and makes the platform attractive for a clinical application, but there was the possibility that some of the selected biomarkers might be expressed at levels too low for detection without the PCR amplification. To address this issue we analyzed most of the samples from the Illumina microarray training set on the NanoString PanCancer Immune panel (cat. XT-CSO-HIP1-12) in order to correlate levels of gene expression that could be detected by each platform. We analyzed 220 of the training samples including 115 MN and 105 BN samples. 755 out of 770 genes represented in the NanoString PanCancer Immune panel were also represented on the microarray platform although the gene probes were different. Although the exact probes differed between the 2 platforms, this analysis provided an estimate of levels of gene expression that could be robustly detected on both platforms. The studies suggested that probes detected at 5× the microarray background levels were robustly detected on the NanoString. We also used the PanCancer Immune panel study as an additional discovery platform, as these probes were already well validated as working well together on the NanoString platform. We used 10-fold 10-resample SVM to estimate performance accuracy for the NanoString PanCancer Immune panel. Although the NanoString panel demonstrated lower performance with an AUC=0.754 compared to the 0.866 achieved with the microarray training set, at 90% Sensitivity the Specificity was still 37% and we selected a set 106 probes for inclusion in our custom panel. We also added an additional 55 probes identified in our previous PBMC studies as being associated with diagnosis, outcome and/or post resection gene expression changes (11, 13) for consideration in future studies.

In order to assess the similarity between classification using the Illumina and NanoString platforms, 222 training set samples that were run on both platforms using the 276 SVM-RFE probes once again taking into consideration that the probe differences and the differences in the 2 platform technologies. Considering just the 276 SVM-RFE probes we compared the cross-validation SVM scores of these samples using both platforms, and observed a Spearman correlation of 0.72 between platforms which we considered to be sufficient to proceed with the evaluation of new samples. We assayed 414 samples on the 559 probe custom NanoString panel. We utilized 142 samples with 8-20 mm lesions, which are the range that makes up the IPN population of interest. The remaining 272 samples were used for training the model. The model developed on this training set demonstrated an AUC of 0.813 and achieved an AUC of 0.820 on the validation set (Data not shown). This confirmed that the gene selection approaches had been effective.

We further refined the model using recursive feature elimination (RFE). Application of SVM-RFE to the training set revealed that classifier performance is stable down to 15 NanoString probes with the nLNC returning a training AUC=0.867 (FIG. 2). The AUCs determined on the independent validation set are similarly stable with an AUC=0.843 for 15 genes although the variability of AUC increases and specificity at 90% sensitivity begins to drop slightly when fewer than 50 probes are used in the classification. In one embodiment, the 15 or 50 genes are selected from those in Table II or Table III.

Our previous studies on gene expression in RNA from PBMC collected under standardized conditions demonstrated that peripheral blood not only contains information to distinguish malignant from benign lung nodules but also contains information that is correlated with prognosis. The current study we addressed 2 goals 1) the simplification of sample collection and 2) moving the assay to a clinically accessible platform. In addressing the first goal we implemented a simple, easily standardized method for sample collection using the PAXgene collection tubes. This allowed the collection of samples not just at University Centers but also at community centers not easily included in previous studies. This pilot study establishes the feasibility of using whole blood RNA collected in PAXgene tubes to accurately distinguish patients with malignant lung nodules from the large numbers of individuals with benign lung nodules detected by the growing numbers of screening programs. The ease of PAXgene sample collection has allowed us to undertake the large studies needed to address lung cancer diversity. In this study we have primarily focused on NSCLC, the most common of the lung cancers, smaller early stage cancers and high-risk smokers and ex-smokers.

The second goal that we had set was to move the LNC from the microarray discovery platform to a more clinically appropriate detection platform. The NanoString nCounter platform was chosen based the ease of sample handling and the elimination of many of the enzymatic steps that are known to result in biases and batch effects we found in our PBMC study. Also, the amount of test sample required is easily obtained. We used 100 ng of RNA for all of the NanoString assays reported here but as little as 10 ng is also possible. We found that although larger amounts of RNA are compatible with the platform, using the higher sensitivity scan setting of FOV 550 was more effective in increasing signal than increasing the amount of RNA.

We have also tested the stability of NanoString gene panel with relationship to reagent batches, personnel changes and sample sources with no detection of significant batch effects. A universal Human RNA standard was initially included on each 12 sample cassette. This was reduced to one per week to evaluate scanner and assay performance. While we required RNA Integrity Numbers (RINs) >7.5 for our microarray studies, and although PAXgene RINs are routinely >8.0 we were also able to assay RNA from PAXgene samples that had been thawed and refrozen in a −80 C freezer malfunction. We assessed 5 RNA samples with RINs as low as 3.2. The overall signal intensities were well within the NanoString quality control parameters. In addition, in the event of a scanning problems, the cassettes can be scanned again within 24 hours with little or no loss of information when stored as NanoString recommends.

Example 8: 41 Marker Panel (Table IX)

With cigarette smoking as the acknowledged root cause, lung cancer remains the primary source of cancer-related deaths world-wide. This is in part due to the lack of adequate early detection protocols, and in part because early symptoms are so subtle. The demonstration that lung cancer screening by low-dose computed tomography (LDCT) reduces mortality among high-risk current and former smokers (>55 yr, >30 pack years) (1-3) led to an overall increase in LDCT screening programs (4). Although LDCT does identify significantly smaller nodules than conventional x-rays, this ability comes with the challenge of distinguishing the small percentage of pulmonary nodules that are malignant from the majority of those detected that are benign (5). The National Lung Screening Trial (NLST) detected lung nodules ≥4 mm in diameter in 40% of patients screened, with 96.4% being false positives over the 3 rounds of screening (6). To reduce this high FPR the recent Lung-RADs classification (7) and new guidelines from the Fleischner group (8) set the detection of nodules ≥6 mm as the positive threshold. However, positive CT scans remain particularly problematic for that class of indeterminate pulmonary nodules (IPNs), which range in size from 6 to 20 mm for which the best course of clinical action is not well specified (6).

Our earlier studies demonstrated that rapidly purified (within 2 hours) peripheral blood mononuclear cells (PBMC) contain gene expression data that can distinguished benign from malignant lung nodules with high accuracy (9). This work established a new paradigm in nodule diagnosis by showing that even an early stage cancer in the lung affects gene expression in PBMC that is predictive of malignancy. However, this approach was limited by the need to rapidly purify PBMCs from blood samples in order to maintain sample consistency and RNA integrity. This made it difficult to collect samples in environments where rapid isolation of PBMC was not possible, including most community clinics and physician offices. Additionally, the microarrays, which were so useful for diagnostic development, are technically complicated and prone to variabilities associated with reagent batches and enzymatic processes, making them less amenable to clinical applications. The high quality of RNA required for microarray studies is also potentially problematic for studies with patient derived samples (10). The present retrospective/prospective study sought to determine whether accuracies similar to what we achieved in our PBMC studies (9) could be achieved with RNA from whole blood collected in RNA stabilizing PAXgene™ tubes. PAXgene RNA is stabilized at the time of collection, immediately fixing gene expression patterns. The RNA is stable at 15-25° C. for 5 days and at −20 to −70° C. for 8 years. This allows samples to be collected in any clinical setting where blood is drawn without the need for special equipment for storage or for cell purifications (11-13) and allows samples to be transferred to a central facility for testing, as routinely as with other blood tests. In addition, long term storage with no loss of RNA integrity makes the system well suited for retrospective analyses. We also asked whether a PAXgene signature developed on Illumina microarrays could be transitioned to the NanoString nCounter platform already FDA approved for the Prosigna™ Breast Cancer prognosis assay (14) and more recently used to develop a clinical-grade assay that predicts clinical response to PD-1 checkpoint blockade. This PD-1 assay is currently being evaluated in ongoing pembrolizumab clinical trials (15). Since the NanoString assays do not include any enzymatic reactions or amplification steps, the system avoids potential reagent batch effects and PCR biases while decreasing opportunities for cross contamination by minimizing sample handling. While we recognized that a gene expression profile from whole blood would be of a greater complexity and could potentially result in a reduction in important diagnostic signals, there was also the prospect that important additional cell types might contribute to the classifier performance.

We now report that gene expression in whole blood, collected using PAXgene RNA stabilization tubes, can distinguish benign from malignant lung nodules detected by LDCT with high accuracy on independent validation and also report the successful transition of this pulmonary nodule classifier from the microarray developmental platform to the NanoString nCounter™ platform.

Study Design

Figure 3:
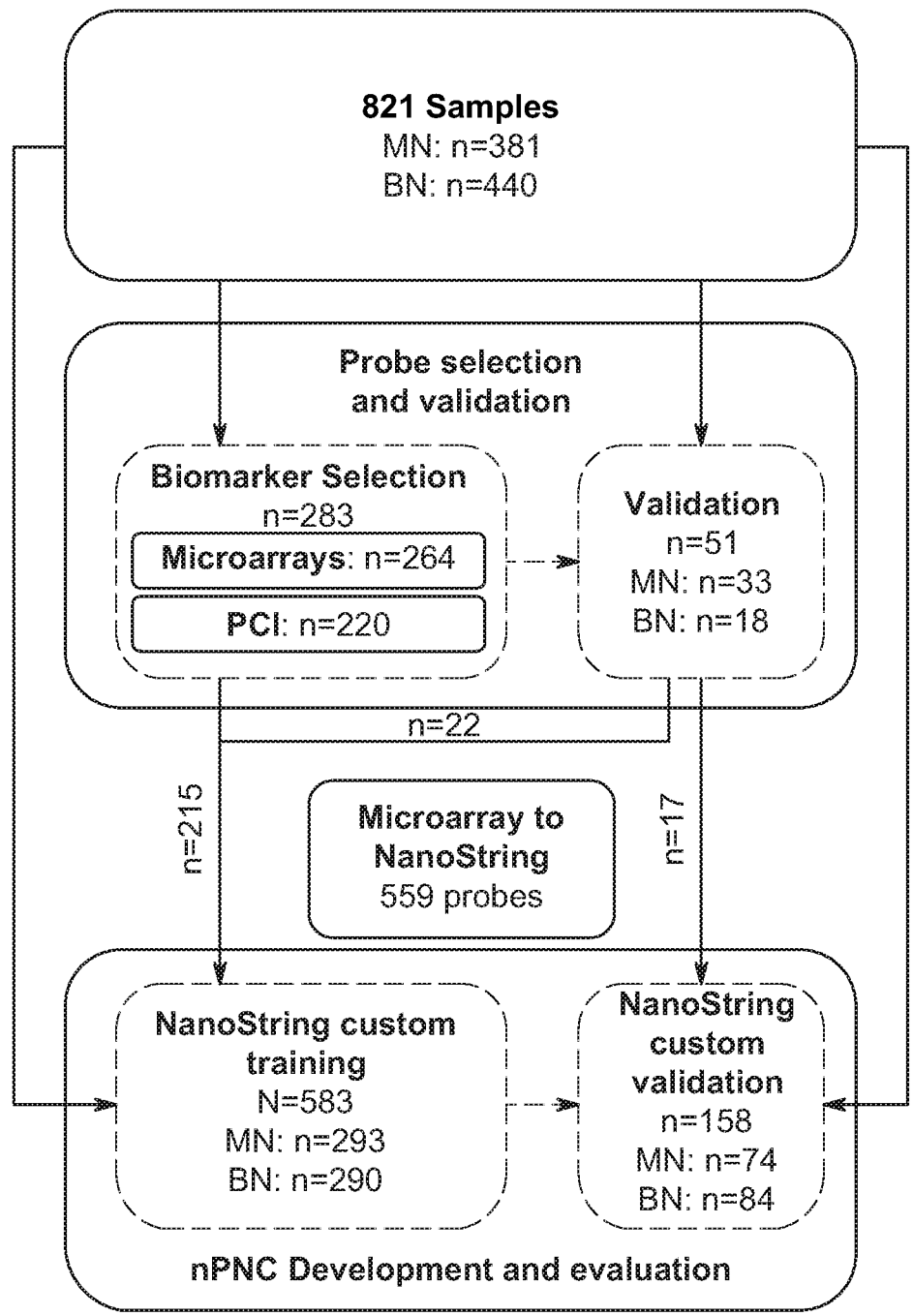
FIG. 3 shows the study design. A total of 821 unique samples were analyzed in this study. Illumina HT12v4 microarrays and the NanoString PCI panel were used to select candidate biomarker probes using 283 total samples. 264 samples were used for biomarker selection on microarrays and 201 of the 264+19 new samples were used to select the biomarkers from the PCI panel. The 51 samples used for validation were not used in any biomarker selection. 559 of the biomarkers selected from the microarray and the PCI panel analyses were successfully designed for the NanoString custom panel. The custom panel was assayed with 237 of the samples used in probe selection, to ensure that the new platform successfully reproduced the microarray results, and an additional 346 independent samples not previously assayed on any platform (total 583). The 583 training samples were used to create a NanoString pulmonary nodule classifier (nPNC). An additional 158 samples that were never involved in NanoString probe selection were used for Nanostring custom platform (346 for training and 141 for validation) for a total of 821 independent samples.

The process of biomarker selection and validation across all studies is summarized in FIG. 3. A total of 821 samples from patients with malignant (MN) and benign (BN) pulmonary nodules were analyzed across 3 platforms: Illumina microarrays, the NanoString Pan Cancer Immune (PCI) panel and finally a custom NanoString custom panel. Microarray data from 264 patient samples (Table VIII, Table XIII) from 4 clinical sites was used for microarray model development. Estimations of performance were based on an independent validation set of 51 samples. In addition, 220 samples including 201 of the 264 microarray samples were analyzed on the NanoString PCI platform to select additional biomarkers to be included in the custom NanoString panel. Samples from a $5^{th}$ collection site not included in the biomarker selection process were analyzed only on the custom NanoString platform. The final nPNC was developed on the data generated from the custom Nanostring panel using 583 training samples (included 215 samples used originally in the microarray training set, and 368 samples (70%) never used for the biomarker selection) and validated using a set of 158 independent samples never involved in probe selection.

TABLE XIII

| Category | Illumina Training set full | | Illumina Training subset A | | Illumina Training subset B | | Illumina Validation | |
|---|---|---|---|---|---|---|---|---|
| | MN | BN | MN | BN | MN | BN | MN | BN |
| Total N | 143 | 140 | 71 | 73 | 60 | 60 | 33 | 18 |
| Gender | | | | | | | | |
| Female | 81 | 70 | 38 | 38 | 35 | 30 | 24 | 11 |
| Male | 62 | 70 | 33 | 35 | 25 | 30 | 0 | 7 |
| Unknown | 0 | 0 | 0 | 0 | 0 | 0 | 0 | 0 |
| Age | 67 ± 7 | 65 ± 7 | 66 ± 7 | 64 ± 6 | 67 ± 7 | 66 ± 9 | 72 ± 7 | 64 ± 7 |
| Race | | | | | | | | |
| Black | 20 | 17 | 14 | 5 | 5 | 12 | 3 | 2 |
| White | 117 | 120 | 54 | 67 | 53 | 46 | 30 | 15 |
| Other | 6 | 3 | 3 | 1 | 2 | 2 | 0 | 1 |
| Smoking | | | | | | | | |
| Current | 35 | 51 | 29 | 28 | 13 | 19 | 8 | 8 |
| Former | 99 | 84 | 48 | 42 | 42 | 39 | 23 | 10 |
| Never | 0 | 5 | 3 | 3 | 5 | 2 | 2 | 1 |
| Unknown | 0 | 0 | 0 | 0 | 0 | 0 | 0 | 0 |
| Pack Years | 40 ± 22 | 38 ± 14 | 38 ± 17 | 38 ± 14 | 40 ± 27 | 38 ± 15 | 36 ± 19 | 41 ± 21 |
| Lesion, mm | 22 ± 9 | 8 ± 8 | 22 ± 8 | 8 ± 2 | 25 ± 12 | 14 ± 8 | 17 ± 4 | 18 ± 4 |
| Cancer stage | | | | | | | | |
| I | 98 (89%) | | 55 (77%) | | 32 (53%) | | 33 (100%) | |
| II | 24 (17%) | | 16 (23%) | | 7 (12%) | | 0 | |
| III | 7 (5%) | | 0 | | 7 (12%) | | 0 | |
| IV | 9 (6%) | | 0 | | 9 (10%) | | 0 | |
| Unknown | 8 (3%) | | 0 | | 5 (8%) | | 0 | |
| Clinical Site | | | | | | | | |
| HFGCC | 70 | 23 | 35 | 11 | 33 | 11 | 14 | 1 |
| NYU | 29 | 79 | 11 | 44 | 11 | 29 | 15 | 8 |
| Temple | 2 | 11 | 2 | 3 | 0 | 8 | 0 | 1 |
| UPenn | 42 | 27 | 23 | 15 | 16 | 12 | 4 | 8 |

Median ± IQR are givn for continuous values, p-values indicates significance of comparison between BN or MN group Study Population Samples were prospectively collected from incidental subjects with a positive LDCT from 5 clinical sites including Helen F. Graham Cancer Center, The Hospital of the University of Pennsylvania, Roswell Park Comprehensive Cancer Center, Temple University Hospital and subjects from New York University Langone Medical Center. The NYU subjects included patients recruited as a part of an EDRN lung screening program at NYU. The study was IRB approved at each participating site and conducted according to the principles expressed in the Declaration of Helsinki. All participants signed an informed consent before being enrolled. The study population was primarily smokers and ex-smokers, >50 years of age with >20 pack-years of smoking history and no previous cancer in the past 5 years (except for non-melanoma skin cancer). Nodules were confirmed as malignant (MN) or benign (BN) by repeated imaging or by pathologic diagnosis through bronchoscopy, biopsy and/or lung resection. In addition, >97% of benign nodules had four or more years of follow-up with the remainder having two or more years at the time of analysis. Samples associated with MNs were collected within 3 months of definitive diagnosis or prior to any invasive procedure including curative surgery. A small number of participants were found to be never smokers after they had been assayed. The effect on classifier performance of including these samples was assessed. In cases where multiple nodules were present the diameter of the largest nodule was reported.

RNA Purification, Quality Assessment and Microarrays

Each collection site was provided with a standard protocol for sample collection and storage as specified by Preanalytix (https://www.preanalytix.com/products/blood/rna for the PAXgene Blood RNA Tube (IVD)). Samples were either stored on site and then bulk transferred over-night on dry ice, or they were transferred to Wistar by courier on the day of collection and stored at −70 C until processing. Total RNA was isolated using the PAXgene miRNA Kit (Qiagen), to capture miRNAs as well as mRNAs. Samples were quantitated with NanoDrop 1000 Spectrophotometer (Thermo Fisher Scientific) and assayed for RNA integrity on the Agilent 2100 BioAnalyzer. Average RNA yields were 3 µg/2.5 mls of blood and on average RIN numbers are >8. Only samples with RNA integrity numbers (RIN) >7.5 were used for the microarray studies. A constant amount (100 ng) of total RNA was amplified (aRNA) using the Illumina approved RNA amplification kit (Epicenter) and hybridized to the Human-HT12 v4 human whole genome bead arrays. Microarrays were processed in sets of 48 to minimize potential batch effects.

NanoString Assay Conditions

The NanoString hybridization was carried out for a constant 19 (within the recommended 12 to 25 hours) hours at 65° C. Post-hybridization processing in the nCounter Prep Station used the standard settings. The cassette scanning parameter was set at high (555 FOV). The 555 FOV setting significantly increases the overall signal. (Data not shown). All assays were carried out using this setting. The standard sample size was 100 ng, an amount we expected to have in all samples. We found stability of the assay across multiple repeats of the Universal Human RNA (UHR) control sample. (Data not shown). Variations less than 5% were observed for the majority of the gene probes with 50 or more detected counts. It was found that although most sample RIN numbers were above 8 even samples with RINs≤3 met all 4 NanoString quality measures, supporting the platforms utility with degraded RNA samples. We found no significant impact on the overall expression profiles for the degraded RNA. (Data not shown).

Data Analysis

Microarrays: Microarray raw expression data was exported for analysis using Genome Studio software. The raw data was quantile normalized and $\log_2$-scaled. Genes with average expression values ≥2× the background levels were used to develop the PNC using SVM-RFE and 10-fold 10-resample cross-validation (see details below). The top ranked probes (Borda count) that most accurately distinguished malignant from benign nodules were selected as candidates for the NanoString custom panel. The SVM training set was also stratified into subset A which containing smaller nodules and stage I and II cancers and subset B which contained malignant and benign nodules that were balanced for lesion size (Supplementary Table S1). The additional analyses of sets A and B considered either nodule class alone (MN or BN) or sample class plus collection site as factors in a linear regression model for each observed gene expression. This resulted in 6 different regression models and two additional sets of genes were selected from these analyses for inclusion in the NanoString model based on the following parameters: (i) 59 genes with a minimal p-value across the comparisons using p-value<$10^{-4}$ threshold and (ii) 76 genes with a maximum regression coefficient b>$\log_2$ (1.2) at p-value<0.01. Housekeeping (HK) genes were selected from a candidate pool of well-expressed genes (>5× background) with coefficients of variation (CV) for the absolute and $\log_2$-scaled expression less than 20% and 2.5% respectively. 20 candidate HK genes were ultimately selected: the 12 HK candidate genes with the least CV and 8 candidate genes that overlapped with existing NanoString HK probes.

NanoString: Background correction was performed on NanoString PanCancer Immune Panel samples by subtracting the geometric mean of the counts of negative controls. The sample counts were normalized by scaling all values by the ratios of geometric mean of sample controls to the overall geometric mean of control gene counts across all samples. This was done for both spike-in positive controls as well as for housekeeping genes. The NanoString custom panel was quantile normalized, and NanoString Code Set batch differences were corrected using the ratios of expression of samples replicated between code sets, as per NanoString's recommendation. Z-scores were calculated from the final values of custom panel counts and used as inputs for SVM-RFE.

SVM-RFE Data Analysis: Supervised classification using a linear kernel Support Vector Machines (SVM) with recursive feature elimination (RFE) (16) was used to analyze a z-score transformed gene expression data set to develop the microarray classifier based on a training set that that can distinguish MN and BN patient classes. A balanced set of cases and controls was used in classifier development as SVM have been shown to require a balanced input for the development of the most accurate classifiers (17). The independent validation which tests the validity of the classifier developed in the training on a completely new set of samples is blinded to identification of samples as either cases or controls. As previously described (9), we employed a 10-fold cross-validation approach with folds resampled 10 times (100 training-testing splits models). For each split of the microarray data, the top 1000 probes ranked by p-value (two-tailed t-test on 9-folds) were selected and linear kernel SVM was trained on 9-folds and tested on the remaining fold. Each RFE iteration eliminated 10% of the features with the least absolute model weights, in each round as described by Guyon et al (16). A single feature elimination per SVM iteration was used for NanoString data analysis. The final average scores were calculated as follows. The final score for any sample in a training set is calculated as an average among the scores generated for that sample in all testing folds (10 such folds among all 100 splits). The final score for any independent sample in a validation set is calculated as an average among all 100 split models. Each sample is then assigned to a class using the final average scores and a score threshold determined from the training set (0 for unbiased accuracy, or at a fixed threshold corresponding to 90% sensitivity) and sensitivity, specificity and accuracy were calculated. Probes ranking across all 100 splits was combined according to the following procedure based on the Borda count method. In each ranked list n, each gene i was assigned a score:

$$S_{i,n} = \frac{1}{r_{i,n}},$$

where $r_{i,n}$ is the rank of gene i in list n. A final score FS for each gene i was calculated by taking the sum of the scores of gene i across all 100 lists: $FS_i = \Sigma_{n=1}^{100} S_{i,n}$. The resulting final scores for each gene were then used to assign their ranking in the classifier. Final ranking of probes was produced using all 741 available NanoString samples.

Optimal number of probes for microarray data was determined as the minimum number of probes that maintained an ROC-AUC within 1% of the ROC-AUC achieved by the SVM with top 1000 gene probes. For the NanoString custom panel the optimal number of genes was chosen by determining that point where the removal of additional genes/probes resulted in a decline in classification performance. Performance was assessed by determining the ROC-AUC after the removal of each gene using the moving average with a smoothing window size of 5. The probe number at which the ROC-AUC was at maximum was selected as the final optimal classifier.

Results

Testing for a Lung Cancer Related Gene Signature Using Peripheral Blood RNA

The demographic characteristics for the 315 patients used to develop and validate the microarray lung cancer signature are shown in Table VIII. The samples used for model building were primarily early stage NSCLC with Stage I+II cancers comprising 84% of the training set population, and with 100% of the cancers in the independent validation set being Stage I.

Figure 7A:
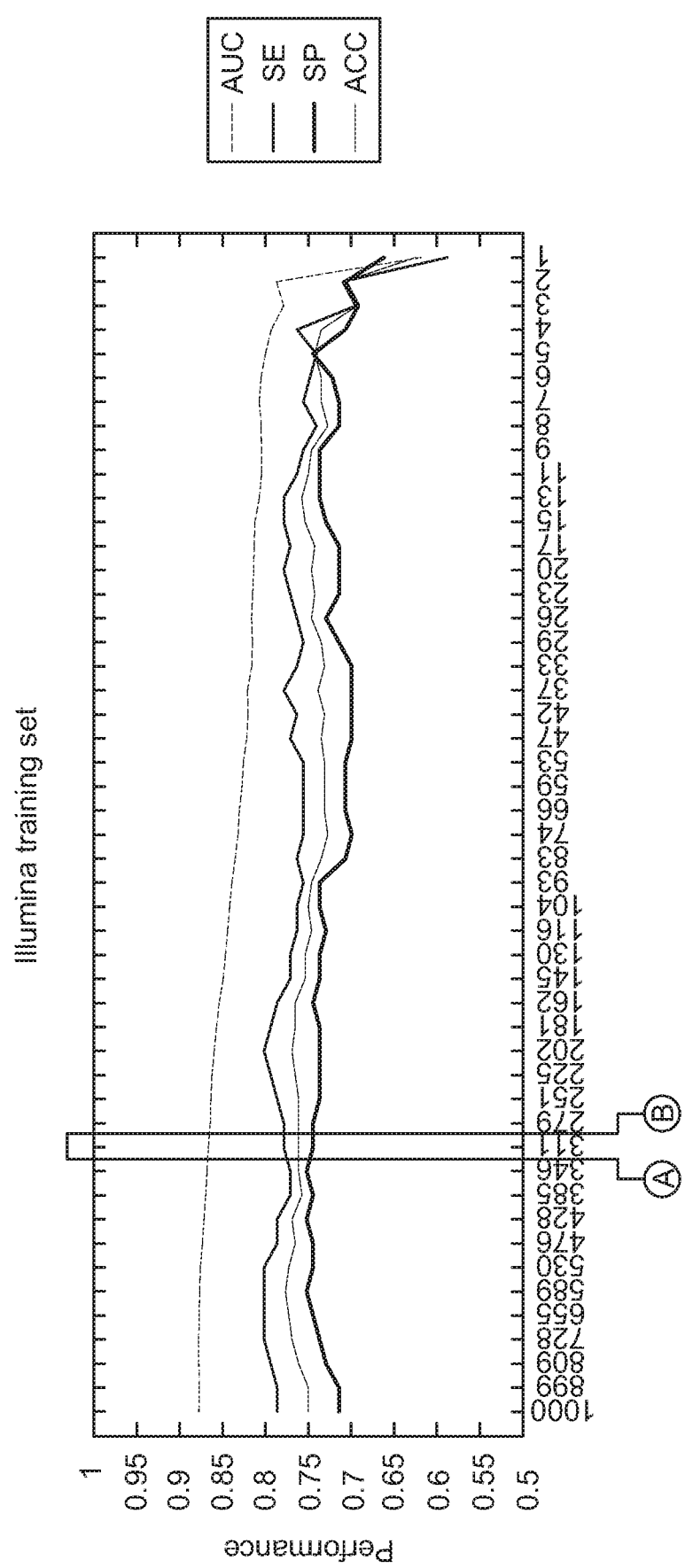

Gene expression from 264 samples (Table VIII, Illumina Training set) was used to select the microarray gene signature that most accurately distinguished malignant from benign lung nodules using SVM-RFE (9, 16). The accuracy of classification was stable across a wide range of probe numbers (FIG. 7A) and a panel of the 1000 highest ranked probes achieved an ROC-AUC of 0.878. As the performance slowly decreased with elimination of lower ranked probes, we selected the smallest number of probes that maintained an ROC-AUC within 1% of the 0.878 achieved by the top 1000 SVM gene probes. We identified 311 probes that returned an AUC of 0.866 (95% CI: 0.824-0.910) in the training set (sensitivity 77.9%, specificity 74.4%). The performance was well maintained on independent validation (Table VIII, Illumina Validation), achieving an AUC of 0.847 (95% CI: 0.742-0.951) (sensitivity 72.7%, specificity 88.9%), similar to the performance of the training set (FIG. 7B-C). This demonstrated accuracy of prediction is similar to that of the 29 gene classifier reported from our purified PBMC study (9) and indicates that the presence of cancer in the lung can be also detected in the PAXgene collected blood RNA with an equal and in some cases better performance. Importantly, the performance is maintained as the number of probes is reduced (FIG. 7A-B) indicating a robust signature is maintained across different numbers of genes.

Transitioning the PNC from Microarrays to the NanoString Platform

Having verified that mRNA expression from PAXgene samples can distinguish malignant from benign pulmonary nodules, we developed a strategy to transition the microarray-based pulmonary nodule classifier (PNC) to the NanoString nCounter platform (14). Because it was difficult to know, a priori, how the microarray expression measurements would replicate on the NanoString platform, we designed the custom panel to contain enough redundancy to mitigate platform differences. We included the top ranked 300 biomarkers from the Illumina gene panel identified by the SVM-RFE analysis. We also included an additional set of 59 markers representing the most significantly differentially expressed probes at p-value<$10^{-4}$ and 79 probes that exhibited the largest fold change in expression between the MN and BN groups while maintaining p-value<0.01. A set of 20 Housekeeping (HK) genes with the most consistent expression on the microarrays (see Methods and Materials) was also added. Since the mRNA samples to be processed on the NanoString platform did not undergo reverse transcription and PCR amplification, we were concerned that some of the microarray probes we selected might be expressed at levels too low for detection without amplification. To establish performance criteria, we analyzed 220 of the mRNA samples with the NanoString PanCancer Immune (PCI) panel (cat. XT-CSO-HIP1-12) (115 MN, 105 BN). Although the actual probes were not identical to the Illumina probes, 755 out of 770 genes represented in the PCI panel were also represented on the microarray platform. This study allowed us to correlate detectable levels of gene expression between the 2 platforms, providing an estimate of the expression levels that could be robustly detected on both platforms. The results suggested that probes detected at 2× the background levels on microarrays were robustly detected on the NanoString platform.

The PCI data was also analyzed using SVM-RFE with 10-fold 10-resample cross validation and although the PCI panel only demonstrated a ROC-AUC=0.754 compared to the 0.866 achieved with the microarrays (FIG. 7D), we selected 106 of the most discriminatory PCI probes for inclusion in our custom panel. An additional 55 probes for genes that were identified as being associated with outcome in our PBMC microarray studies (18, 19) were also added bringing the number to 619 potential probes for the NanoString custom panel. FIG. 12 summarizes the sources of the final list of the candidate biomarkers selected for the custom NanoString panel. The NanoString probes were then designed to target the same or closely located transcriptome regions as those targeted by the Illumina microarray probes whenever possible. Probes that met the NanoString quality control criteria were successfully designed for 559 of the 619 selected biomarkers (data not shown).

Developing, Refining and Validating the NanoString Pulmonary Nodule Classifier

Figure 8A:
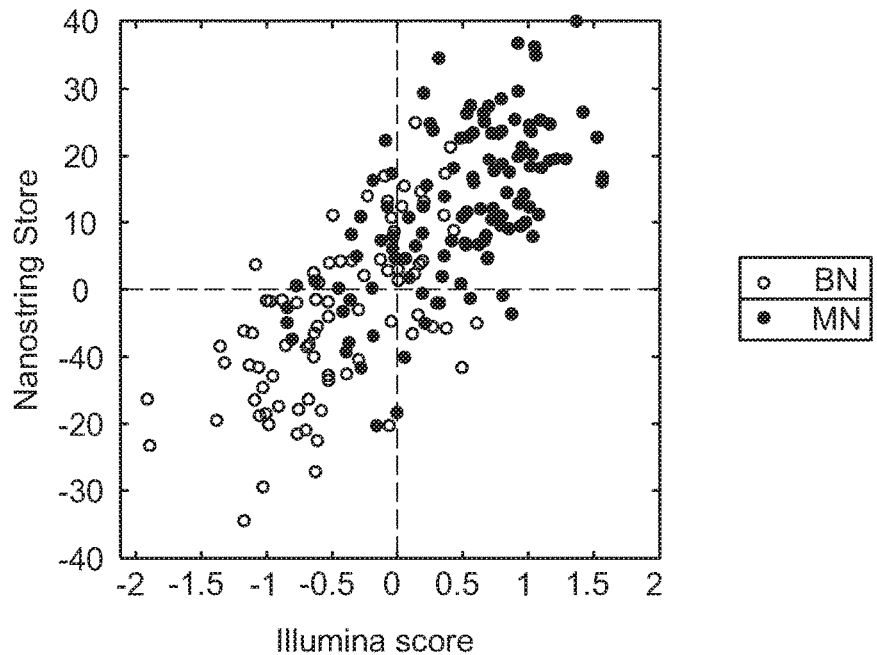
FIG. 8A and FIG. 8B show a comparison of Illumina and NanoString Classification.
Figure 8B:
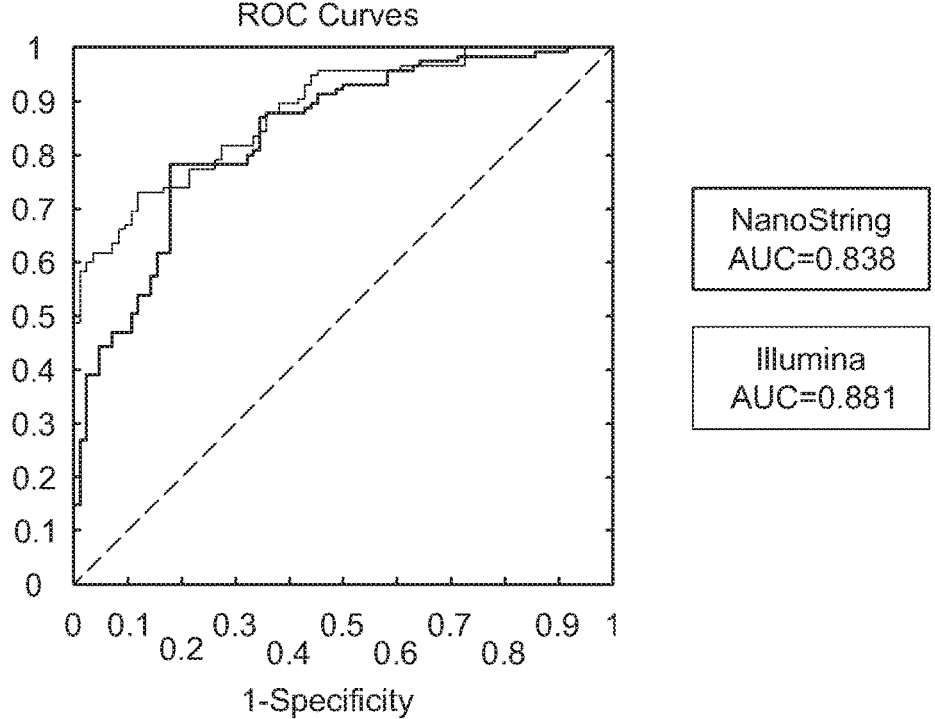
Figure 9A:
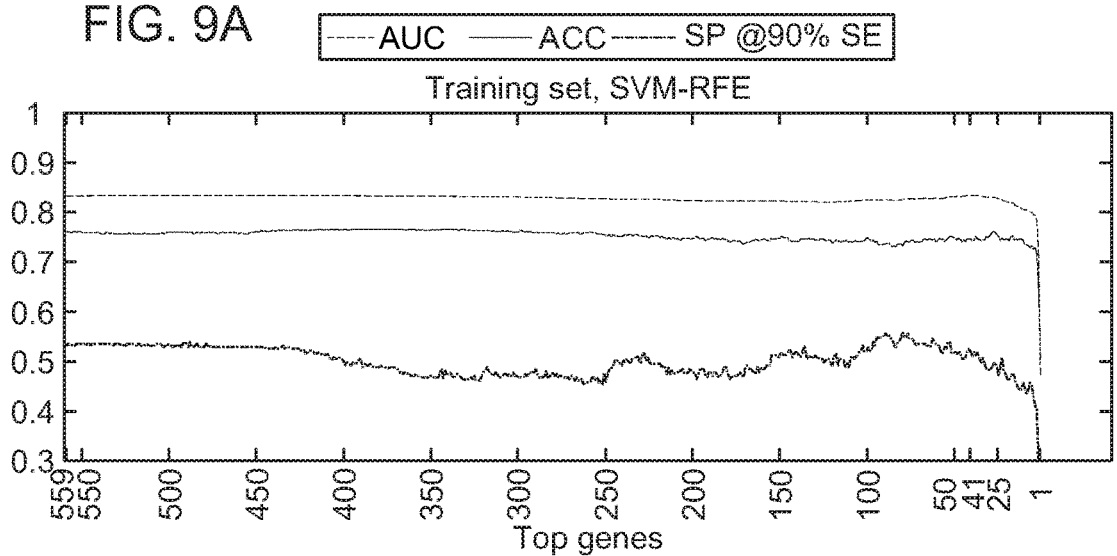
FIG. 9A-FIG. 9C demonstrate performance of NanoString Lung Nodule Classifier on training, testing and all sample set using different number of genes.
Figure 9B:
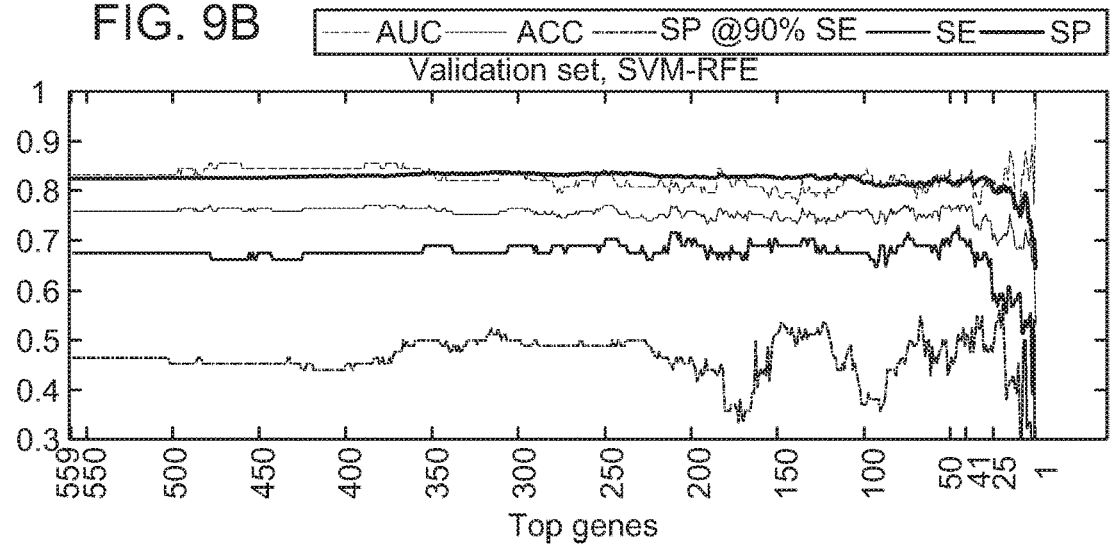
Figure 9C:
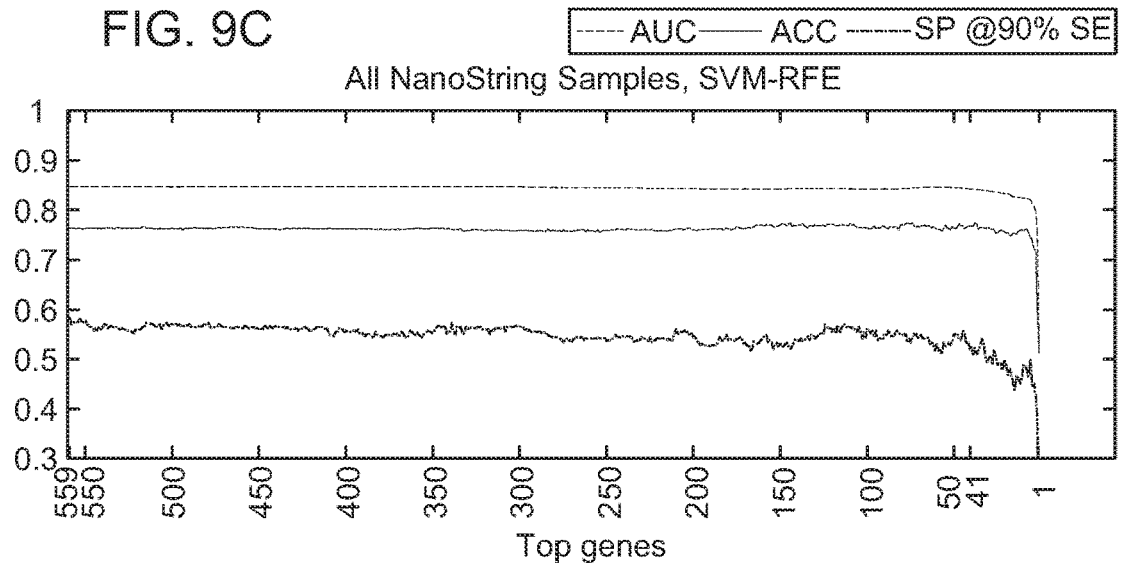
Figure 10A:
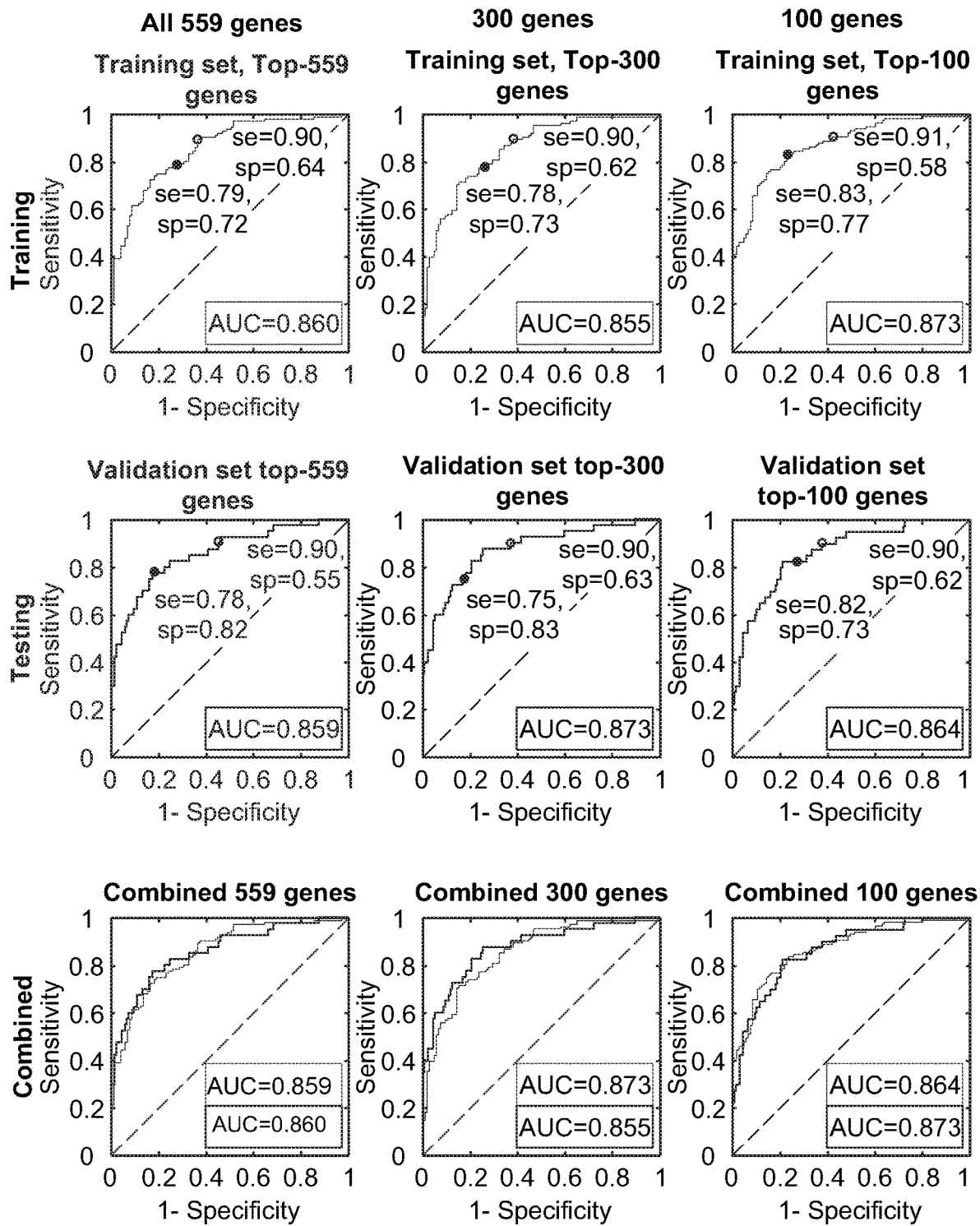
FIG. 10 shows graphs of nanostring custom panel performance as ROC curve comparison for different number of genes.
Figure 10B:
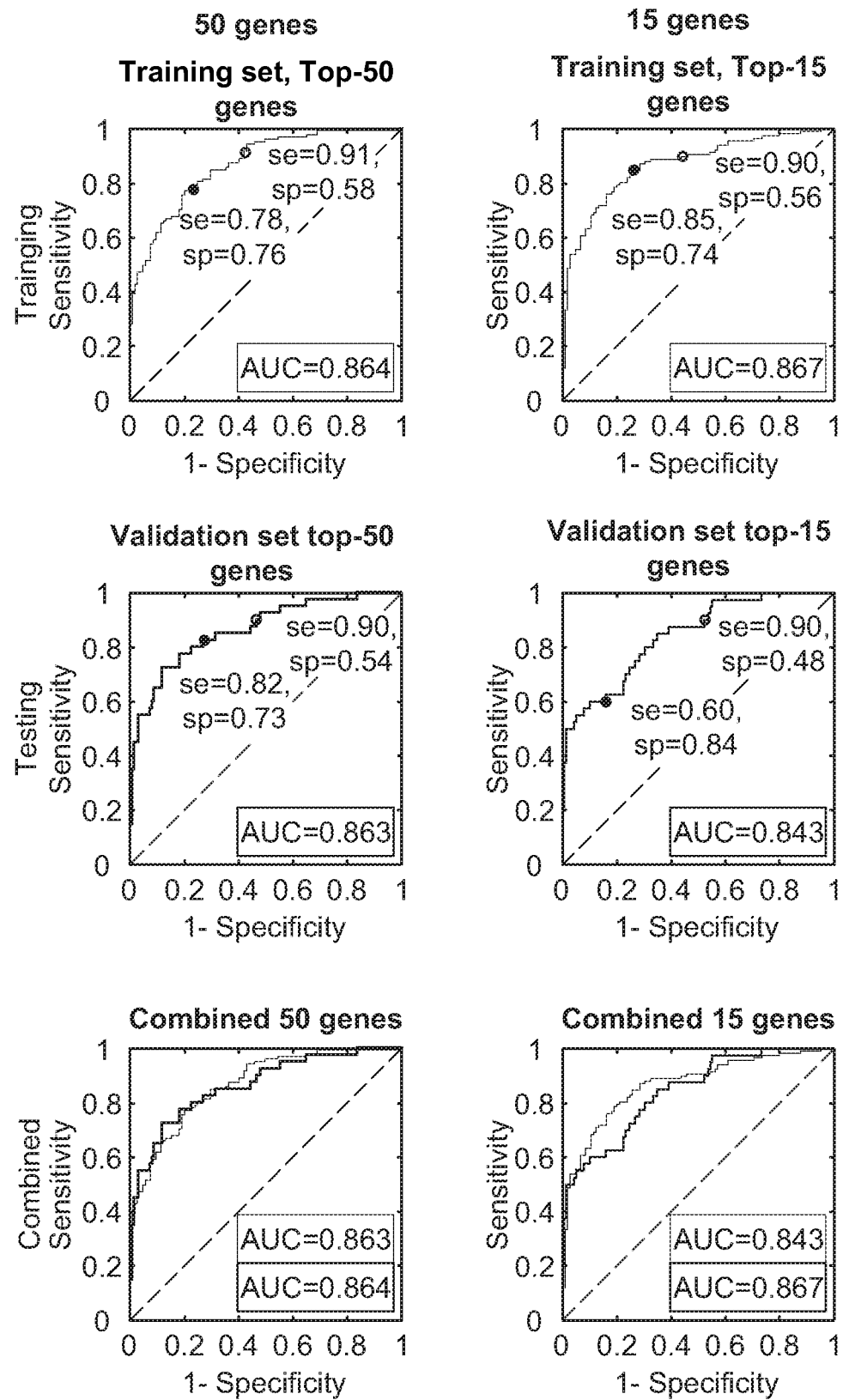

We first assessed how well the classification accuracies had been retained between the Illumina and NanoString platforms by re-assaying 199 of the samples from the microarray training set. For the comparison of the classification accuracies we only used the 276 microarray biomarkers that were successfully designed as NanoString probes. We observed a Spearman correlation rho=0.73 (p-value<$10^{-12}$) for the sample classification scores between the 2 platforms (FIG. 8A). The ROC-AUC based on the 276 probes was 0.881 for the microarrays and 0.838 for the NanoString (FIG. 8B) indicating that the platform transition was successful.

To carry out an unbiased assessment of the performance of the custom panel, we analyzed a total of 741 patient samples, including samples from a new 5$^{th}$ collection site. The final nPNC training set of 583 samples and the validation of 158 samples had balanced numbers of MN and BN samples (Table XI) to provide the best conditions for selecting a classifier with good sensitivity as well as specificity (17).

TABLE XI

Demographics of samples assayed with NanoString Custom Panel. Median ± IQR are given for continuous values, p-values indicates significance of comparison between Malignant and Benign nodule groups.

| Category | NanoString Lung Nodule Classifier Training Set | | | NanoString Lung Nodule Classifier Validation Set | | |
|---|---|---|---|---|---|---|
| | Malignant Nodules | Benign Nodules | p-value | Malignant Nodules | Benign Nodules | p-value |
| Total N | 290 | 293 | | 74 | 84 | |
| Gender | | | | | | |
| Female | 155 (53%) | 145 (49%) | 0.2530 | 45 (61%) | 44 (52%) | 0.2728 |
| Male | 135 (47%) | 145 (50%) | | 29 (39%) | 38 (45%) | |
| Unknown | 0 (0%) | 2 (1%) | | 0 (0%) | 2 (2%) | |
| Age | 68 ± 6 | 62 ± 6 | $3 \times 10^{-10}$ | 69 ± 7 | 85 ± 7 | 0.0097 |
| Race | | | | | | |
| Black | 34 (12%) | 20 (7%) | 0.0020 | 5 (7%) | 10 (12%) | 0.5134 |
| Other | 35 (12%) | 17 (6%) | | 8 (11%) | 10 (12%) | |
| White | 221 (75%) | 256 (87%) | | 61 (82%) | 64 (76%) | |
| Smoking | | | | | | |
| Current | 73 (25%) | 110 (38%) | 0.0124 | 23 (31%) | 22 (26%) | 0.8885 |
| Former | 198 (68%) | 170 (58%) | | 45 (61%) | 54 (64%) | |
| Never | 15 (5%) | 11 (4%) | | 5 (7%) | 6 (7%) | |
| Unknown | 4 (1%) | 2 (1%) | | 1 (1%) | 2 (2%) | |
| Pack Years | 40 ± 20 | 38 ± 13 | 0.6066 | 42 ± 19 | 42 ± 15 | 0.5767 |
| Lesion Size, mm | 22 ± 10 | 8 ± 4 | $4 \times 10^{-37}$ | 18 ± 6 | 7 ± 4 | $6 \times 10^{-10}$ |
| Cancer Stage | | | | | | |
| I | 173 (60%) | | | 47 (64%) | | |
| II | 41 (14%) | | | 9 (12) | | |
| III | 49 (17%) | | | 10 (14%) | | |
| IV | 4 (1%) | | | 1 (1%) | | |
| Unknown | 23 (8%) | 7 (9%) | | | | |
| Site* | | | | | | |
| HFGCC | 148 (50%) | 49 (17%) | $6 \times 10^{-26}$ | 37 (50%) | 15 (18%) | $2 \times 10^{-6}$ |
| NYU | 74 (26%) | 199 (68%) | | 24 (32%) | 62 (74%) | |
| Roswell-Parl | 11 (4%) | 13 (4%) | | 7 (9%) | 6 (7%) | |
| Temple | 3 (1%) | 11 (4%) | | 0 (0%) | 0 (0%) | |
| UPenn | 56 (19%) | 22 (8%) | | 6 (8%) | 1 (1%) | |

TABLE XII

Classification performance using different number of probes

| set | Performance Metric | N probes | | | |
|---|---|---|---|---|---|
| | | 559 | 100 | 41 | 6 |
| Training | Sensitivity | 76.5% | 73.4% | 74.7% | 73.7% |
| | Specificity | 76.6% | 73.8% | 74.8% | 73.4% |
| | Accuracy | 75.8% | 74.6% | 74.3% | 73.6% |
| | ROC-AUC | 0.833 | 0.825 | 0.834 | 0.800 |
| | ROC-AUC 95% CI | 0.799-0.864 | 0.790-0.857 | 0.800-0.865 | 0.765-0.836 |
| | Specifcity at 90% Sensitivity | 53.2% | 82.9% | 51.9% | 45.1% |
| | Positive Predictive Value (PPV) [a] | 0.056 | 0.049 | 0.052 | 0.048 |
| | Negative Predictive Value (NPV) [a] | 0.994 | 0.993 | 0.994 | 0.993 |
| Validation | Sensitivity | 67.6% | 67.5% | 68.9% | 52.7% |
| | Specificity | 83.3% | 83.3% | 82.1% | 85.7% |
| | Accuracy | 75.9% | 75.9% | 75.9% | 70.3% |
| | ROC-AUC | 0.826 | 0.817 | 0.825 | 0.782 |
| | ROC-AUC 95% CI | 0.760-0.891 | 0.749-0.885 | 0.759-0.890 | 0.709-0.855 |
| | Specifcity at 90% Sensitivity | 46.4% | 36.9% | 51.2% | 32.1% |
| | Positive Predictive Value (PPV) [a] | 0.069 | 0.069 | 0.066 | 0.063 |
| | Negative Predictive Value (NPV) [a] | 0.993 | 0.993 | 0.993 | 0.990 |

[a] Calculated using prevalence of 1.8% of lung cancer observed in the National Lung Screening Trial (NLST).

While the 41 probe classifier (Table IX) achieved an AUC of 0.834 (95% CI: 0.800-0.865) for training and 0.825 (95% CI: 0.759-0.890) for the independent validation (FIG. 4C), even using as few as 6 probes maintained ROC-AUC above 0.8, though there is a slight drop in the validation set performance (FIG. 4D).

The optimal 41 gene signature (Table IX) had an unbiased sensitivity and specificity of 68.1% and 82.1% respectively. It achieved a specificity of 51% at a sensitivity of 90% for both training and validation with NPV and PPV values of 0.99 and 0.0066 respectively for the independent validation. The classifier detected cancers with 64% sensitivity for Stage I and a sensitivity of 70% for later stage cancers. Probabilities of malignancy across a range of nPNC classification scores are shown in FIG. 4E. It should be noted that a small number of individuals with malignant or benign pulmonary nodules who had no history of smoking were included in the analysis. Removal of these subjects from the study did not change AUC validation performance for the 41 probe classifier (AUC difference of 0.001) or the full 559 probe classifier (AUC difference of 0.010). Adding age, sex, race, and smoking history as additional factors did not have an impact on the classification producing ROC-AUC of 0.837 as compared to 0.840 when only gene expression was used.

nPNC Classifier Outperforms Existing Clinical Models

Figure 5A:
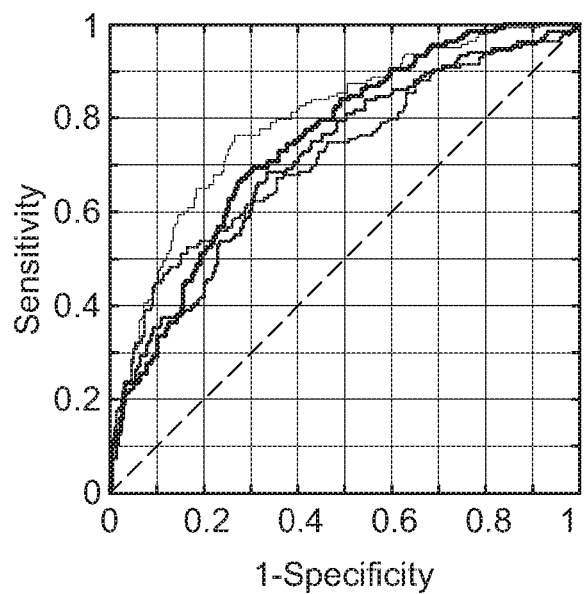
FIG. 5A and FIG. 5B show performance of the 41 probe nPNC for BN and MN in the 6-20 mm range.
Figure 5B:
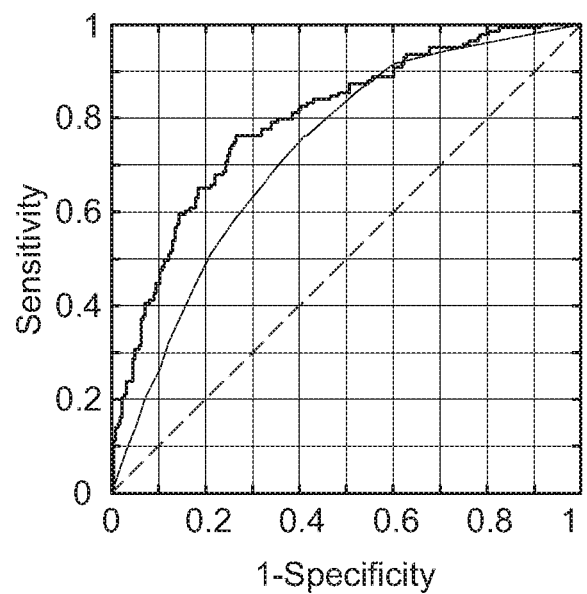

Focusing on the 41 biomarker panel classifier we compared the performance of the nPNC on all the samples in the difficult to assess 6-20 mm size range to the performance of three clinical algorithms, the Brock University developed in a high risk population (20, 21) and the Mayo Clinic (22) and VA (23) models developed using data from a more incidental nodule population. These algorithms assess the cancer risk of a pulmonary nodule based on a variety of demographic and pathological parameters including nodule size and location (FIG. 5A). The nPNC outperforms all 3 clinical models on nodules in the 6 to 20 mm diameter range. Since nodule size is a well-accepted risk factor included in each of the clinical models we also demonstrate an increased accuracy of the classification as compared to a classification using only size for the samples in the 6-20 mm range (FIG. 5B).

Classifier Performance for Different Nodules Size Ranges

Since nodule size is an important risk factor and the definition of IPNs is not very well defined (6) with changing guidelines, we examined the performance when comparing malignant and benign pulmonary nodules that were similar in size ranges. We calculated the performance of the 41-probe classifier across the various nodule size ranges using baseline positive thresholds of 4 mm from the NLST study (24) 6 mm and 8 mm as discussed in the recent reports from the Fleischner Society (8) and the Lung Rads (7) as well as a baseline threshold of 10 mm. The ROC-AUCs and the specificities when the sensitivity is held at a performance of 90% were calculated for all possible ranges for the selected thresholds for training and independent validation sets (FIG. 6). Overall, training and validation set performance was highly conserved across all size ranges except where only a few validation set samples fall within a particular size range as is evident in the smaller validation set. The 41 probe nPNC performs particularly well on independent validation with nodules in the difficult to diagnose 8-14 mm range, achieving a 64% Specificity at 90% Sensitivity, although the Specificity drops to 48% in the larger combined data set. Whether 4 mm or 6 mm is used as the threshold for a positive screen, our classifier demonstrates its utility in classifying IPNs by performing well across all ranges with a ROC-AUC of 0.83 and 0.81 respectively in the combined data set and a threshold 8 mm only reduces the AUC to 0.80. The Specificities at 90% Sensitivity are similarly stable and are calculated as 0.50, 0.46 and 0.48 for 4, 6 and 8 mm respectively.

Discussion

The overall benefits of lung cancer screening programs using LDCT are evident in the reported 20% increase in patient survival. However, this success comes with the associated problem of to how to evaluate the large numbers of primarily benign IPN being detected and the concern for over-management (25). The recent Lung-RADs assessment has also suggested that the implementation of a positive screening threshold of 6-7 mm rather than the 4 mm used in the NLST study may be more appropriate in the management of Lung Cancer Screening results (7) and that this change would reduce the magnitude of the IPN problem with a minimal effect on patient care (8). Even with new guidelines the potential for over-management of the estimated 1.6 million lung nodules detected each year in the US remains a significant challenge particularly for nodules ≥6 mm and less than ≤20 mm where the risk of malignancy can range from ~8 to 64% (26). The development of alternative non-invasive approaches to assess these IPNs in a clinically meaningful way is an important goal in pulmonary medicine.

Most non-invasive early detection approaches have depended on the identification of tumor derived nucleic acids, antibodies or proteins present in blood, plasma, serum or sputum (27-29) with the caveat that these analytes are frequently rare in the presence of smaller early stage cancers that are most amenable to curative surgery and which are now more being readily detected by LDCT. Additional studies that have avoided this issue have combined bronchoscopy with gene expression in normal airway epithelial cells or with gene expression associated with nasal brushings. This approach is based on the concept of "field cancerization" whereby the tumor induces gene expression alterations in the uninvolved respiratory tract that differs with the presence of a malignant or benign lung nodule. These approaches work well for nodules likely to be accessed by bronchoscopy (27, 30, 31) but are less effective with smaller IPNs that also represent a major management concern.

We previously showed that a malignant lesion in the lung can extend its influence beyond the pulmonary cancer field to the peripheral blood, as gene expression in PBMC derived RNA efficiently distinguishes malignant from benign lung nodules (9). The existence of this extra-pulmonary effect is supported by early reports from mouse models for lung cancer demonstrating that soluble factors produced by pre-malignant lesions in the lung influenced expression of specific activation markers in bone marrow macrophages and that this effect was enhanced with tumor progression (32-34). Although the PBMC studies provided an important proof of principal for extra pulmonary involvement, the need for the rapid purification of the PBMC samples in order to stabilize transcriptional profiles was a hindrance to expanding to collection sites outside of academic environments and to the development of a robust clinical platform. We have now demonstrated that RNA from whole blood, easily collected in PAXgene RNA stabilization tubes, can also be mined for gene expression information that distinguishes malignant from benign lung nodules. This minimally invasive, 2.5 ml blood collection system allows samples to be collected not only at major medical centers, but wherever blood is routinely drawn. The RNA stability at room temperature for 5 days means that no special storage system is required to maintain sample integrity, thereby facilitating sample collection and subsequent transfer to a central testing facility even from remote locations. The quality of the RNA makes it amenable to analysis on a wide variety of platforms including a variety of sequencing platforms that require high quality RNA.

We have tested the utility of the PAXgene collection system using samples collected at 4 academic pulmonary centers and from a community hospital. Samples were collected stored and transferred in bulk, or were collected daily then transferred by courier to our test site for storage and final processing without any detectable effect on platform performance. We built our diagnostic model from global gene expression assayed on Illumina microarrays with cancers that were primarily Stage I (69%) and II (17%) and nodules that ranged in size from the 4 mm threshold measurement of the NLST study to 20 mm, spanning the range of malignancy risk from <1% to 64% (8). Importantly our PAXgene microarray classifier maintained a ROC-AUC of 0.847 (95% CI: 0.742-0.951) on independent validation almost identical to that of the training set used for classifier development. In many studies, validation set accuracy is somewhat diminished suggesting the model used for classifier development was not large enough to adequately capture the potential subject diversity (9, 35, 36). Moving forward from the microarray developmental platform, we successfully transitioned the nodule classifier to the NanoString nCounter platform. The nCounter platform requires minimal sample handling, is technically simple and has the ability to evaluate degraded and non-degraded RNA in the same assay. The FDA approval of the NanoString based Prosigna™ Breast Cancer Prognostic Assay based on the PAM50 gene signature (14) and the more recent development of a NanoString based immune signature that predicts the clinical response to PD1 blockade (37) further supports the clinical utility of this platform.

While the preliminary gene panel for our NanoString based classifier included 559 biomarkers, that number could be reduced to 41 probes while maintaining the ROC-AUC and thus suggests the potential for simplifying the test platform. In assessing the contributions of the various probes represented in the 41 probes, 46% of the top ranked probes came from the SVM analysis, 29% from PCI panel and with the fewest candidates being selected by p value. The myeloid related genes linked to survival in our PBMC studies (18) were not represented in the 41 probe classifier but were well represented in the top 100 ranked probes while the NK related probes were mostly in the lower half of the probe set, perhaps because the NK signal is significantly diluted in the PAXgene samples. As patient outcome data is accumulated we will further assess the utility of the prognostic biomarkers included in our panel that were selected because of an association with recurrence/survival in our previous PBMC studies (18, 19, 38).

Although robust technical performance is important for any clinical platform, the resultant benefit to the patient is primary. The performance of our NanoString custom panel on the 741 samples analyzed on that platform has significant clinical implications with a potential to impact the use of invasive approaches for assessing some classes of difficult to diagnose IPN. Our study does not depend on the presence of circulating tumor cells, tumor proteins or tumor RNA whose presence is more consistent with more advanced cancers. In this study we have primarily addressed that class of indeterminate pulmonary nodules that are 6-20 mm in diameter, are of moderate to high risk (39) and frequently not easily accessible by either bronchoscopy or fine needle biopsies and early stage cancers that are most amenable to surgical approaches. We have also assessed the performance with smaller nodules in the 4-6 mm range where the risk of malignancy is small but whose presence can remain of some concern. Importantly our nPNC outperformed clinical algorithms presently used to stratify candidates with IPN for treatment or follow-up including the Brock University (20, 21) Mayo Clinic (22) and VA (23) clinical models in the 6-20 mm range. While these algorithms work well when applied to data sets that include mostly smaller benign nodules and larger cancers, performance is somewhat diminished when applied only to MN and BN in the problematic size range. Although the size range of pulmonary nodules we have analyzed is important there is still a significant difference in the median size between the MN and the BN in our study.

It will be important to address how well biomarkers and clinical algorithms function when BN and MN nodules are more closely matched in size and where clinical algorithms are likely to perform poorly. We attempted to test this type of comparison as shown in FIG. 4. While the overall AUCs, sensitivities and specificities are well conserved whether we use 4, 6 or 8 mm as a positive threshold, as the comparisons get more granular some comparisons are significantly more accurate than others and this is particularly evident in the validation study where samples number are smaller. We achieved a specificity of 64% at 90% sensitivity for BN and MN in the 8-14 mm size range dropping to 40% in the 6-14 mm range.

Nodule size is the primary consideration in how IPN are treated (40). While this study has interrogated a large number of patient samples and demonstrated potential utility, a further assessment with larger numbers of samples where MN and BN are more closely related by size will extend that utility as this is the scenario where size is no longer informative. In moving forward it will be important to more completely address the issue by the comparison of BN and MN of similar sizes across the range of nodule sizes that remain problematic. The highly simplified and proven method for the acquisition of large numbers of samples of consistent quality from a variety of locations will facilitate this process. Expanded studies will also allow us to address the biological basis for the differences we are detecting between the patient classes and to assess whether those differences may have therapeutic implications.

Each and every patent, patent application, publication, including International Patent Application No. PCT/US17/38571, and publicly available gene sequence cited throughout the disclosure is expressly incorporated herein by reference in its entirety. Also incorporated by reference are priority documents, U.S. Patent Application No. 62/607,756, filed Dec. 19, 2017, and U.S. Patent Application No. 62/752,163, filed Oct. 29, 2018. While this invention has been disclosed with reference to specific embodiments, it is apparent that other embodiments and variations of this invention are devised by others skilled in the art without departing from the true spirit and scope of the invention. The appended claims include such embodiments and equivalent variations.

The invention claimed is:

1. A set of multiple cDNA polynucleotides, cDNA oligonucleotides, or cDNA ligands, consisting of cDNA polynucleotides, cDNA oligonucleotides, or cDNA ligands each of which hybridize to a gene, gene fragment, or gene transcript in a group consisting of SLC25A20, P2RY5, DNAJB1, CCND3, CD160, MERTK, BCOR, ABCA5, RNASE2, IGFBP7, ITGAL, DYNC2LI1, EEF1B2, RAG1, DDIT4, ARG1, TBC1D12, AZI2, LOC100130229, STOM, MED16, EMR4, REPIN1, DNAJB6, IDO1, PSMB7, HSP90AB1, CABC1, PRPF3, PSMB8, TRIM39, CD48, CDH5, KLRC1, TUG1, PIM2, CLPTM1, REPS1, USP9Y, AFTPH, SLC6A12, wherein the set binds each gene, gene fragment, or gene transcript in the group.

2. The set of claim 1, wherein at least one cDNA polynucleotide or cDNA oligonucleotide is attached to a detectable label.

3. A kit comprising the set of claim 1 and a tube for holding blood, which contains a reagent which stabilizes the sample.

4. The kit according to claim 3, wherein the reagent stabilizes the mRNA in the sample.

* * * * *